United States Patent [19]
Carceller et al.

[11] Patent Number: 5,705,504
[45] Date of Patent: Jan. 6, 1998

[54] PIPERIDINE DERIVATIVES WITH PAF ANTAGONIST ACTIVITY

[75] Inventors: Elena Carceller, Sant Cugot; Pere J. Jimenez, Flix; Nuria Recasens, Barcelona; Jordi Salas, Montornés del Vallès; Carmen Almansa; Javier Bartrolí, both of Barcelona, all of Spain

[73] Assignee: J. Uriach & Cia, S.A., Barcelona, Spain

[21] Appl. No.: 669,440

[22] PCT Filed: Sep. 5, 1995

[86] PCT No.: PCT/EP95/03487

§ 371 Date: Oct. 22, 1996

§ 102(e) Date: Oct. 22, 1996

[87] PCT Pub. No.: WO96/14317

PCT Pub. Date: May 17, 1996

[30] Foreign Application Priority Data

Nov. 7, 1994 [ES] Spain ................ 9402291

[51] Int. Cl.⁶ .................. A61K 31/44; C07D 471/04
[52] U.S. Cl. ............................... 514/303; 546/118
[58] Field of Search ..................... 546/118; 514/303

[56] References Cited

U.S. PATENT DOCUMENTS 5,358,953  10/1994  Alker ..................... 514/290

FOREIGN PATENT DOCUMENTS

| 284359 | 9/1988 | European Pat. Off. . |
| 441226 | 8/1991 | European Pat. Off. . |
| 528172 | 2/1993 | European Pat. Off. . |
| 9305042 | 3/1993 | WIPO . |

OTHER PUBLICATIONS

"Quantitative Investigations into the Aggregation of Blood Platelets", G.V.R. Born, J. Physiol., 1962, 162, pp. 67–68.

*Primary Examiner*—C. Warren Ivy
*Assistant Examiner*—Evelyn Huang
*Attorney, Agent, or Firm*—Burns, Doane, Swecker & Mathis, L.L.P.

[57] ABSTRACT

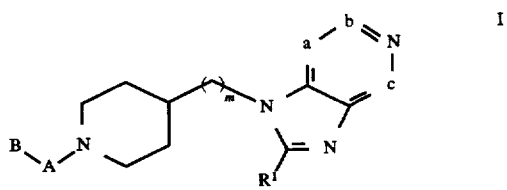

Compounds of general formula I and their salts and solvates are PAF antagonists and as such are useful in the treatment of various diseases or disorders mediated by PAF. Pharmaceutical compositions including these compounds and processes for their preparation are also provided.

21 Claims, No Drawings

PIPERIDINE DERIVATIVES WITH PAF ANTAGONIST ACTIVITY

This application is the National phase of PCT/EP 95/03487, filed Sep. 9, 1995.

FIELD OF THE INVENTION

The present invention relates to new piperidine derivatives which are potent platelet activating factor (PAF) antagonists. The invention also relates to a process for their preparation, to pharmaceutical compositions containing them and to their use in the treatment of diseases in which PAF is involved.

DESCRIPTION OF THE PRIOR ART

Platelet activating factor (PAF) or (1-O-alkyl-2-acetyl-sn-glyceryl-3-phosphorylcholine), also called acetyl glyceryl ether phosphorylcholine (AGEPC) or PAF-acether, is a natural phospholipid synthesized by different cells (basophiles, macrophages, neutrophiles, platelets) and tissues (heart, lung and kidney) of the organism.

PAF was described for the first time as a potent platelet aggregating agent. Later on it was demonstrated to have other biological activities in vivo, such as peripheral vasodilatation, increase of the vascular permeability, induction of bronchoconstriction and hyperreactivity of the respiratory tract. PAF also produces immediate hypotension followed by pulmonary and renal hypertension in rats, guinea pigs, rabbits and dogs, and it has been rated as the most potent ulcerogenic agent described until now.

Consequently, PAF is a mediator that is implicated in a large set of pathological processes such as asthma, septic shock, transplant rejection, thrombosis, ulceration, inflammation and renal diseases.

The closest, prior art from the structural point of view is believed to be EP 441226, which discloses pyridylcyanomethylpiperazines and piperidines having PAF antagonistic activity, different from the compounds of the present invention.

DESCRIPTION OF THE INVENTION

The present invention relates to new piperidine derivatives of general formula I

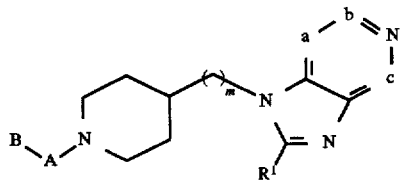

wherein:

m represents 0, 1 or 2;

a, b and c represent CR, wherein each R independently represents hydrogen or $C_{1-4}$ alkyl;

$R^1$ represents $C_{1-4}$ alkyl or $C_{3-7}$ cycloalkyl;

A represents —CO—, —$SO_2$—, —NHCO— or —OCO—;

B represents a group of formula (i), and when A represents —CO— or —$SO_2$—, then B can also represent a group of formula (ii) or (iii)

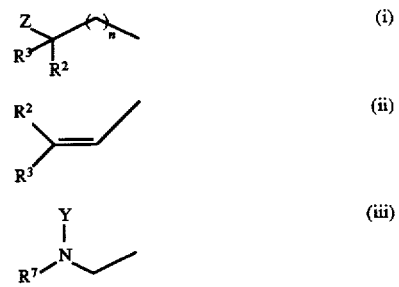

n represents 0, 1, 2 or 3;

one of $R^2$ or $R^3$ represents $C_{1-4}$ alkyl, $C_{3-7}$ cycloalkyl or aryl, and the other represents hydrogen, $C_{1-4}$ alkyl, $C_{1-4}$ haloalkyl, $C_{3-7}$ cycloalkyl, $C_{1-4}$ alkoxy-$C_{1-4}$ alkyl, aryl or aryl-$C_{1-4}$alkyl;

Z represents hydrogen, $C_{1-4}$ alkyl, —$CH_2$—$OR^4$, —$COOR^4$ or —$CONR^4R^5$, and when A represents —CO— or —$SO_2$—, then Z can also be hydroxy, —$NR^4R^5$, —$NR^6C(=O)OR^4$, —$NR^6C(=O)R^4$, —$NR^6C(=O)NR^4R^5$, —$N(OH)C(=O)NR^4R^5$ or —$NR^6SO_2R^4$;

or Z and $R^3$ together form a $C_{2-5}$ polymethylene chain in which case $R^2$ represents $C_{1-4}$ alkyl, $C_{3-7}$ cycloalkyl or aryl;

$R^4$ represents hydrogen, $C_{1-4}$ alkyl, aryl or aryl-$C_{1-4}$ alkyl;

$R^5$ and $R^6$ independently represent hydrogen or $C_{1-4}$ alkyl;

$R^7$ represents $C_{1-4}$ alkyl, $C_{3-7}$ cycloalkyl, aryl, aryl-$C_{1-4}$ alkyl or bisaryl-$C_{1-4}$ alkyl;

Y represents hydrogen, $C_{1-4}$ alkyl, aryl, aryl-$C_{1-4}$ alkyl, —$C(=O)OR^4$, —$C(=O)R^4$, —$C(=O)NR^4R^5$, or —$SO_2R^4$;

aryl, whenever appearing in the above definitions, represents phenyl or phenyl substituted with 1, 2, 3 or 4 groups independently selected from halogen, $C_{1-4}$ alkyl, $C_{1-4}$ alkoxy, hydroxy, $C_{1-4}$ haloalkyl, $C_{1-4}$ haloalkoxy, cyano, nitro, amino, $C_{1-4}$ alkylamino, $C_{1-4}$ dialkylamino, $C_{1-4}$ alkylcarbonyl, $C_{1-4}$ alkylcarbonyloxy, $C_{1-4}$ alkoxycarbonyl, $C_{1-4}$ alkylsulfonyl, $C_{1-4}$ alkylsulfinyl, $C_{1-4}$ alkylthio, $C_{1-4}$ alkylcarbonylamino or $C_{1-4}$ alkoxycarbonylamino; and their salts and solvates.

The invention also provides a pharmaceutical composition which comprises an effective amount of a compound of formula I or a pharmaceutically acceptable salt or solvate thereof and a pharmaceutically acceptable excipient.

The invention further provides the use of a compound of formula I or a pharmaceutically acceptable salt or solvate thereof for the manufacture of a medicament for the treatment or prevention of diseases mediated by PAF. Preferred is the use for the manufacture of a medicament for the treatment or prevention of ischemia and shock states such as septic shock, anaphylactic shock, hemorrhagic shock and myocardial ischemia; pancreatitis; and diseases related with allergy and inflammation such as asthma, dermatitis, urticaria, arthritis and psoriasis.

The invention also provides the use of a compound of formula I or a pharmaceutically acceptable salt or solvate thereof for the treatment or prevention of diseases mediated by PAF. Preferred is the use for the treatment or prevention of ischemia and shock states such as septic shock, anaphylactic shock, hemorrhagic shock and myocardial ischemia; pancreatitis; and diseases related with allergy and inflammation such as asthma, dermatitis, urticaria, arthritis and psoriasis.

The invention further provides a method of treating or preventing diseases mediated by PAF in a mammal, which comprises administering to said mammal an effective amount of a compound of formula I or a pharmaceutically acceptable salt or solvate thereof. Preferred is a method of treating or preventing ischemia and shock states such as septic shock, anaphylactic shock, hemorrhagic shock and myocardial ischemia; pancreatitis; and diseases related with allergy and inflammation such as asthma, dermatitis, urticaria, arthritis and psoriasis in a mammal in need thereof, the method comprising administering to the mammal an effective amount of a compound of formula I or a pharmaceutically acceptable salt or solvate thereof.

The invention still further provides a process for preparing a compound of formula I which comprises:

(A) reacting a compound of formula II,

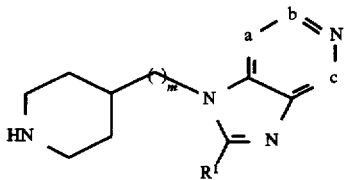

II wherein a, b, c, m and $R^1$ have the previously described meaning, with an acid of formula BCOOH (III) or a suitable derivative thereof such as the acid chloride or the anhydride, a sulfonyl chloride of formula $BSO_2Cl$ (IV), a compound of formula BOC(=O)G (V), a compound of formula BNHC(=O)G (VI) or a compound of formula BN=C=O (VII), wherein B has the previously described meaning and G represents a good leaving group such as chloro or —OPh; or (B) converting in one or a plurality of steps a compound of formula I into another compound of formula I; and (C) if desired, after steps A or B, reacting a compound of formula I with an acid to give the corresponding acid addition salt.

The invention yet further provides novel intermediates of formula II

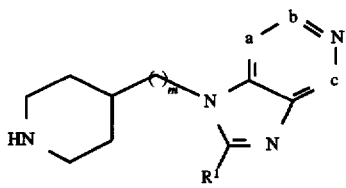

II wherein a, b, c, m and $R^1$ have the meaning described above for the compounds of formula I. The compounds of formula II are valuable intermediates in the preparation of the compounds of the present invention.

Compounds of formula I may have one or more aymmetric centers, which can give rise to stereoisomers. The present invention covers each of the individual stereoisomers as well as their mixtures. Moreover, some compounds of the present invention may show cis/trans isomery. The present invention covers each of the geometric isomers and the mixtures thereof.

In the above definitions, the term $C_{1-4}$ alkyl, as a group or part of a group, means a linear or branched alkyl group that contains from one to four carbon atoms. Therefore, it includes methyl, ethyl, propyl, isopropyl, butyl, isobutyl, sec-butyl, and tert-butyl.

The term $C_{1-4}$ alkoxy, as a group or part of a group, means a group derived from the union of a $C_{1-4}$ alkyl group like the above mentioned to an oxygen atom of an ether functional group. Examples include methoxy, ethoxy, propoxy, isopropoxy, butoxy, isobutoxy, sec-butoxy, and tert-butoxy.

A halogen group or its abbreviation halo represents fluoro, chloro, bromo or iodo.

A group $C_{3-7}$ cycloalkyl represents cyclopropyl, cyclobutyl, cyclopentyl, cyclohexyl or cycloheptyl.

A group $C_{2-5}$ polymethylene represents ethylene, propylene, butylene and pentylene.

A $C_{1-4}$ haloalkyl group means a group resulting from the substitution of one or more hydrogen atoms of a $C_{1-4}$ alkyl group by one or more halogen atoms (i.e. fluorine, chlorine, bromine or iodine), which can be the same or different. Examples include trifluoromethyl, fluoromethyl, chloroethyl, fluoroethyl, iodoethyl, 2,2,2-trifluoroethyl, pentafluoroethyl, fluoropropyl, chloropropyl, 2,2,3,3,3-pentafluoropropyl, heptafluoropropyl, fluorobutyl, and nonafluorobutyl.

A $C_{1-4}$ haloalkoxy group means a group resulting from the substitution of one or more hydrogen atoms of a $C_{1-4}$ alkoxy group by one or more halogen atoms, which can be the same or different. Examples include trifluoromethoxy, fluoromethoxy, chloroethoxy, fluoroethoxy, iodoethoxy, 2,2,2-trifluoroethoxy pentafluoroethoxy, fluoropropoxy, chloropropoxy, 2,2,3,3,3-pentafluoropropoxy, heptafluoropropoxy, fluorobutoxy, and nonafluorobutoxy.

A $C_{1-4}$ alkylamino or $C_{1-4}$ dialkylamino group represents a group resulting from the substitution of one or two hydrogen atoms, respectively, of an amino group by one or two $C_{1-4}$ alkyl groups, which can be the same or different. Examples include methylamino, dimethylamino, ethylamino, diethylamino, ethylmethylamino, propylamino, dipropylamino, isopropylamino and diisopropylamino.

A $C_{1-4}$ alkylcarbonyl group represents a group resulting from the union of a $C_{1-4}$ alkyl group to a carbonyl group. Examples include acetyl, propionyl, isopropionyl, and butanoyl.

A $C_{1-4}$ alkylcarbonyloxy group represents a group resulting from the union of a $C_{1-4}$ alkylcarbonyl group to an oxygen atom of an ether functional group. Examples include acetyloxy, propionyloxy, isopropionyloxy, and butanoyloxy.

A $C_{1-4}$ alkoxycarbonyl group represents a group resulting from the union of a $C_{1-4}$ alkoxy group to a carbonyl group. Examples include methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl.

A $C_{1-4}$ alkylsulfonyl group represents a group resulting from the union of a $C_{1-4}$ alkyl group to a sulfonyl group. Examples include methylsulfonyl, ethylsulfonyl, propylsulfonyl, isopropylsulfonyl, butylsulfonyl, isobutylsulfonyl, sec-butylsulfonyl, and tert-butylsulfonyl.

A $C_{1-4}$ alkylsulfinyl group represents a group resulting from the union of a $C_{1-4}$ alkyl group to a sulfinyl group. Examples include methylsulfinyl, ethylsulfinyl, propylsulfinyl, isopropylsulfinyl, butylsulfinyl, isobutylsulfinyl, sec-butylsulfinyl, and tert-butylsulfinyl.

A $C_{1-4}$ alkylthio group represents a group resulting from the union of a $C_{1-4}$ alkyl group to a sulphur atom of a thioether funtional group. Examples include methylthio, ethylthio, propylthio, isopropylthio, butylthio, isobutylthio, sec-butylthio, and tert-butylthio.

A $C_{1-4}$ alkylcarbonylamino group represents a group resulting from the substitution of a hydrogen atom of an amino group by a $C_{1-4}$ alkylcarbonyl group. Examples include acetamido, propanamido and isopropanamido.

A $C_{1-4}$ alkoxycarbonylamino group represents a group resulting from the substitution of a hydrogen atom of an amino group by a $C_{1-4}$ alkoxycarbonyl group. Examples include methoxycarbonylamino, ethoxycarbonylamino, propoxycarbonylamino, isopropoxycarbonylamino, butoxycarbonylamino, isobutoxycarbonylamino, sec-butoxycarbonylamino and tert-butoxycarbonylamino.

A $C_{1-4}$ alkoxy$C_{1-4}$ alkyl group represents a group resulting from the substitution of a hydrogen atom of a $C_{1-4}$ alkyl group by a $C_{1-4}$ alkoxy group. Examples include among others methoxymethyl, ethoxymethyl, propoxymethyl, isopropoxymethyl, butoxymethyl, isobutoxymethyl, sec-butoxymethyl, tert-butoxymethyl, 2-methoxyethyl, 2-ethoxyethyl, 2-propoxyethyl, 2-isopropoxyethyl, 2-butoxyethyl, 2-isobutoxyethyl, 2-sec-butoxyethyl, 2-tert-butoxyethyl, 1-methoxyethyl, 1-ethoxyethyl, 1-propoxyethyl, 1-isopropoxyethyl, 1-butoxyethyl, 1-isobutoxyethyl, 1-sec-butoxyethyl, and 1-tert-butoxyethyl.

An aryl-$C_{1-4}$ alkyl group represents a group resulting from the substitution of one hydrogen atom of a $C_{1-4}$ alkyl group by an aryl group as defined above. Examples include among others, benzyl, 1-phenylethyl, 3-phenylpropyl, 2-phenylpropyl, 1-phenylpropyl, 4-phenylbutyl, 3-phenylbutyl, 2-phenylbutyl and 1-phenylbutyl, wherein the phenyl groups can be substituted as described above in the definition of an aryl group.

A bisaryl-$C_{1-4}$ alkyl group represents a group resulting from the substitution of two hydrogen atoms of a $C_{1-4}$ alkyl group by two aryl groups as defined above, which can be the same or different. Examples include among others, diphenylmethyl, 2,2-diphenylethyl, 1,1-diphenylethyl, 1,2-diphenylethyl, 3,3-diphenylpropyl, 2,2-diphenytpropyl, 1,1-diphenylpropyl, 3,2-diphenylpropyl, 1,3-diphenylpropyl, and 1,2-diphenylpropyl, wherein the phenyl groups can be substituted as described above in the definition of an aryl group.

Preferred compounds include those in which, independently or in any compatible combination:

m represents 1 or 2;

n represents 0, 1 or 2;

A represents —CO— or —$SO_2$—;

A represents —NHCO—or —OCO—;

B represents a group of formula (i);

B represents a group of formula (ii);

B represents a group of formula (iii)

Z represents hydrogen, $C_{1-4}$ alkyl, —$CH_2$—$OR^4$, —$COOR^4$, or —$CONR^4R^5$, and when A represents —CO— or —$SO_2$—, Z can also represent hydroxy, —$NR^6C(=O)OR^4$, —$NR^6C(=O)R^4$ or —$NR^6SO_2R^4$;

Z and $R^3$ together form a $C_{2-5}$ polymethylene chain;

$R^7$ represents $C_{1-4}$ alkyl, $C_{3-7}$ cycloalkyl or aryl;

aryl represents phenyl or phenyl substituted with 1, 2, 3 or 4 groups independently selected from halogen, $C_{1-4}$ alkyl, $C_{1-4}$ alkoxy, hydroxy, $C_{1-4}$ haloalkyl, $C_{1-4}$ haloalkoxy or amino.

Accordingly, a preferred class of compounds of formula I is that wherein:

m represents 1 or 2;

a, b and c represent CR, wherein each R independently represents hydrogen or $C_{1-4}$ alkyl;

$R^1$ represents $C_{1-4}$ alkyl or $C_{3-7}$ cycloalkyl;

A represents —CO— or —$SO_2$—;

B represents a group of formula (i), (ii) or (iii)

n represents 1 or 2;

one of $R^2$ or $R^3$ represents $C_{1-4}$ alkyl, $C_{3-7}$ cycloalkyl or aryl, and the other represents hydrogen, $C_{1-4}$ alkyl, $C_{1-4}$ haloalkyl, $C_{3-7}$ cycloalkyl, $C_{1-4}$ alkoxy-$C_{1-4}$ alkyl, aryl or aryl-$C_{1-4}$alkyl;

Z represents hydrogen, $C_{1-4}$ alkyl, —$CH_2$—$OR^4$, —$COOR^4$, —$CONR^4R^5$, hydroxy, —$NR^6C(=O)OR^4$, —$NR^6C(=O)R^4$ or —$NR^6SO_2R^4$;

or Z and $R^3$ together form a $C_{2-5}$ polymethylene chain in which case $R^2$ represents $C_{1-4}$ alkyl, $C_{3-7}$ cycloalkyl or aryl;

$R^4$ represents hydrogen, $C_{1-4}$ alkyl, aryl or aryl-$C_{1-4}$ alkyl;

$R^5$ and $R^6$ independently represent hydrogen or $C_{1-4}$ alkyl;

$R^7$ represents $C_{1-4}$ alkyl, $C_{3-7}$ cycloalkyl or aryl;

Y represents hydrogen, $C_{1-4}$ alkyl, aryl, aryl-$C_{1-4}$ alkyl, —$C(=O)OR^4$, —$C(=O)R^4$, —$C(=O)NR^4R^5$, or —$SO_2R^4$; and aryl in the above definitions represents phenyl or phenyl substituted with 1, 2, 3 or 4 groups independently selected from halogen, $C_{1-4}$ alkyl, $C_{1-4}$ alkoxy, hydroxy, $C_{1-4}$ haloalkyl, $C_{1-4}$ haloalkoxy or amino.

A preferred group of compounds within this class is that wherein:

B represents a group of formula (i) or (iii);

one of $R^2$ or $R^3$ represents $C_{1-4}$ alkyl, $C_{3-7}$ cycloalkyl or aryl, and the other represents hydrogen, $C_{1-4}$ alkyl, $C_{1-4}$ haloalkyl, $C_{3-7}$ cycloalkyl, $C_{1-4}$ alkoxy-$C_{1-4}$ alkyl, aryl or aryl-$C_{1-4}$ alkyl;

Z represents hydrogen, $C_{1-4}$ alkyl, —$CH_2$—$OR^4$, —$COOR^4$ or hydroxy;

or Z and $R^3$ together form a $C_{2-5}$ polymethylene chain in which case $R^2$ represents $C_{1-4}$ alkyl, $C_{3-7}$ cycloalkyl or aryl;

$R^4$ represents hydrogen, $C_{1-4}$ alkyl, aryl or aryl-$C_{1-4}$ alkyl;

$R^7$ represents $C_{1-4}$ alkyl, $C_{3-7}$ cycloalkyl or aryl; and

Y represents $C_{1-4}$ alkyl, aryl, or -$SO_2R^4$.

Another preferred group of compounds within this class is that wherein:

B represents a group of formula (ii); and one of $R^2$ or $R^3$ represents $C_{1-4}$ alkyl or aryl, and the other represents hydrogen, $C_{1-4}$ alkyl, $C_{1-4}$ alkoxy-$C_{1-4}$ alkyl, aryl or aryl $C_{1-4}$ alkyl.

Another preferred class of compounds of formula I is that wherein:

m represents 1 or 2;

a, b and c represent CR, wherein each R independently represents hydrogen or $C_{1-4}$ alkyl;

$R^1$ represents $C_{1-4}$ alkyl or $C_{3-7}$ cycloalkyl;

A represents —NHCO— or —OCO—;

B represents a group of formula (i);

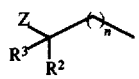

n represents 0 or 1;

one of $R^2$ or $R^3$ represents $C_{1-4}$ alkyl, $C_{3-7}$ cycloalkyl or aryl, and the other represents hydrogen, $C_{1-4}$ alkyl, $C_{1-4}$ haloalkyl, $C_{3-7}$ cycloalkyl, $C_{1-4}$ alkoxy-$C_{1-4}$ alkyl, aryl, or aryl-$C_{1-4}$ alkyl;

Z represents hydrogen, $C_{1-4}$ alkyl, —$CH_2$—$OR^4$, —$COOR^4$, or —$CONR^4R^5$;

or Z and $R^3$ together form a $C_{2-5}$ polymethylene chain in which case $R^2$ represents $C_{1-4}$ alkyl, $C_{3-7}$ cycloalkyl or aryl;

$R^4$ represents hydrogen, $C_{1-4}$ alkyl, aryl or aryl-$C_{1-4}$ alkyl;

$R^5$ represents hydrogen or $C_{1-4}$ alkyl; and aryl in the above definitions represents phenyl or phenyl substituted with 1, 2, 3 or 4 groups independently selected from halogen, $C_{1-4}$ alkyl, $C_{1-4}$ alkoxy, hydroxy, $C_{1-4}$ haloalkyl, $C_{1-4}$ haloalkoxy or amino.

The formulae of some specific compounds are represented below, together with the number corresponding to the example in which their preparation is described:

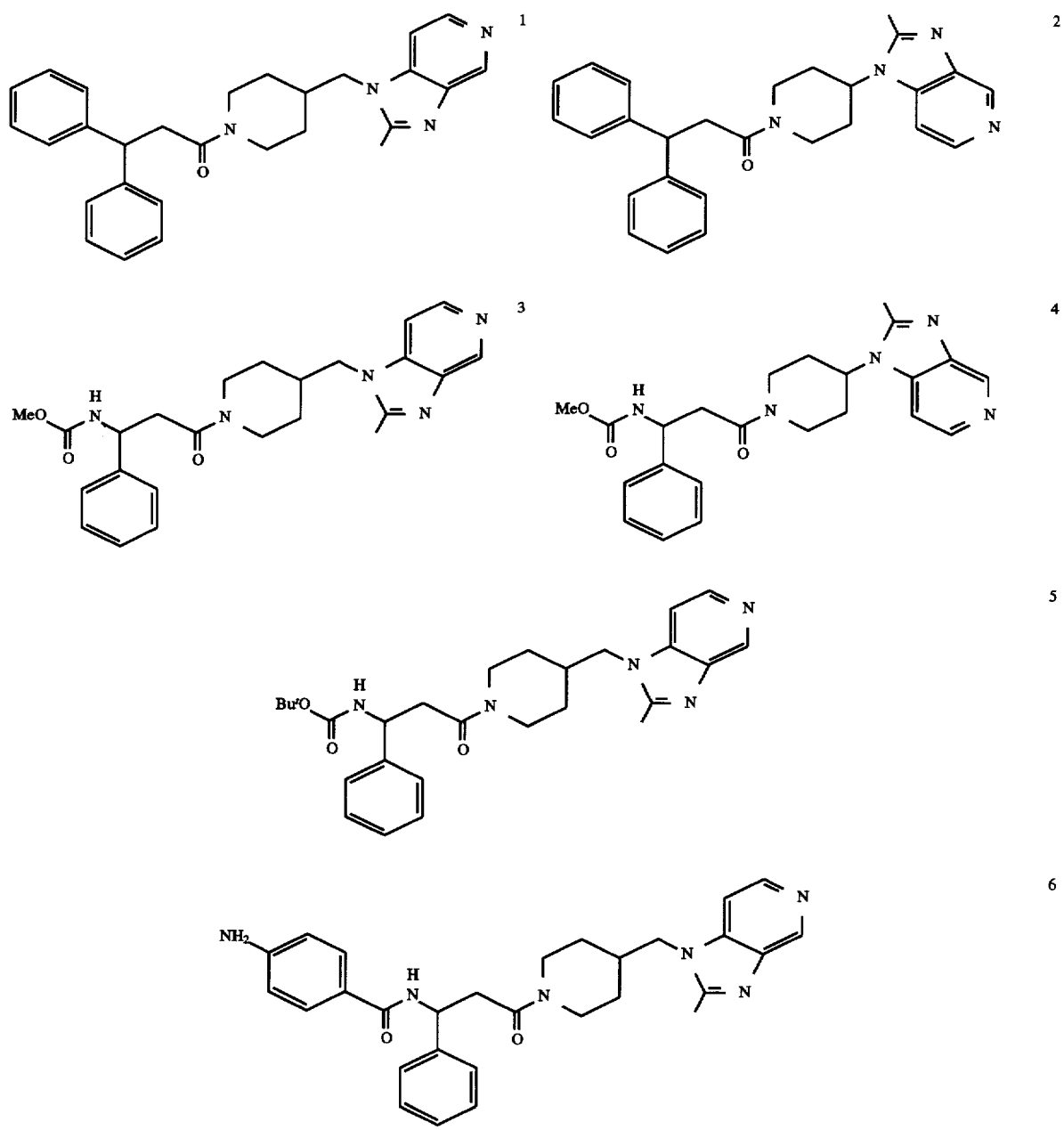

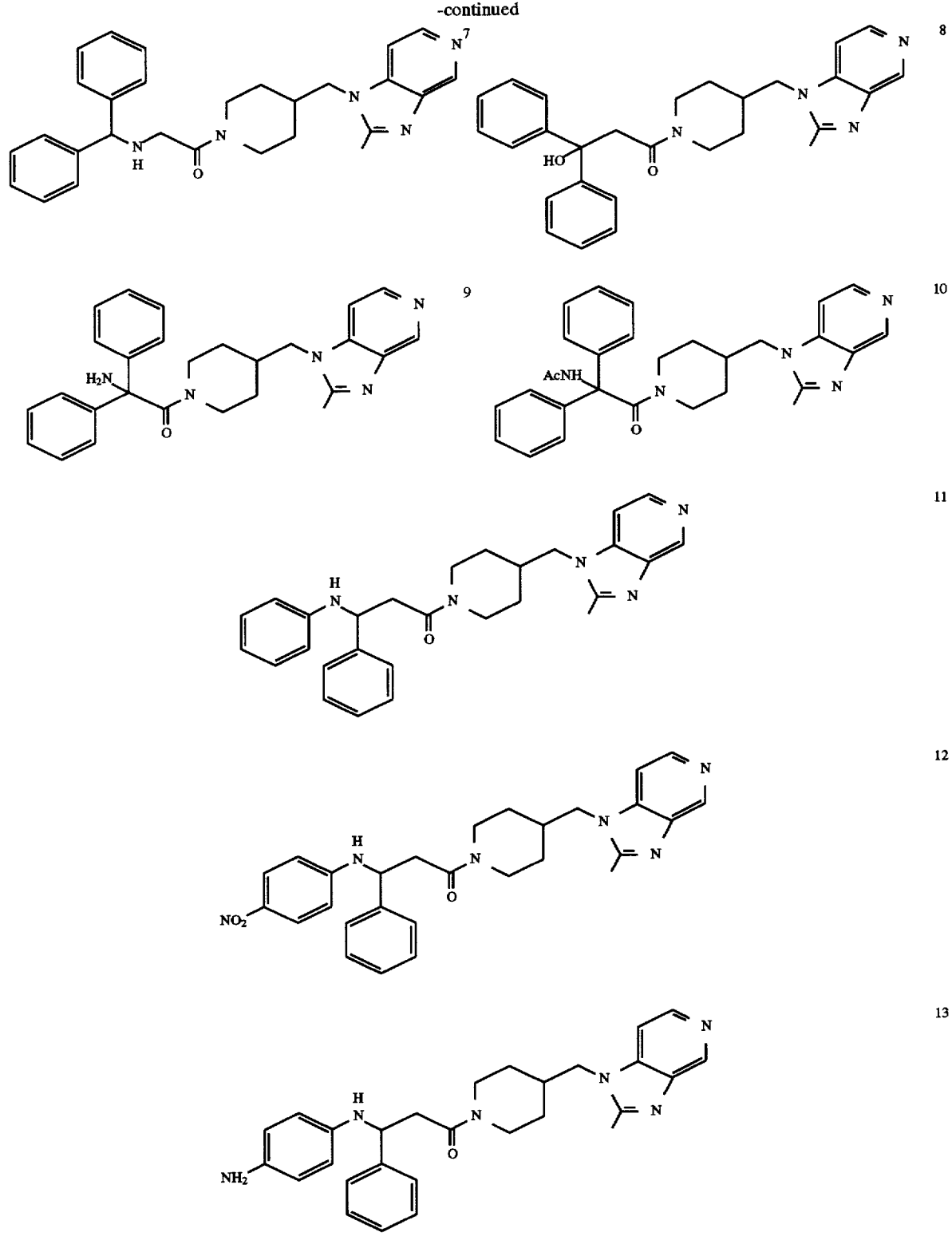

11 12
-continued
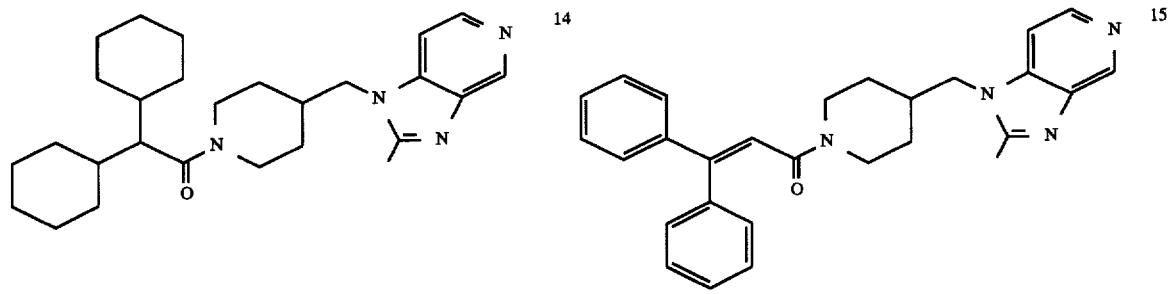
14 15
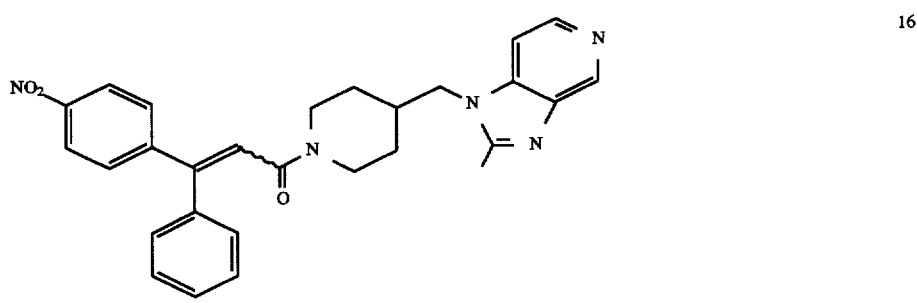
16
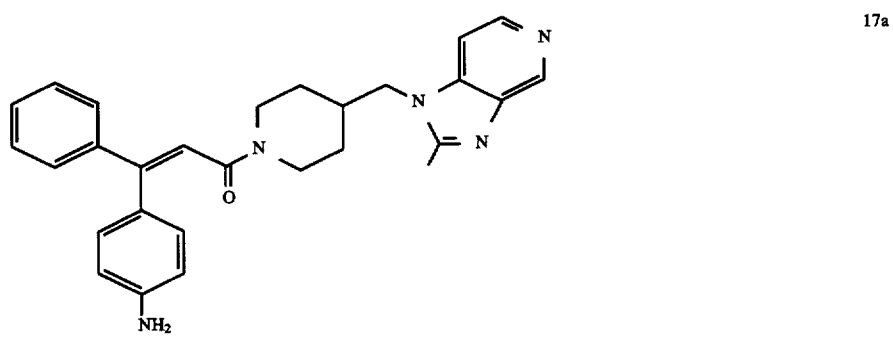
17a
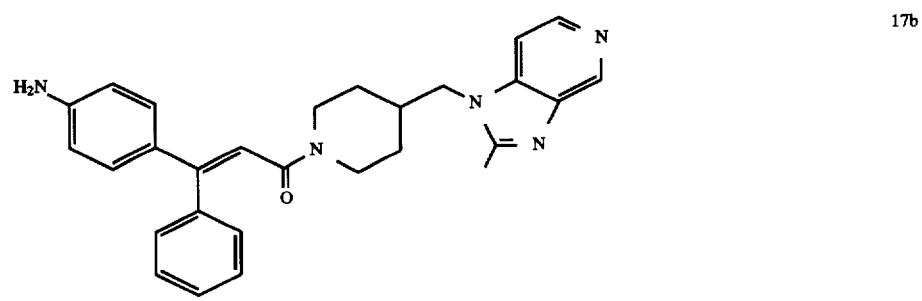
17b
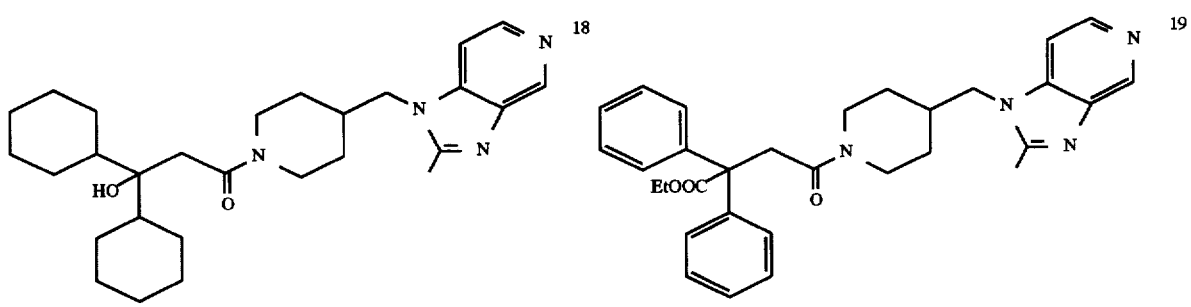
18 19

-continued
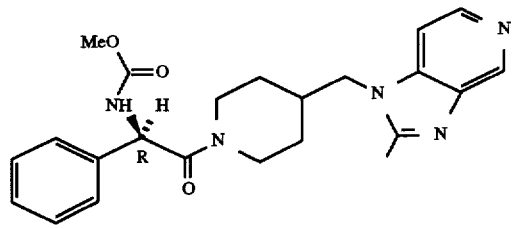
20
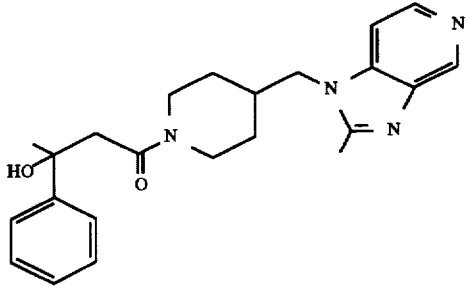
21
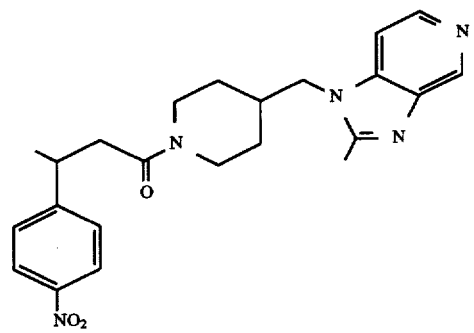
22
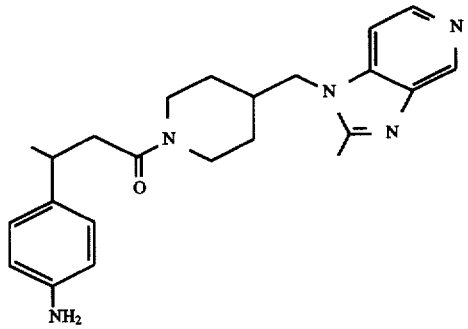
23
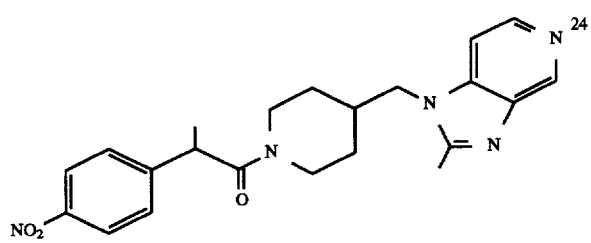
24
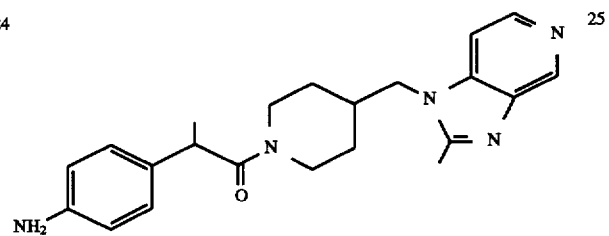
25
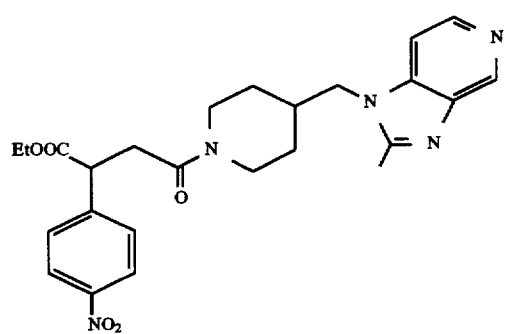
26
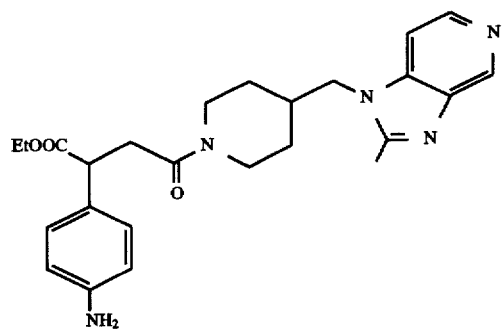
27
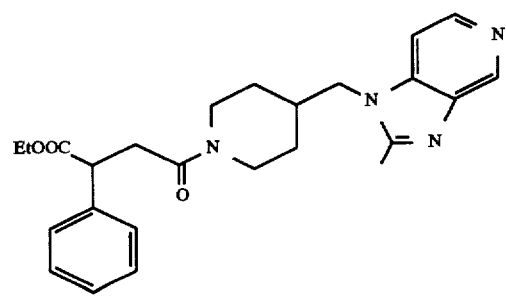
28
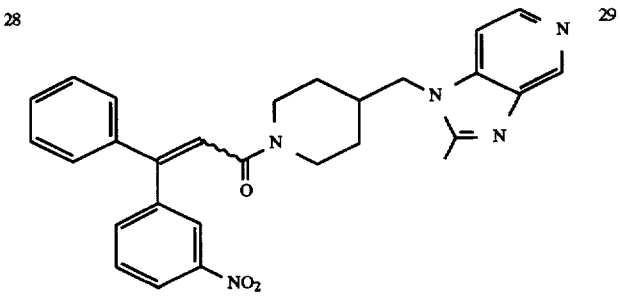
29

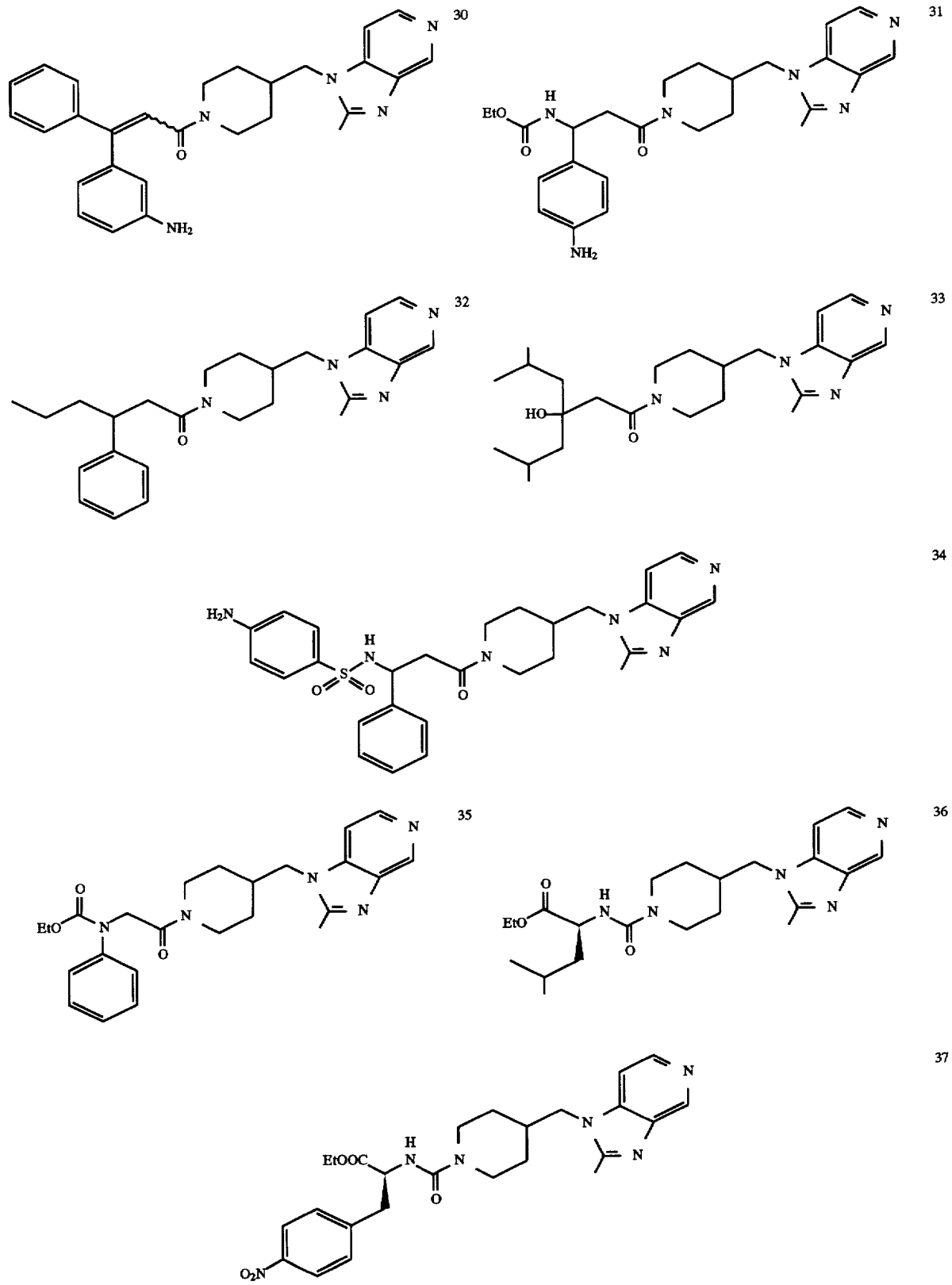

-continued
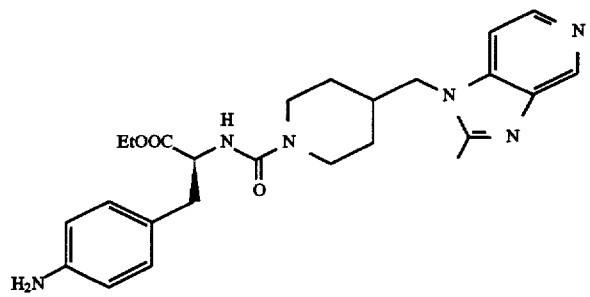
38
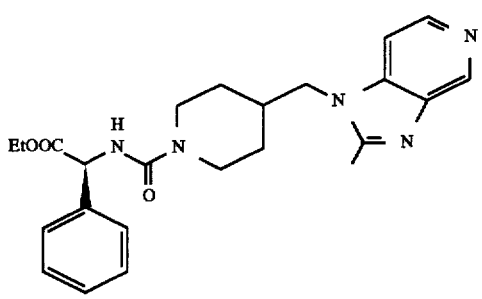
39
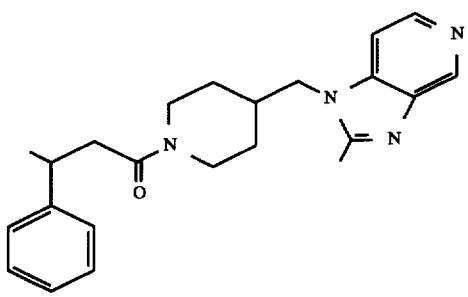
40
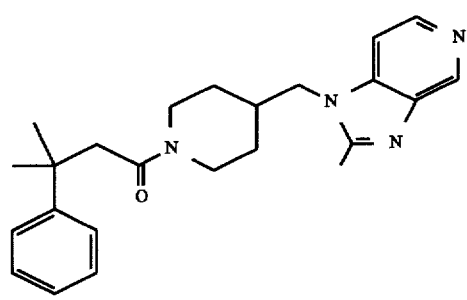
41
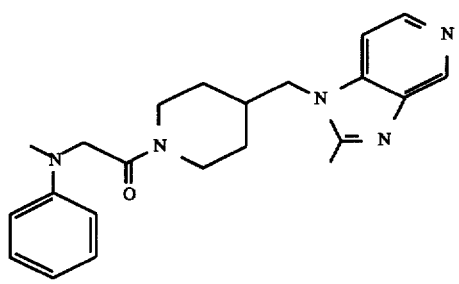
42
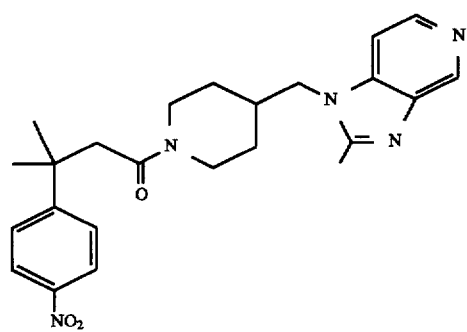
43
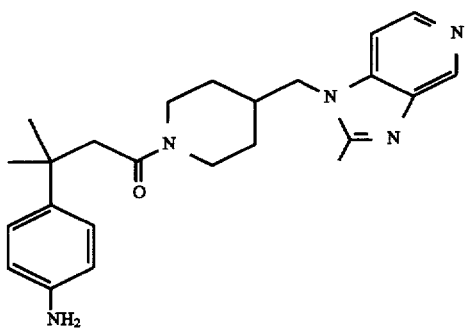
44
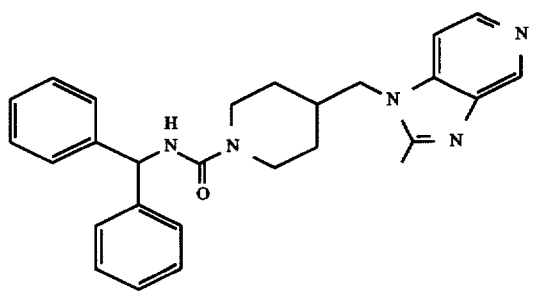
45

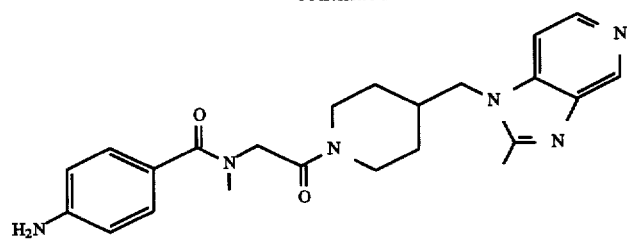
46
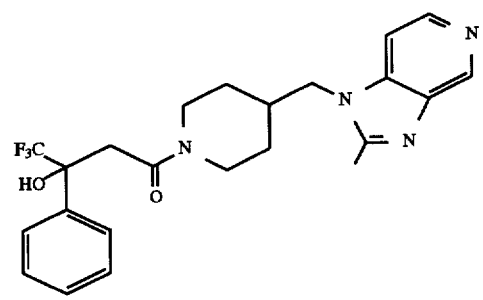
47
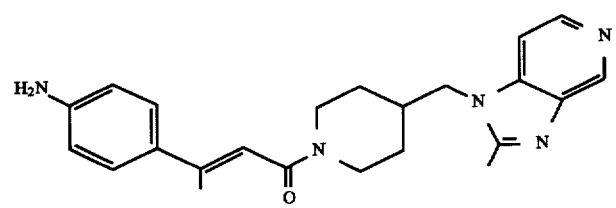
48
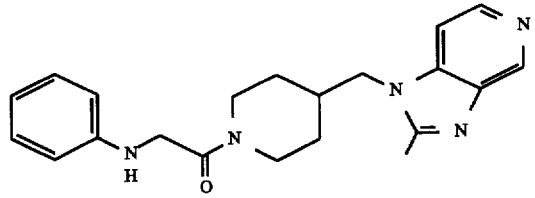
49
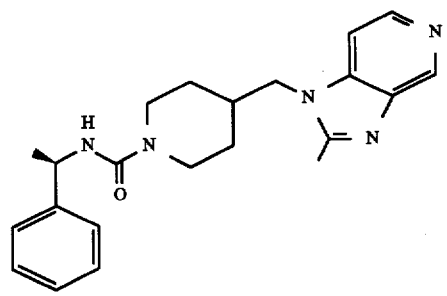
50
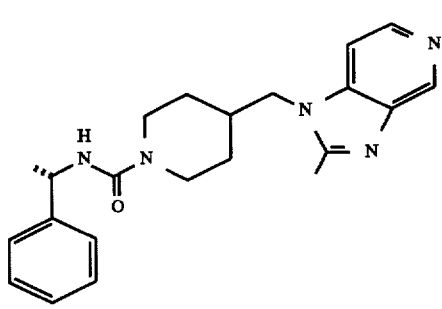
51
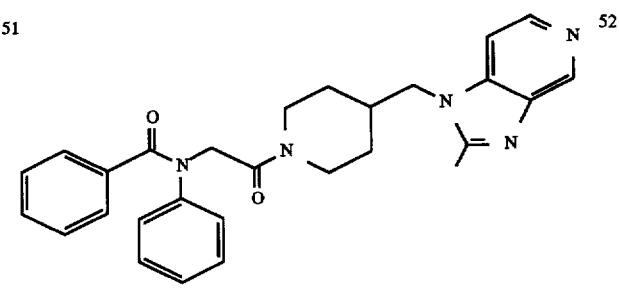
52
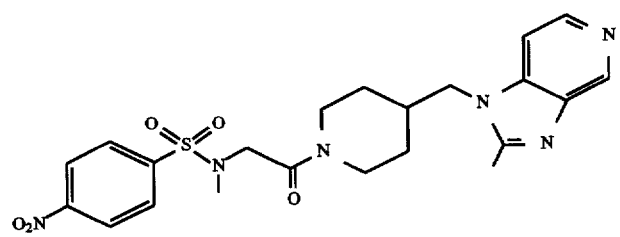
53

-continued
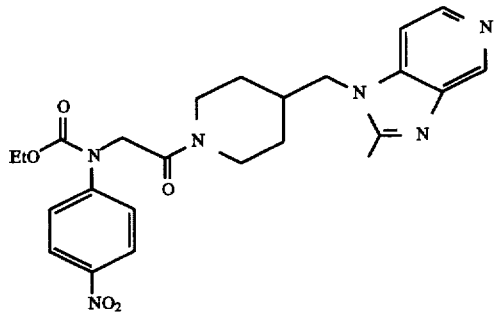
54
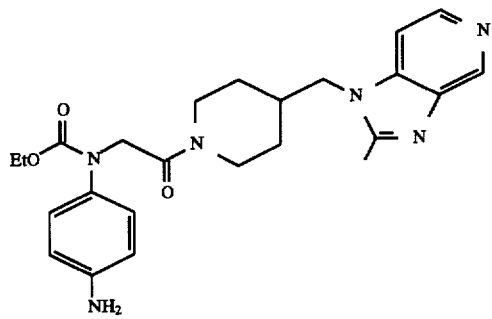
55
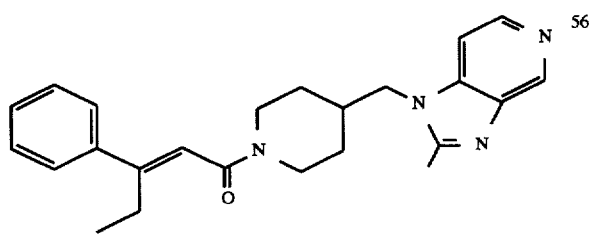
56
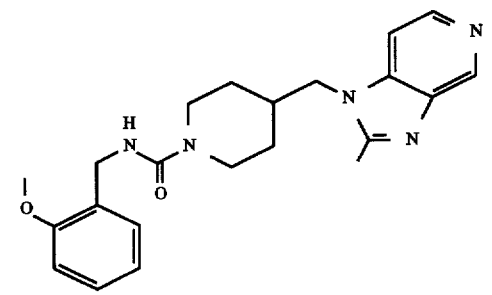
57
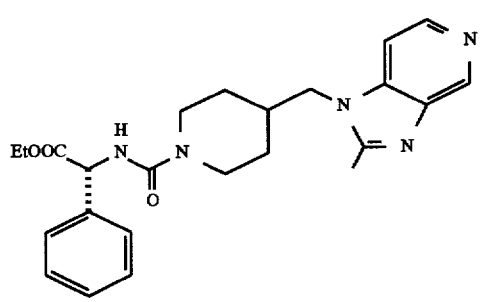
58
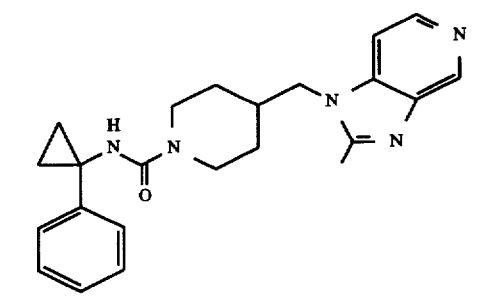
59
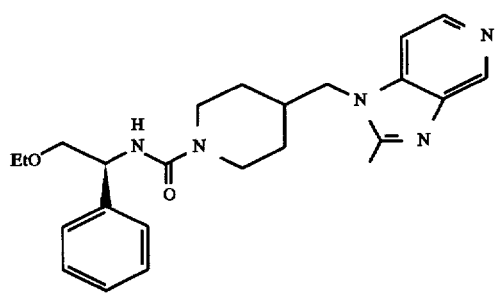
60
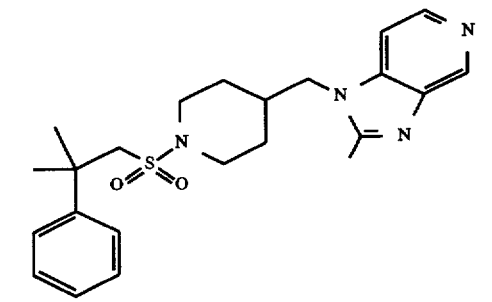
61
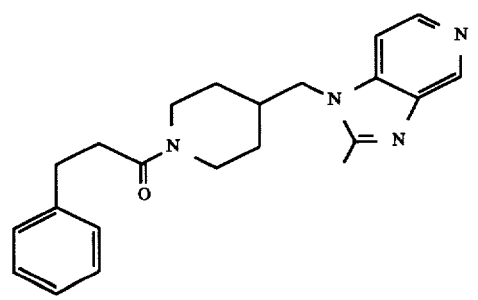
62
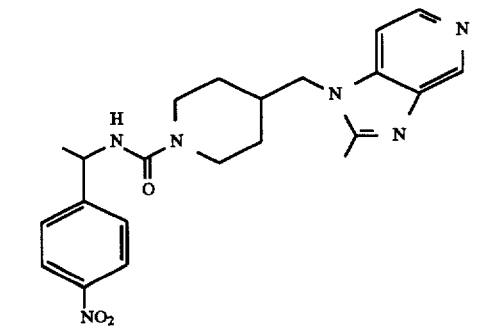
63

-continued
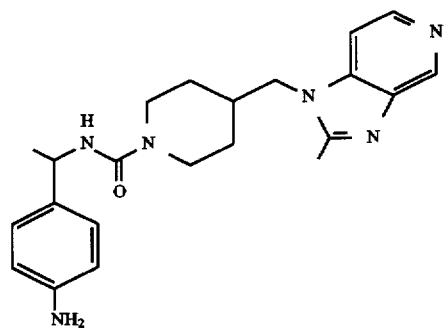
64
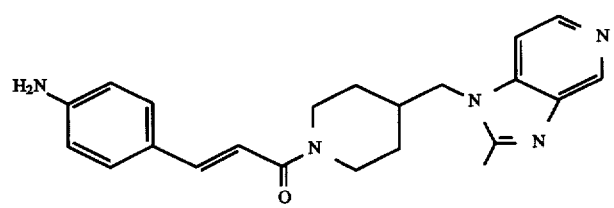
65
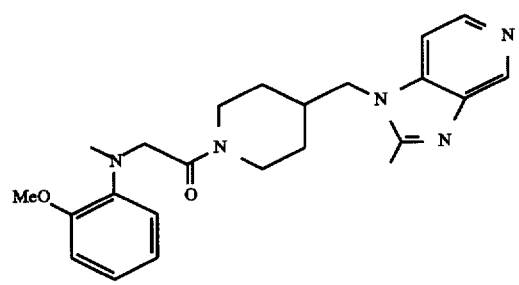
66
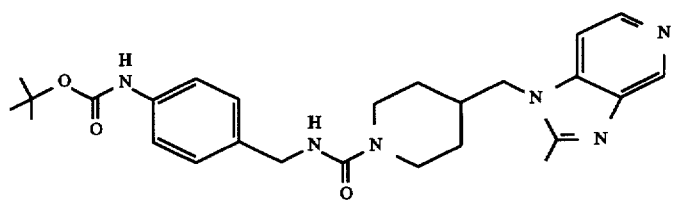
67
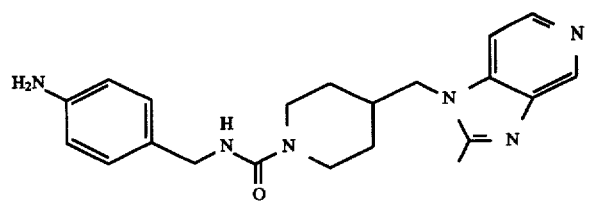
68
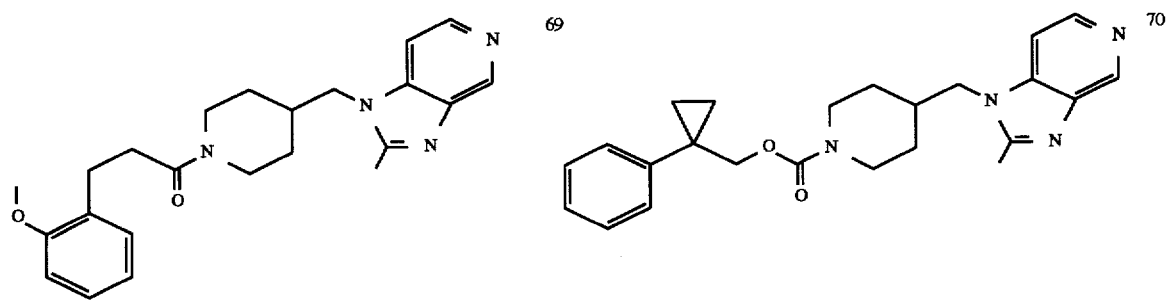
69
70

-continued
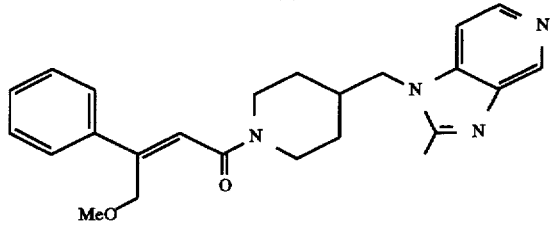
71
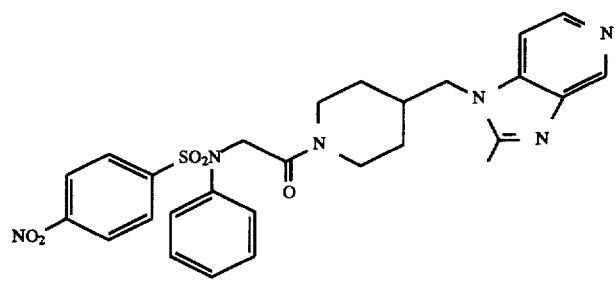
72
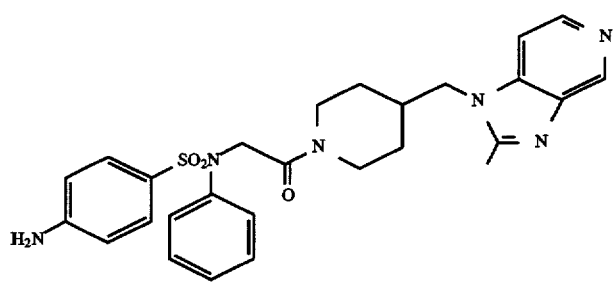
73
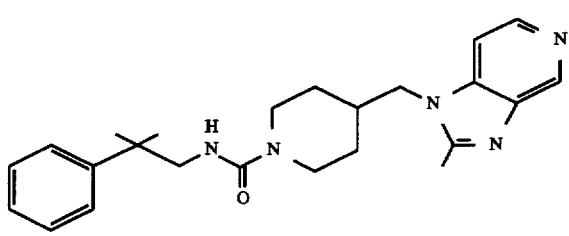
74
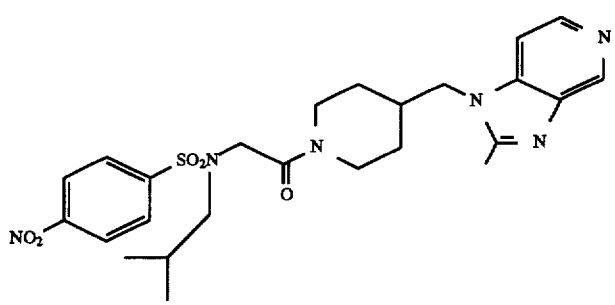
75
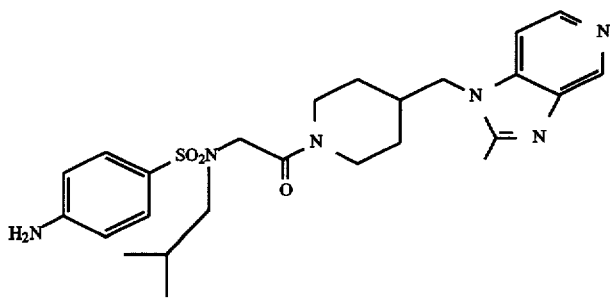
76

The compounds of formula I contain basic nitrogen atoms and, consequently, they can form salts with acids, which are also included in the present invention. There is no limitation on the nature of these salts, provided that, when used for therapeutic purposes, they are pharmaceutically acceptable, which, as is well-known in the art, means that they do not have reduced activity (or unacceptable reduced activity) or increased toxicity (or unacceptable increased toxicity) compared with the free compounds. Examples of these salts include: salts with an inorganic acid such as hydrochloric acid, hydrobromic acid, hydriodic acid, nitric acid, perchloric acid, sulfuric acid or phosphoric acid; and salts with an organic acid, such as methanesulfonic acid, trifluoromethanesulfonic acid, ethanesulfonic acid, benzenesulfonic acid, p-toluenesulfonic acid, fumaric acid, oxalic acid, maleic acid, citric acid, succinic acid, tartaric acid; and other mineral and carboxylic acids well known to those skilled in the art. The salts are prepared by reacting the free base with a sufficient amount of the desired acid to produce a salt in the conventional manner. Free bases and their salts differ in certain physical properties, such as solubility, but they are equivalent for the purposes of the invention.

The compounds of the present invention can exist in unsolvated as well as solvated forms, including hydrated forms. In general, the solvated forms, with pharmaceutically acceptable solvents such as water, ethanol and the like, are equivalent to the unsolvated forms for the purposes of the invention.

Some compounds of the present invention can exist as different diastereoisomers and/or optical isomers. Diastereoisomers can be separated by conventional techniques such as chromatography or fractional crystallization. The optical isomers can be resolved using any of the conventional techniques of optical resolution to give optically pure isomers. Such a resolution can be performed in any chiral synthetic intermediate as well as in the products of general formula I. The optical resolution techniques include separation by chromatography on a chiral phase or formation of a diastereoisomeric pair, resolution and subsequent recovery of the two enantiomers. The optically pure isomers can also be individually obtained using enantiospecific synthesis. The present invention covers both the individual isomers and their mixtures (e.g. racemic mixtures), whether as obtained by synthesis or by physically mixing them up.

Furthermore, some of the compounds of the present invention may present cis/trans isomery. The geometric isomers can be separated by conventional techniques such as chromatography or recrystallization. Such a separation can be performed either upon the products of formula I or upon any synthetic intermediate thereof. The individual isomers can also be obtained using stereospecific synthesis. The present invention covers each of the geometric isomers and the mixtures thereof.

The compounds of formula I may be prepared using the methods described below. It will be apparent to those skilled in the art that the precise method used for the preparation of a given compound may vary depending on its chemical structure. The reactions are performed in a solvent appropriate to the reagents and materials employed and suitable for the transformation being effected. Moreover, in some of the processes described below it will be desirable or necessary to protect reactive or labile groups using conventional protecting groups, for example the groups described below. Both the nature of these protecting groups and the procedures for their introduction and removal are well known in the art (see, e.g. Greene T. W., "Protective Groups in Organic Synthesis", John Wiley & Sons, New York, 1981).

The compounds of formula I can be obtained in general from amines of formula II by reaction with an acid chloride of formula BCOCl (VIII), a sulfonyl chloride of formula BSO$_2$Cl (IV), a compound of formula BOC(=O)G (V), a compound of formula BNHC(=O)G (VI) or a compound of formula BN=C=O (VII):

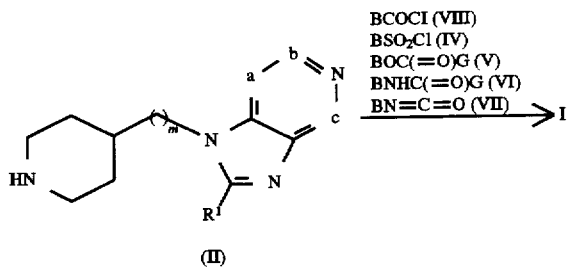

(II)

wherein B, a, b, c, m and R$^1$ have the previously described meaning and G represents a good leaving group such as chloro or —OPh. This reaction is carried out in the presence of a proton scavenger amine such as triethylamine or pyridine in a suitable solvent, or using the base as solvent. Examples of suitable solvents include halogenated hydrocarbons, such as dichloromethane and chloroform; ethers, such as diethyl ether, tetrahydrofuran and dioxane; and aromatic hydrocarbons, such as benzene and toluene. The reaction is carried out at a temperature preferably between 0° C. and the boiling point of the solvent. As an alternative to the acid chloride, the anhydride can be employed. Isocyanate derivatives of formula VII may have been previously prepared or may be generated in situ from the corresponding acid derivative of formula BCO$_2$H (III) by known procedures such as for example by treatment with diphenylphosphorylazide in the presence of triethylamine.

As it will be apparent to those skilled in the art, a compound of formula I wherein A represents —NHCO— may also be prepared by inverting the functionality of the reactive groups involved, i.e. by reacting an amine of formula BNH$_2$ (IX) with a reactive carbamate derivative of amine II, for example its phenylcarbamate derivative, which derivative can be prepared from amine II by conventional procedures such as treatment with phenyl chloroformate under standard conditions.

Alternatively, compounds of formula I wherein A represents —CO— can also be prepared by a dehydration procedure between amines of formula II and a carboxylic acid of formula BCOOH (III). This process can be carried out using any conventional reaction of amide bond formation, such as reacting an amine with an acid in the presence of an appropriate condensing agent such as a diimide, e.g. dicyclohexylcarbodiimide, alone or in combination with 1-hydroxybenzotriazole. This reaction is carried out in an inert solvent such as a halogenated hydrocarbon, for example dichloromethane or chloroform; an ether, for example tetrahydrofuran or dioxane; acetonitrile, or dimethylformamide. The reaction is carried out at a temperature preferably comprised between 0 and 60° C. during a reaction time preferably from 6 to 24 hours.

Moreover, a compound of formula I may also be obtained by interconversion from another compound of formula I.

Thus, for example, the compounds of formula I in which B represents a group of formula (i) wherein Z represents —NR$^6$C(=O)OR$^4$, —NR$^6$C(=O)R$^4$, —NR$^6$C(=O)NR$^4$R$^5$ or —NR$^6$SO$_2$R$^4$ or a group of formula (iii) wherein Y is different from hydrogen can be prepared from the corresponding compounds of formula I in which B represents a group of formula (i) wherein Z represents —NHR⁶ or a group of formula (iii) wherein Y=H, respectively, by conventional reactions, which are well known to those skilled in the art, as shown in Scheme 1. Examples thereof include alkylations, acylations, preparation of sulfonamides, carbamates and ureas. These reactions are widely described in the literature and are carried out in accordance with the usual conditions employed in organic chemistry for such transformations.

These compounds of formula I in which B represents a group of formula (i) wherein Z represents —NHR⁶ or a group of formula (iii) wherein Y=H can be prepared by the general procedures described above for the preparation of compounds I but starting from an acid of formula III (or the corresponding acid chloride or anhydride) or a sulfonyl chloride of formula IV wherein the amino group is blocked with an amino protecting group (P), as shown in Scheme 1. As amino protecting groups it is possible to use any amino protecting group known in the art, such as for example a tert-butoxycarbonyl group. In this case, it will be necessary a subsequent step for removing the protecting group in order to obtain a compound of formula I. Deprotection is carried out using conventional procedures, such as the procedures described below.

wherein a, b, c, $R^1$, $R^2$, $R^3$, $R^6$, $R^7$, m and n have the previously described meaning; A represents —CO— or —$SO_2$—; P represents an amino protecting group, such as a tert-butoxycarbonyl group and Q represents a group $CO_2H$ (thus giving rise to acids of formula III) or a group $SO_2Cl$ (thus giving rise to sulfonyl chlorides of formula IV).

Another example of interconversions between compounds of formula I is the reduction of a nitro group in a compound of formula I to an amino group. This reduction can be carried out by using any known reducing agent for aromatic nitro groups which is compatible with the other functional groups present in the molecule. Examples of suitable reducing agents include: Zn under a wide range of pH conditions in a suitable solvent such as ethanol-water mixtures at a temperature preferably between room temperature and that of the boiling point of the solvent, more preferably between 50° and 60° C.; $Na_2S_2O_4$ in a suitable solvent such as mixtures of water and an organic solvent, for example tetrahydrofuran, ethanol or pyridine; $SnCl_2$ under a wide range of pH conditions in a suitable organic solvent such as ethanol; Sn or Fe under a wide range of pH conditions; $NaBH_4$ in the presence of a suitable catalyst such as a Sn, Co or Pd salt in a suitable organic solvent such as ethanol; and formic acid or ammonium formate in the Scheme 1

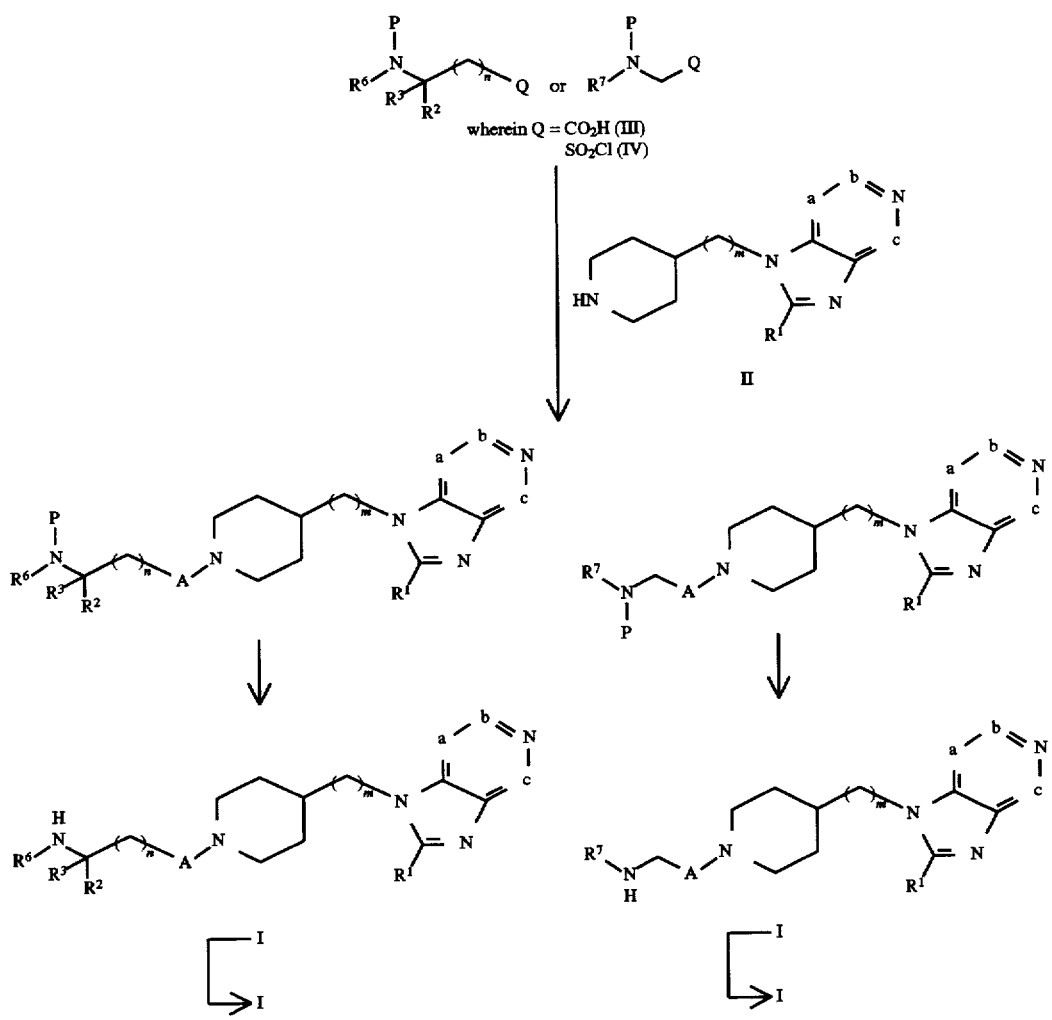

presence of Pd/C. Alternatively, the reduction can be carried out by hydrogenation in the presence of a catalyst such as palladium on carbon in a suitable solvent such as an alcohol at a temperature preferably between room temperature and that of the boiling point of the solvent, at a pressure preferably between atmospheric pressure and 10 atmospheres and during a reaction time preferably between 1 and 48 h.

As it will be appreciated by those skilled in the art, the interconversion of the substituents as described above can be effected either upon the final compounds of formula I or upon any synthetic intermediate thereof.

The salts of the compounds of formula I can be prepared by conventional procedures by treatment for example with an acid such as hydrochloric acid, sulfuric acid, nitric acid, oxalic acid or fumaric acid.

Amines of formula II can be prepared following the process described in Scheme 2, which is shown below:

alcohol at a temperature preferably between room temperature and that of the boiling point of the solvent, at a pressure preferably between atmospheric pressure and 10 atmospheres and during a reaction time preferably between 1 and 48 h. Alternatively, this reduction may be carried out using a suitable reducing agent such as $Na_2S_2O_4$ in a suitable solvent such as mixtures of water and an organic solvent, for example tetrahydrofuran, ethanol or pyridine.

In step C, a compound of formula XIII is allowed to react with an imino ether salt of formula $R^1C(=NH)OR^8HX$ (XV, wherein $R^1$ has the previously described meaning, $R^8$ represents $C_{1-6}$ alkyl and X represents halogen) in a suitable solvent such as an alcohol, for example ethanol, to give a compound of formula XIV. This reaction is carried out at a temperature preferably between room temperature and that of the boiling point of the solvent, during a reaction time preferably between 6 and 48 h. Alternatively, instead of an imino ether it is possible to use a carboxylic acid of formula

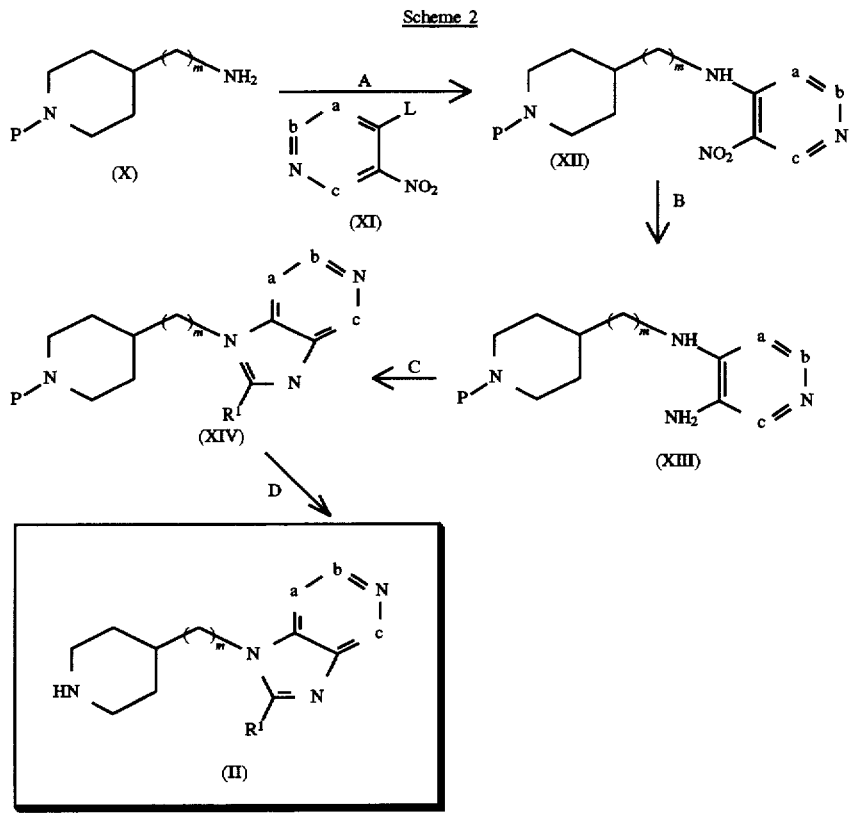

wherein a, b, c, m and $R^1$ have the previously described meaning; P represents an amino protecting group such as a tert-butoxycarbonyl group and L represents halogen or $C_{1-6}$ alkoxy.

In a first step (step A), a compound of formula X is allowed to react with a compound of formula XI in the presence of a proton scavenger amine such as triethylamine in a suitable solvent such as a halogenated hydrocarbon, for example chloroform, at a suitable temperature, preferably between room temperature and that of the boiling point of the solvent, to give a compound of formula XII.

The reduction of a compound of formula XII (step B) leads to a compound of formula XIII. This reduction can be carried out by hydrogenation in the presence of a catalyst such as palladium on carbon in a suitable solvent such as an $R^1COOH$ (XVI), an acid halide of formula $R^1COX$ (XVII), an anydride of formula $(R^1CO)_2O$ (XVIII) or a trialkylorthoester of formula $R^1C(OR^8)_3$ (XIX), wherein $R^1$, X and $R^8$ have the previously described meaning.

Finally, deprotection of the piperidinic nitrogen atom of a compound of formula XIV (step D) leads to a compound of formula II. The agent used for this deprotection and the reaction conditions employed will depend upon the nature of the protecting group present. Thus, if the protecting group is a tert-butoxycarbonyl group, deprotection can be carried out by treatment with an acid (for example an inorganic acid such as hydrochloric acid, phosphoric acid, sulfuric acid or the like or an organic acid such as toluenesulfonic acid, methanesulfonic acid, acetic acid, or trifluoroacetic acid) in a suitable solvent such as water, an alcohol (e.g. methanol), an ether (e.g. tetrahydrofuran or dioxane) or a halogenated hydrocarbon (e.g. dichloromethane), at a temperature preferably between 0° C. and room temperature.

The above reactions are all per se known ones and are carried out in accordance with the described procedures.

Acids of formula III and sulfonyl chlorides of formula IV are commercially available, widely described in the literature or can be prepared by procedures known to those skilled in the art, starting from commercially available products or products which have already been reported in the literature. Examples of these reactions include alkylations, acylations, conjugated additions to double bonds, Wittig reaction for the preparation of double bonds, preparation of sulfonamides, reductive aminations, and the like. All these reactions are known per se and are carried out in accordance with the reported conditions.

Compounds of formulae BOC(=O)G (V) and BNHC(=O)G (VI) can be readily prepared from the corresponding alcohols and amines of formulae BOH and $BNH_2$, respectively, by conventional procedures, for example by treatment with phenyl chloroformate.

Isocyanates of formula BN=C=O (VII) can be prepared from acids of formula BCOOH (III) using a sequence which comprises the following steps: conversion of the acid to an acylazide by treatment for example with diphenylphosphorylazide; and subsequent Curtius rearrangement of said acylazide to give an isocyanate. This sequence for preparing isocyanates from carboxylic acids is widely described in the literature and can be carried out in accordance with the reported conditions.

The compounds of formulae X, XI, XV, XVI, XVII, XVIII and XIX, as well as alcohols of formula BOH and amines of formula $BNH_2$ are commercially available, widely described in the literature or can be prepared by methods analogous to those known in the art starting from commercially available products.

Compounds of general formula I, being potent PAF antagonists, are useful as a preventive and therapeutic drugs for the treatment of circulatory diseases where PAF is involved, such as thrombosis, cerebral apoplexy (e.g. cerebral hemorrhage, cerebral thrombosis), angina pectoris, thrombotic phlebitis, thrombocitopenic purple, nephritis (e.g. glomerular nephritis), diabetic nephrosis, pancreatitis; ischemia and shock states (e.g. septic shock observed after severe infection or postoperatively, intravascular agglutination syndrome caused by endotoxin, anaphylactic shock, hemorrhagic shock, myocardial infarction); digestive tract diseases wherein PAF is involved (e.g. gastric ulcer, inflamatory bowel disease); diseases related to allergy and inflammation (e.g. asthma, dermatitis, urticaria, arthritis, psoriasis); pneumonia; rejection due to increased PAF production after implantations of organs; postoperative organodysfunction (e.g. in heart, liver and kidney) and any other condition in which PAF is implicated. They may also be used for contraception of female mammals by suppressing cell division and/or ovoimplantation on the uterus, in the treatment of endometriosis and in the prevention or treatment of hyperendothelinemia induced by excess secretion of endothelin.

According to the activity of the compounds disclosed, the present invention further provides compositions that comprise a compound of the invention together with an excipient and optionally other auxiliary agents, if necessary. The compounds of the present invention can be administered in different pharmaceutical preparations, the precise nature of which will depend, as it is well known, upon the chosen route of administration and the nature of the pathology to be treated.

Thus, solid compositions according to the present invention for oral administration include compressed tablets, dispersible powders, granules and capsules. In tablets, the active component is admixed with at least one inert diluent such as lactose, starch, mannitol, microcrystalline cellulose or calcium phosphate; granulating and disintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated tablets can be made with sugar, gelatin, hydroxypropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as ethoxylated saturated glycerides. Soft gelatin capsules are also possible, wherein the active ingredient is mixed with water or an oily medium, for example peanut oil, liquid paraffin or olive oil.

Dispersible powders and granules suitable for the preparation of a suspension by the addition of water provide the active ingredient in admixture with dispersing or wetting agents, suspending agents, such as sodium carboxymethylcellulose, methylcellulose, hydroxypropylmethyl-cellulose, sodium alginate, polyvinylpyrrolidone, gum tragacanth, xantham gum, gum acacia, and one or more preservatives, such as methyl or n-propyl-p-hydroxybenzoate. Additional excipients, for example sweetening, flavouring and colouring agents may also be present.

Liquid compositions for oral administration include emulsions, solutions, suspensions, syrups and elixirs containing commonly used inert diluents, such as distilled water, ethanol, sorbitol, glycerol, or propylene glycol. Such compositions may also comprise adjuvants such as wetting agents, suspending agents, sweetening, flavouring, perfuming, preserving agents and buffers.

Other compositions for oral administration include spray or aerosol compositions, which may be prepared by known methods. These compositions, which can disperse the active ingredient in the form of drops of a solution or suspension or in the form of a powder, will contain a suitable propellent.

Preparations for injection, according to the present invention, for parenteral administration by bolus injection or continuous infusion include sterile aqueous or non-aqueous solutions, suspensions or emulsions, in a non-toxic parentally-acceptable diluent or solvent. Examples of aqueous solvents or suspending media are distilled water for injection, Ringer's solution, and isotonic sodium chloride solution. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by any known method or manufactured in the form of sterile solid compositions which can be dissolved in sterile water or some other sterile injectable medium immediately before use. When all of the components are sterile, the injectables will maintain sterility if they are manufactured under a sterile environment.

A compound of the invention may also administered in the form of suppositories or enemas (which include aqueous or oily solutions as well as suspensions and emulsions) for rectal administration of the drug. Such compositions are prepared following conventional procedures; for example, suppositories can be prepared by mixing the active ingredient with a conventional suppository base such as cocoa butter or other glycerides.

Compositions for topical administration of a compound of the present invention include creams, ointments, pastes, lotions, gels, sprays, foams, aerosols, solutions, suspensions or powders. Such compositions are conventional formulations and can be prepared by procedures known in the art.

When the compounds of the present invention are to be administered to the eye, they can be formulated into solutions or suspensions in suitable sterile aqueous or non-aqueous solvents. These compositions may also include buffers and preservatives.

The dosage and frequency of dose may vary depending upon symptoms, age and body weight of the patient, as well as upon the route of administration, but, in general, the compounds of the invention may be administered orally in a daily dose of from 1–1000 mg for an adult, preferably a dosage from 5–250 mg, which may be administered either as a single dose or as divided doses. A preferred dosage for human patients is from 0.005 to 20 mg/kg of body weight, more preferably from 0.05 to 5 mg/kg of body weight.

The compositions for topical administration will typically contain 0.5–10% by weight of a compound of formula I.

Following are some representative preparations for tablets, capsules, syrups, aerosols, injectables and creams. They can be prepared following standard procedures and they are useful in the treatment of PAF-mediated conditions.

| Tablets | |
|---|---|
| Compound of formula I | 100 mg |
| Dibasic calcium phosphate | 125 mg |
| Sodium starch glycolate | 10 mg |
| Talc | 12.5 mg |
| Magnesium stearate | 2.5 mg |
| | 250.0 mg |

| Hard gelatin capsules | |
|---|---|
| Compound of formula I | 100 mg |
| Lactose | 197 mg |
| Magnesium stearate | 3 mg |
| | 300 mg |

| Syrup | |
|---|---|
| Compound of formula I | 0.4 g |
| Sucrose | 45 g |
| Flavouring agent | 0.2 g |
| Sweetening agent | 0.1 g |
| Water to | 100 mL |

| Aerosol | |
|---|---|
| Compound of formula I | 4 g |
| Flavouring agent | 0.2 g |
| Propylene glycol to | 100 ml |
| Suitable propellent to | 1 unit |

| Injectable preparation | |
|---|---|
| Compound of formula I | 100 mg |
| Benzylic alcohol | 0.05 ml |
| Propylene glycol | 1 ml |
| Water to | 5 ml |

| Cream | |
|---|---|
| Compound of formula 1 | 2 g |
| Dimethyl acetamide | 2 g |
| White paraffin | 25 g |
| Stearic alcohol | 22 g |

| -continued | |
|---|---|
| Propylene glycol | 12 g |
| Sodium lauryl sulfate | 1.5 g |
| Methylparabene | 0.3 g |
| Purified water | 31.6 g |

The following pharmacological tests explain the activity of the compounds of the present invention in more detail.

PHARMACOLOGICAL TEST 1

Inhibition of Platelet Aggregation Induced by PAF.

Platelet aggregation studies were done by the method of Born (J. Physiol., 1962, 162, 67). Blood was collected in 3.16% sodium citrate (1 volume per 9 volumes of blood) by cardiac puncture from male New Zealand rabbits (2–2.5 Kg body weight). Platelet rich plasma (PRP) was prepared by centrifuging the blood at 250 xg for 10 min. at 4° C. The PRP was diluted with platelet-poor plasma (PPP) obtained by further centrifuging at 3000 xg for 10 min. The platelet count was adjusted to $3 \times 10^5$ cells/mm$^3$. Platelet aggregation was induced by $C_{18}$-PAF (15 nM) and measured with a dual-channel aggregometer Chrono-log 560. Activity was expressed as the $IC_{50}$ value, that is to say the concentration of drug required to inhibit platelet aggregatory response by 50%. The results are shown in table I below.

TABLE I

| Compound No. | $IC_{50}$ (µM) |
|---|---|
| 1 | 0.0076 |
| 16 | 0.0092 |
| 17a | 0.018 |
| 17b | 0.0050 |
| 21 | 0.0069 |
| 23 | 0.011 |
| 32 | 0.011 |
| 39 | 0.016 |
| 40 | 0.012 |
| 41 | 0.0067 |
| 44 | 0.019 |
| 47 | 0.036 |
| 50 | 0.013 |
| 59 | 0.017 |
| 60 | 0.017 |
| 61 | 0.0062 |
| 70 | 0.034 |

PHARMACOLOGICAL TEST 2

Inhibition of PAF-induced Hypotension in Normotensive Rats.

Male Sprague-Dawley rats, weighing 180–220 g, were anesthetized with sodium pentobarbital (50 mg/Kg i.p.). Blood pressure was recorded from the left carotid artery using a Statham pressure transducer coupled to a Beckman R611 recorder. Right and left fernoral veins were catheterized to inject test compounds and PAF (0.5 µg/Kg). Test compounds were administered by intravenous injection (1 mL/Kg, dissolved in saline) 3 min. before PAF. Blood pressure was monitored and percent inhibition of PAF-induced hypotension with respect to controls was calculated. The results were expressed as $ID_{50}$ values, that is to say the dose of test compound required to inhibit hypotension by 50%. Results are shown in Table II.

TABLE II

| Compound No. | ID$_{50}$ (mg/Kg) |
| --- | --- |
| 1 | 0.0086 |
| 17a | 0.029 |
| 17b | 0.01–0.025 |
| 21 | 0.043 |
| 30 | 0.015 |
| 32 | 0.0079 |
| 40 | 0.033 |
| 41 | 0.012 |
| 47 | 0.013 |
| 50 | 0.017 |
| 59 | 0.021 |
| 60 | 0.019 |
| 70 | 0.014 |

The following examples illustrate, but do not limit, the scope of the present invention:

REFERENCE EXAMPLE 1

1-tert-Butoxycarbonyl-4-(aminomethyl)piperidine

To a cooled (0° C.) solution of 4-(aminomethyl)piperidine (40 g, 0.35 mol) in CHCl$_3$ (300 mL) was added a solution of di-tert-butyl dicarbonate (39.2 g, 0.17 mol) in CHCl$_3$ (300 mL) and the reaction mixture was stirred at room temperature for 18 h. The resulting solution was washed with H$_2$O and the aqueous phase was reextracted with CHCl$_3$. The combined organic phases were dried and concentrated to a crude product (54.1 g), which was directly used in the next step as obtained.

$^1$H NMR (80 MHz, CDCl$_3$) δ (TMS): 4.11 (broad d, J=13.4 Hz, 2H), 2.69 (m, 4H), 1.45 (s, 9H), 1.8–0.8 (complex signal, 7H).

REFERENCE EXAMPLE 2

4-[[1-(tert-Butoxycarbonyl)-4-piperidyl]methylamino]-3-nitropyridine

To a cooled (0° C.) solution of 4-chloro-3-nitropyridine (83.7 g, 0.53 mol) in CHCl$_3$ (700 mL) a solution of the product obtained in reference example 1 (140 g, 0.65 mol) and Et$_3$N (110 mL) in CHCl$_3$ (500 mL) was added and the mixture heated at reflux for 18 h. It was then evaporated, and the residue was partitioned between 1N NaOH and EtOAc. The aqueous phase was reextracted twice with EtOAc, and the combined organic extracts were dried and concentrated to a total volume of 400 mL. After cooling (–20° C.) overnight, a yellow solid was collected and dried (115 g, 64%).

mp 131°–138° C.;

$^1$H NMR (80 MHz, CDCl$_3$) δ (TMS): 9.20 (s, 1H), 8.30 (d, J=5.5 Hz, 1H), 8.19 (m, 1H), 6.72 (d, J=5.5 Hz, 1H), 4.18 (broad d, J=13.4 Hz, 2H), 3.26 (t, J=5.9 Hz, 2H,) 2.72 (broad t, J=12.7 Hz, 2H), 1.46 (s, 9H), 1.8–0.8 (complex signal, 5H).

REFERENCE EXAMPLE 3

3-Amino-4-[[1-(tert-butoxycarbonyl)-4-piperidyl]methylamino]pyridine

A mixture of the product obtained in reference example 2 (26.2 g, 0.077 mol) and Pd/C 10% (3.83 g) in MeOH (500 mL) was hydrogenated at atmospheric pressure for 18 h. The catalyst was filtered off and the flitrate concentrated to a crude product (22.9 g, 96%), which was directly used in the next step as obtained.

$^1$H NMR (80 MHz, CDCl$_3$) δ (TMS): 7.65 (d, J=5.5 Hz, 1H), 7.64 (s, 1H), 6.59 (d, J=5.5 Hz, 1H), 4.10 (broad d, J=13.4 Hz, 2H), 3.9 (s, 3H), 3.25 (d, J=6.5 Hz, 2H), 2.74 (broad t, J=12.0 Hz, 2H), 1.46 (s, 9H), 1.8–0.8 (complex signal, 5H).

Alternatively, the title compound was prepared as follows: To a solution of the product obtained in reference example 2 (82.2 g, 0.244 mol) in pyridine (400 mL) was added a solution of Na$_2$S$_2$O$_4$ (170 g, 0.976 mol) in H$_2$O (500 mL). The mixture was stirred at room temperature for 24 h, then partitioned between EtOAc (800 mL) and 5N NaOH (450 mL). The organic phase was separated, dried and evaporated to give a yellow solid (101 g), which still contained pyridine.

REFERENCE EXAMPLE 4

1-[[1-(tert-Butoxycarbonyl)-4-piperidyl]methyl]-1H-2-methylimidazo[4,5-c]pyridine To a solution of the product obtained in reference example 3 (22.9 g, 0.07 mol) in EtOH (350 mL) was added ethyl acetimidate hydrochloride (9.2 g, 0.074 mol) and the mixture was refluxed for 4 h. A second equivalent of ethyl acetimidate hydrochloride was added (9.2 g, 0.074 mol) and the mixture was further refluxed for 18 h. Finally, a third equivalent of ethyl acetimidate hydrochloride was added (9.2 g, 0.074 mol) and the mixture was heated for 4 h more. The solvent was removed in vacuo and the residue partitioned between CHCl$_3$ and 0.5N NaOH. The organic phase was dried and concentrated to a residue (30 g), which was purified by chromatography on silica gel (CHCl$_3$:MeOH, 10%) to afford the title compound as a yellow solid (23.4 g, 95%).

$^1$H NMR (80 MHz, CDCl$_3$) δ (TMS): 8.98 (s, 1H), 8.38 (d, J=5.5 Hz, 1H), 7.22 (d, J=5.5 Hz, 1H), 4.10 (broad d, J=13.4 Hz, 2H), 3.96 (d, J=7.3 Hz, 2H), 2.64 (broad t, J=12.7 Hz, 2H), 2.63 (s, 3H), 1.46 (s, 9H), 2.2–1.0 (complex signal, 5H).

REFERENCE EXAMPLE 5

1-[(4-Piperidyl)methyl]-1H-2-methylimidazo[4,5-c]pyridine

To a cooled (0° C.) solution of the product obtained in reference example 4 (23.1 g, 0.07 mol) in MeOH (200 mL) was added dropwise 6.5N HCl(g)/dioxane solution (44 mL). The mixture was stirred at room temperature for 2 h and evaporated to dryness. The residue was cooled (0° C.), 1N NaOH was added and the resulting solution was extracted with CHCl$_3$ (3×). The combined organic extracts were dried and concentrated to a yellow solid (15.8 g, 98%).

$^1$H NMR (80 MHz, CDCl$_3$) δ (TMS): 8.96 (s, 1H), 8.35 (d, J=5.5 Hz, 1H), 7.20 (d, J=5.5 Hz, 1H), 3.95 (d, J=7.3 Hz, 2H), 3.06 (broad d, J=12.0 Hz, 2H), 2.61 (s, 3H) 2.51 (broad t, J=12.7 Hz, 2H), 2.2–1.0 (complex signal, 6H).

REFERENCE EXAMPLE 6

1-(4-Piperidyl)-1H-2-methylimidazo[4,5-c]pyridine, hydrochloride

Following the procedure described above in reference examples 1–5, but starting from 4-aminopiperidine instead of 4-(aminomethyl)piperidine, the title compound was obtained (56%).

$^1$H NMR (80 MHz, CD$_3$OD) δ (TMS): 9.32 (s, 1H), 8.82 (d, J=5.5 Hz, 1H), 8.62 (d, J=5.5 Hz, 1H), 5.17 (s, 1H), 3.9–2.2 (complex signal, 9H).

REFERENCE EXAMPLE 7

3,3-Diphenyl-3-ethoxycarbonylpropionic acid a) Ethyl diphenylacetate

To a solution of diphenylacetic acid (20 g, 0.094 mol) in EtOH (70 mL), was added toluene (70 mL). Next, H$_2$SO$_4$ (3 mL) was added dropwise and the reaction mixture was refluxed for 18 h. Then, H$_2$O and EtOAc were added, the layers were separated, and the organic phase was washed with saturated NaHCO$_3$ solution (3×), dried and concentrated to a white solid (23.2 g), which was directly used in the next step as obtained.

$^1$H NMR (80 MHz, CDCl$_3$) δ (TMS): 7.28 (m, 10H), 5.00 (s, 1H), 4.19 (q, J=7Hz, 2H), 1.22 (t, J=7 Hz, 3H).

b) Tert-butyl 3,3-diphenyl-3-ethoxycarbonylpropionate

To a solution of NaH (60% suspension in parafine, 4.25 g) in DMF (100 mL), was added a solution of the product obtained in reference example 7a (23.2 g, 0.965 mol) in DMF (50 mL) and the reaction mixture was stirred at room temperature for 1 h. Tert-butyl bromoacetate (13.5 mL, 0.965 mol) was added dropwise and the mixture was stirred at 60° C. for 18 h. The resulting solution was treated with H$_2$O (1 mL) and the solvents were removed. More H$_2$O was added and then it was extracted with EtOAc, at basic pH. The organic phase was dried and concentrated to a dark oil.

$^1$H NMR (80 MHz, CDCl$_3$) δ (TMS): 7.26 (s, 10H), 4.21 (q, J=7.2 Hz, 2H), 3.43 (s, 2H), 1.30 (s, 9H), 1.16 (t, I=7.2 Hz, 3H).

c) Title compound

To a cooled (0° C.) solution of the product obtained in reference example 7b (6 g, 0.017 mol) in CH$_2$Cl$_2$ (20 mL) was added dropwise trifluoroacetic acid (2.6 mL) and the mixture was stirred at room temperature for 18 h. The title compound was then obtained by evaporating the resulting solution to dryness (85%).

$^1$H NMR (80 MHz, CDCl$_3$) δ (TMS): 11.26 (broad s, 1H), 7.25 (s, 10H), 4.21 (q, J=7.1 Hz, 2H), 3.54 (s, 2H), 1.17 (t, J=7.1 Hz, 3H).

REFERENCE EXAMPLE 8

3-Phenyl-3-(phenylamino)propionic acid

To a solution of aniline hydrochloride (3.37 g, 26 mmol) and ethyl benzoylacetate (5 mL, 26 mmol) in MeOH (70 mL) was added NaBH$_3$CN (1.75 g) and the mixture was stirred at room temperature for 18 h. The solvent was removed and the residue partitioned between 0.5N HCl and Et$_2$O. The aqueous phase was made basic with 1N NaOH and extracted with CHCl$_3$. The organic phase was dried and concentrated to a residue. Purification by chromatography on silica gel (hexane: EtOAc, 5%) afforded ethyl 3-phenyl-3-(phenylamino)propionate (4.3 g, 62%). This compound was then hydrolized under basic conditions to give the title compound as a white solid.

mp: 110–°111° C.;

$^1$H NMR (80 MHz, CDCl$_3$) δ (TMS) 7.10 (m, 8H), 6.63 (m, 2H), 4.85 (t, J=6.3 Hz, 1H), 4.05 (m, 2H), 2.85 (d, J=6.5 Hz, 2H).

REFERENCE EXAMPLE 9

3-(4-Nitrophenyl)amino-3-phenylpropionic acid

A mixture of trans-cinnamic acid (2 g, 13 mmol) and HBr (30% solution in AcOH, 40 mL) was stirred at room temperature for 18 h and then evaporated to dryness. The resulting solid was taken upin 2-butanone (100 mL) and p-nitroaniline (5 g, 36 mmol) was added. The reaction mixture was refluxed for 18 h, allowed to cool and partitioned between CHCl$_3$ and 1N HCl. The organic phase was dried and concentrated to a residue. This was purified by chromatography on silica gel (hexane: EtOAc, 50%), to afford the title compound as a yellow solid (0.78 g, 21%).

$^1$H NMR (80 MHz, CDCl$_3$) δ (TMS) 7.99 (d, J=9.2 Hz, 2H), 7.33 (m, 5H), 6.56 (d, J=9.2 Hz, 2H), 4.92 (t, J=6.3 Hz, 1H), 3.44 (m, 2H), 2.82 (d, J=6.5 Hz,

REFERENCE EXAMPLE 10a and 10b cis- and trans-3-(4-Nitrophenyl)-3-phenylpropenoic acid To a cooled (0° C.) suspension of 50% NaH (24.66 g, 0.51 mol) in THF (375 mL) was added dropwise triethyl phosphonoacetate (88.2 mL, 0.44 mol). The mixture was stirred for 45 min and 4-nitrobenzophenone (102 g, 0.45 mol) in THF (525 mL) was added. The resulting mixture was refluxed for 18 h under an argon atmosphere, and then allowed to cool and partitioned between H$_2$O and EtOAc. The organic phase was dried and concentrated to a residue (115 g). This crude material was dissolved in MeOH (600 mL), a solution of K$_2$CO$_3$ (87.2 g) in H$_2$O (288 mL) was added and the mixture was refluxed for 4 h. MeOH was removed, water was added and the solution extracted with hexane. The aqueous solution was then brought up to acid pH with 5N HCl and extracted with CHCl$_3$. Evaporation of the solvent afforded a brown solid as a ds/trans mixture.

Pure cis isomer (10a) can be obtained by recrystallization from EtOAc (34 g, 30%).

$^1$H NMR (80 MHz, CDCl$_3$) δ (TMS): 8.23 (d, J=8.0 Hz, 2H), 7.33 (m, 7H), 6.70 (m), 6.44 (s, 1H).

Pure trans isomer (10b) can be obtained as follows: A mixture of ethyl trans-cinnamate (4.4g, 27 mmol), 4-bromonitrobenzene (6 g, 29.7 mol), triphenylphosphine (0.26 g), tributylamine (8 mL), and palladium acetate (57 mg) in acetonitrile (20 mL) was heated under argon at reflux for two days. The cooled mixture was partitioned between 0.5N NaOH and CHCl$_3$, the organic phase separated, dried and concentrated. The residue was purified by chromatography on silica gel (Hexane:EtOAc, 20%) to afford a white solid (2.4 g, 31%).

$^1$H NMR (80 MHz, CDCl$_3$) δ (TMS): 8.18 (d, J=8.0 Hz, 2H), 7.33 (m, 8H), 6.39 (s, 1H).

REFERENCE EXAMPLE 11

3-Hydroxy-3-phenyl-3-trifluoromethylpropionic acid

To a cooled (0° C.) solution of n-butyl lithium (1.6M in hexanes, 40 mL) in dry THF (90 mL), was added dropwise diisopropylamine (9.45 mL) and the mixture was stirred for 5 min. Keeping the temperature at 0° C., AcOH (1.92 mL, 0.0336 mol) was added dropwise and the reaction mixture was stirred for 10 min and then heated at 50° C. for 30 min. The resulting solution was allowed to cool, a solution of 2,2,2-trifluoroacetophenone (4.76 mL (0.0336 mol) in dry THF (15 mL) was added at 0° C. and the resulting mixture was stirred at room temperature overnight. Finally, Et$_2$O (150 mL) and H$_2$O (50 mL) were added, the aqueous phase was separated, acidified with HCl and extracted with EtOAc (3×). The organic phase was dried and concentrated to afford the title compound as an orange solid (3.88 g, 49%).

$^1$H NMR (80 MHz, CDCl$_3$) δ (TMS): 9.0 (complex signal, 2H), 7.38 (m, 5H), 3.2 (s, 2H).

REFERENCE EXAMPLE 12

3,3-Diphenylpropenoic acid

Following a similar procedure to that described in reference example 10, but using benzophenone instead of 4-nitrobenzophenone, the title compound was obtained.

$^1$H NMR (80 MHz, CDCl$_3$) δ (TMS): 7.31 (m, 10H), 6.33 (s, 1H), 5.9 (m, 1H).

REFERENCE EXAMPLE 13

3-(4-Nitrophenyl)butanoic acid

To cooled (0° C.) concentrated H$_2$SO$_4$ (30 mL) was added 3-phenylbutyric add (15 g, 91 mmol). Then, a cooled solution of HNO$_3$ (5 mL) in H$_2$SO$_4$ (10 mL) was added dropwise and the mixture was stirred at 0° C. for 30 min and then at room temperature for 30 min more. The mixture was poured into ice and the resulting solution allowed to stand in the refrigerator overnight. The precipitate was filtered, washed with H$_2$O and dried to give a crude product (28.3 g). This was purified by chromatography on silica gel (CHCl$_3$:MeOH, 10%) to afford the title compound (4.1 g, 21%).

$^1$H NMR (80 MHz, CDCl$_3$+CD3OD) δ (TMS): 8.14 (d, J=8.7 Hz, 2H), 7.47 (d, J=8.7 Hz, 2H), 4.77 (s, 1H, 3.36 (quint, J=7.6 Hz, 1H), 2.61 (d, J=7.4 Hz, 2H), 1.31 (d, J=7.0 Hz, 3H).

REFERENCE EXAMPLE 14

3-Ethoxycarbonyl-3-(4-nitrophenyl)propionic acid

Following a similar procedure to that described in reference example 7b, but starting fromethyl 4-nitrophenylacetate instead of ethyl diphenylacetate, and hydrolizing then the tert-butyl ester using p-toluenesulfonic acid in benzene at reflux instead of using trifluoroacetic acid, the title compound was obtained.

$^1$H NMR (80 MHz, CDCl$_3$) δ (TMS): 9.61 (s, 1H), 8.19 (d, J=8.4 Hz, 2H), 7.49 (d, J=8.4 Hz, 2H), 4.16 (q, J=7.3 Hz, 2H), 4.14 (m, 1H), 3.30 (dd, J=17.5 Hz, J=1H), 2.76 (dd, J=17.3 Hz, J=6.1 Hz, 1H), 1.20 (t, J=7.3 Hz, 3H).

REFERENCE EXAMPLE 15

3-Ethoxycarbonyl-3-phenylpropionic acid

Following a similar procedure to that described in reference example 14, but starting fromethyl phenylacetate, the title compound was obtained.

$^1$H NMR (80MHz, CDCl$_3$) δ (TMS): 9.49 (m, 1H), 7.28 (s, 5H), 4.13 (m, 3H), 3.25 (dd, J=17.2 Hz, J=9.8 Hz, 1H), 2.67 (dd, J=17.1 Hz, J=5.3 Hz, 1H), 1.17 (t, J=Hz, 3H).

REFERENCE EXAMPLE 16 cis and trans-3-(3-Nitrophenyl)-3-phenylpropenoic acid

Following the procedure described in reference example 10, but starting from 3-nitrobenzophenone, the title compound was obtained as a yellow solid.

$^1$H NMR (80 MHz, CDCl$_3$) δ (TMS): 8.11 (m, 2H), 7.25 (m, 7H), 6.37 (s, 0.67H), 6.34 (s, 0.33H), 6.12 (s, 1H).

REFERENCE EXAMPLE 17

3-[N-(Ethoxycarbonyl)amino]-3-(4-nitrophenyl)propionic acid

Following the procedure described in reference example 13, but starting from 3-[N-(ethoxycarbonyl)amino]-3-phenylpropionic acid, the title compound was obtained.

$^1$H NMR (80 MHz, CDCl$_3$) δ (TMS): 9.66 (s, 1H), 8.17 (d, J=6.5 Hz, 2H), 7.50 (d, J=6.5 Hz, 2H), 6.2 (m, 1H), 5.22 (q, J=7.5 Hz, 1H), 4.11 (q, J=7.1 Hz, 2.91 (d, J=6.2 Hz, 2H), 1.20 (t, J=7.1 Hz, 3H).

REFERENCE EXAMPLE 18

3-Hydroxy-3-(2-methylpropyl)-5-methylhexanoic acid

Following the procedure described in reference example 11, but using 2,6-dimethyl-4-heptanone instead of 2,2,2-trifluoroacetophenone, the title compound was obtained (56%).

$^1$H NMR (80MHz, CDCl$_3$) δ (TMS): 6.8 (m, 2H), 2.25 (s, 2H), 1.7 (m, 2H), 0.95 (m, 16H).

REFERENCE EXAMPLE 19

3-Methyl-3-phenylbutanoic acid a) 3-Methyl-3-phenylbutyronitrile

A mixture of 1-chloro-2-methyl-2-phenylpropane (150 g, 0.889 mol) and NaCN (54.46 g) in DMSO (250 mL) was heated at 100° C. for 3 weeks. The solution was concentrated to half the initial volume. H$_2$O (400 mL) was added and it was extracted with Et$_2$O (3×). The combined organic extracts were dried and concentrated to a crude product (115.1 g), which was directly used in the next step as obtained.

b) Title compound

To the product obtained in a) above was added slowly H$_2$O (375 mL) and H$_2$SO$_4$ (300 mL), and the mixture was refluxed for 48 h. Then, H$_2$O was added and the resulting solution was extracted with CHCl$_3$. The organic phase was washed with 2N NaOH (3×), and the aqueous phase was acidified with 5N HCl and extracted with CHCl$_3$. The combined organic extracts were dried and concentrated to afford the title compound.

$^1$H NMR (80 MHz, CDCl$_3$) δ (TMS): 10.8 (m, 1H), 7.29 (s, 5H), 2.61 (s, 2H), 1.43 (s, 6H).

REFERENCE EXAMPLE 20

N-Methyl-N-phenylaminoacetic acid

To a solution of N-phenylglycine (5 g, 33 mmol) and formaldehyde (37% aqueous solution, 20 mL) in acetonitrile (100 mL) was added NaBH$_3$CN (6.8 g) and AcOH (2 mL) and the reaction mixture was stirred at room temperature overnight. Volatiles were removed in vacuo, the residue was acidified to pH=3–4 and extracted with CHCl$_3$ several times. The combined organic extracts were dried and concentrated to afford a crude product (5.73 g), which was purified by chromatography on silica gel (EtOAc) to afford the title compound (3.96 g, 73%).

$^1$H NMR (80 MHz, CDCl$_3$) δ (TMS): 8.82 (s, 1H), 7.38 (m, 2H), 6.75 (m, 3H), 4.05 (s, 2H), 3.03 (s, 3H).

REFERENCE EXAMPLE 21

3-Methyl-3-(4-nitrophenyl)butanoic acid

Following the procedure described in reference example 13, but starting from the compound obtained in reference example 19, the title compound was obtained (47%).

$^1$NMR (80 MHz, CDCl$_3$) δ (TMS): 8.16 (d, J=6.5 Hz, 2H), 7.55 (d, J=6.5 Hz, 2H), 3.5 (m, 1H), 2.70 (s, 2H), 1.50 (s, 6H).

REFERENCE EXAMPLE 22 cis and trans-3-(4-Nitrophenyl)-2-butenoic acid

Following the procedure described in reference example 10, but using 4-nitroacetophenone instead of 4-nitrobenzophenone, the title compound was obtained.

$^1$H NMR (80 MHz, CDCl$_3$) δ (TMS): 8.8 (m, 1H), 8.23 (d, J=6.4 Hz, 2H), 7.64 (d, J=6.4 Hz, 2H), 6.21 (d, J=1.3 Hz, 0.7H), 6.07 (d, J=1.3 Hz, 0.3H), 2.62 (d, J=1.3 Hz, 3H).

REFERENCE EXAMPLE 23

N-Ethoxycarbonyl-N-(4-nitrophenyl)aminoacetic acid

To a cooled (0° C.) suspension of 4-nitroaniline (10 g, 0.072 mol) and Et$_3$N (10 mL) in CHCl$_3$ (120 mL), was added dropwise ethyl chloroformate (6.9 mL) and the mixture was stirred under an argon atmosphere at room temperature overnight. CHCl$_3$ was added and the resulting solution was washed with 1N HCl. The layers were separated, the aqueous phase was washed with CHCl$_3$ and the combined organic extracts were dried and concentrated. The residue was chromatographed on silica gel (hexane:EtOAc, 30%) to afford N-(ethoxycarbonyl)-4-nitroaniline (1.7 g).

This product was dissolved in THF (5 mL) and was then added dropwise to a cooled (0° C.) suspension of NaH (0.48 g, 10 mmol) in dry THF (10 mL). The mixture was stirred at room temperature for 30 min and then ethyl bromoacetate (0.89 mL, 8 mmol) was added. The reaction mixture was stirred at room temperature for 48 h and then refluxed for 24 h. The residue was taken upin CHCl$_3$ and phosphate buffer, and extracted with CHCl$_3$ (2×). Evaporation of the solvent gave the title compound as the ethyl ester (1.54 g).

This product was dissolved in MeOH (35 mL), a solution of K$_2$CO$_3$ (1.33 g) in H$_2$O (18 mL) was added and the mixture was refluxed for 3 h. Volatiles were removed in vacuo and the resulting solution was extracted with hexane. The aqueous phase was made acid and extracted with CHCl$_3$. The organic extracts were dried and concentrated to afford the title compound.

$^1$H NMR (80 MHz, CDCl$_3$) δ (TMS): 8.21 (d, J=6.5 Hz, 2H), 7.50 (d, J=6.5 Hz, 2H), 5.89 (broad s, 1H), 4.45 (s, 2H), 4.16 (q, J=7.1 Hz, 2H), 1.26 (t, J=7.1 Hz,

REFERENCE EXAMPLE 24 trans-3-Phenyl-2-pentenoic acid

Following the procedure described in reference example 10, but using propiophenone instead of 4-nitrobenzophenone, the title compound was obtained.

$^1$H NMR (80MHz, CDCl$_3$) δ (TMS): 10.68 (m, 1H), 7.42 (m, 5H), 6.05 (s, 1H), 3.12 (q, J=7.1 Hz, 2H), 1.09 (t, J=7.1 Hz, 3H).

REFERENCE EXAMPLE 25

2-Methyl-2-phenylpropylsulfonyl chloride

In a flask under argon were placed magnesium turnings (0.8 g, 0.036 mol), dry THF (10 mL) and a iodine crystal. Then, 1-chloro-2-methyl-2-phenylpropane (5 mL, 0.031 mol) in THF (15 mL) was added slowly and the reaction mixture was refluxed for 30 min. It was then allowed to cool to room temperature and finally it was cooled to −70° C. and sulfuryl chloride (2.5 mL, 0.031 mol) in THF (10 mL) was added dropwise. The reaction was allowed to warm up to room temperature and was stirred at this temperature overnight. The resulting solution was poured into diluted phosphate buffer and extracted with EtOAc (3×). Evaporation of the solvent afforded the title compound (4.6 g, 65%).

$^1$H NMR (80 MHz, CDCl$_3$) δ (TMS): 7.30 (m, 5H), 3.59 (s, 2H), 1.39 (s, 6H).

REFERENCE EXAMPLE 26

[N-(2-Methoxyphenyl)-N-methylamino]acetic acid a) N-(2-Methoxyphenyl)aminoacetic acid.

To a cooled (0° C.) solution of 2-methoxyaniline (13.2 g, 0.108 mol) in CHCl$_3$ (100 mL) was added ethyl bromoacetate (6 mL, 0.05 mol) and the mixture was stirred at room temperature overnight. The resulting solution was washed with 0.5N NaOH and the organic phase was concentrated to a crude product. This was purified by chromatography on silica gel (hexane-EtOAc, 10%) to afford ethyl N-(2-methoxyphenyl)aminoacetate (4.2 g, 40%). This compound was dissolved in MeOH (80 mL), a solution of K$_2$CO$_3$ (4.4 g) in H$_2$O (50 mL) was added and the mixture was refluxed overnight. MeOH was removed and the resulting aqueous solution was extracted with hexane. The aqueous phase was acidified with 5N HCl and extracted with CHCl$_3$ (3×). Evaporation of the solvent afforded the title compound.

$^1$H NMR (80MHz, CDCl$_3$+CD3OD) δ (TMS): 6.83 (m, 3H), 6.56 (m, 1H), 3.91 (s, 2H), 3.86 (s, 3H), 3.62 (s, 2H).

b) Title compound

Following the procedure described in reference example 20, but starting from the compound obtained in reference example 26a, the title compound was obtained (76%).

$^1$H NMR (80 MHz, CDCl$_3$) δ (TMS): 8.78 (broad s, 1H), 6.87 (m, 4H), 3.85 (s, 3H), 3.71 (s, 2H), 2.88 (s, 1H).

REFERENCE EXAMPLE 27 trans-3-(Methoxymethyl)-3-phenylpropenoic acid

Following the procedure described in reference example 10, but using 2-methoxyacetophenone instead of 4-nitrobenzophenone, the title compound was obtained (30%).

$^1$H NMR (80MHz, CDCl$_3$) δ (TMS): 11.13 (broad s, 1H), 7.23 (s, 5H), 6.49 (s, 1H), 3.66 (s, 3H), 3.52 (s, 2H).

REFERENCE EXAMPLE 28

N-Isobutyl-N-(4-nitrophenylsulfonyl)aminoacetic acid a) N-Isobutyl-N-(4-nitrophenylsulfonyl)amine To a solution of isobutylamine (5 mL, 0.052 mol) in CH$_2$Cl$_2$ (100 mL) was added Et$_3$N (5.07 mL) and 4-nitrobenzenesulfonyl chloride (11.7 g, 0.052 mol) and the mixture was stirred at room temperature overnight. The resulting solution was washed with H$_2$O (3×), dried and concentrated to afford the desired product (9.41 g, 70%).

$^1$H NMR (80 MHz, CDCl$_3$) ≠(TMS): 8.38 (d, J=6.5 Hz, 2H), 8.08 (d, J=6.5 Hz, 2H 5.12 (t, J=6.4 Hz, 1H), 2.83 (t, J=6.5 Hz, 2H), 1.75 (hept, J=6.5 Hz, 1H 6.5 Hz, 6H).

b) Title compound

Following a similar procedure to that described in reference example 26a, but starting from the compound obtained in section a) above, the title compound was obtained (3.20 g, 28%).

$^1$H NMR (80 MHz, CDCl$_3$) δ (TMS): 8.36 (d, J=6.5 Hz, 2H), 8.03 (d, J=6.5 Hz, 2H 4.09 (s, 2H), 3.80 (s, 1H), 3.10 (d, J=7.4 Hz, 2H), 1.87 (hept, J=6.5 Hz, 1H), 0.89 (d, J=6.5 Hz, 6H).

EXAMPLE 1

1-[[1-(3,3-Diphenylpropionyl)-4-piperidyl]methyl]-1H-2-methylimidazo[4,5-c]pyridine To a cooled (0° C.) mixture of the product obtained in reference example 5 (0.5 g, 2.17 mmol), 3,3-diphenylpropionic acid (0.49 g, 2.17 mmol) and 1-hydroxybenzotriazole (0.26 g) in DMF (25 mL), was added under a nitrogen atmosphere dicyclohexylcarbodiimide (0.4 g) and the reaction mixture was stirred at room temperature for 18 h. The solvents were removed in vacuo, the resulting residue was stirred with EtOAc and the insoluble material was filtered off. The organic solution was washed with saturated NaHCO$_3$ solution, H$_2$O and brine, dried and concentrated. The residue (1.44 g) was purified by chromatography on silica gel (CHCl$_3$:MeOH, 10%) to afford the title compound as a white solid (0.59 g, 62%).

mp 79–°84° C. (C$_{28}$H$_{30}$N$_4$O);

$^1$H NMR (80 MHz, CDCl$_3$) δ (TMS): 8.96 (s, 1H), 8.35 (d, J=5.5 Hz, 1H), 7.23 (m, 11H), 4.66 (t, J=7.3 Hz, 1H), 4.65 (m, 1H), 3.83 (d, J=7.2 Hz, 2H), 3.81 (dd, J=7.8 Hz, J=3.2 Hz, 2H), 2.57 (s, 3H), 3–0.5 (complex signal, 7H);

$^{13}$C NMR (20.15 MHz, CDCl$_3$) δ (TMS): 169.25, 153.17, 143.78, 143.37, 140.85, 140.71, 139.84, 138.97, 127.93, 127.58, 127,19, 125,87, 104.74, 48.62, 47.11, 44.90, 0.88, 38.00, 36.32, 29.66, 29.03, 13.37.

The trihydrochloride was prepared by treatment of a solution of the product (0.28 g) in a 1:1 mixture of Et$_0$Ac and CH$_2$Cl$_2$ with a solution of HCl(g) in Et$_2$O. The mixture was cooled for 1 h at −20° C. and the solid was collected by filtration to afford the desired salt (0.3 g, 85%).

mp 128–°134° C. (C$_{28}$H$_{30}$N$_4$O.3HCl).

The hemifumarate was prepared by treatment of a solution of the product (0.87 g) in EtOH with a solution of fumaric acid (0.46 g) in EtOH. The mixture was cooled for 1 h at −20° C., the solid was collected by filtration and recrystallized again in EtOH to afford the desired salt (0.308 g, 30%).

mp 190°–°194° C. (C$_{28}$H$_{30}$N$_4$O.½C$_4$H$_4$O$_4$.H$_2$O).

EXAMPLE 2

1-[1-(3,3-Diphenylpropionyl)-4-piperidyl]-1H-2-methylimidazo[4,5-c]pyridine

Following the procedure described in example 1, but starting from the compound obtained in reference example 6, the title compound was obtained as a white solid (45%).

mp: 95°–100° C. (C$_{27}$H$_{28}$N$_4$O);

$^1$H NMR (80 MHz, CDCl$_3$) δ (TMS): 8.97 (s, 1H), 8.33 (d, J=5.3 Hz, 1H), 7.29 (m, 10H), 7.08 (d, J=5.3 Hz, 1H), 4.83 (m, 1H), 4.74 (t, J=7.5 Hz, 1H), 4.30 (m, 2H), 3.10 (m, 3H), 2.61 (s, 3H), 3–1.5 (complex signal, 5H).

EXAMPLE 3

1-[[1-[3-[N-(Methoxycarbonyl)amino]-3-phenylpropionyl]-4-piperidyl]methyl]-1H-2-methylimidazo[4,5-c]pyridine Following the procedure described in example 1, but using 3-[N-(methoxycarbonyl)amino]-3-phenylpropionic acid instead of 3,3-diphenylpropionic acid, the title compound was obtained as a white solid (51%).

mp: 97°–100° C. (C$_{24}$H$_{29}$N$_5$O$_3$.½H$_2$O);

$^1$H NMR (80 MHz, CDCl$_3$) δ (TMS): 8.95 (s, 1H), 8.35 (d, J=5.5 Hz, 1H), 7.30 (m, H), 6.50 (m, 1H), 5.08 (m, 1H), 4.60 (m, 1H), 3.87 (m, 3H), 3.63 (s, 3H), 2.58 (s, 3H), 3–0.5 (complex signal, 9H).

EXAMPLE 4

1-[1-[3-[N-(Methoxycarbonyl)amino]-3-phenylpropionyl]-4-piperidyl]-1H-2-methylimidazo[4,5-c]pyridine Following the procedure described in example 1, but starting from the compound obtained in reference example 6 and 3-[N-(methoxycarbonyl)amino]-3-phenylpropionic acid, the title compound was obtained as a white solid (56%).

mp: 102°–105° C. (C$_{23}$H$_{27}$N$_5$O$_3$.H$_2$O);

$^1$H NMR (80 MHz, CDCl$_3$) δ (TMS): 8.96 (s, 1H), 8.32 (d, J=5.4 Hz, 1H), 7.36 (m, 5H), 7.08 (d, J=5.4 Hz, 1H), 6.30 (m, 1H), 5.19 (m, 1H), 4.87 (m, 1H), 4.30 (m, 2H), 3.66 (s, 3H), 2.63 (s, 3H), 3.3–1.6 (complex signal, 8H).

EXAMPLE 5

1-[[1-[3-Phenyl-3-[N-(tert-butoxycarbonyl)amino]propionyl]-4-piperidyl]methyl]-1H-2-methylimidazo[4,5-c]pyridine Following the procedure described in example 1, but using 3-phenyl-3-[N-(tert-butoxycarbonyl)amino]propionic acid instead of 3,3-diphenylpropionic acid, the title compound was obtained as a white solid (40%).

$^1$H NMR (80 MHz, CDCl$_3$) δ (TMS): 8.97 (s, 1H), 8.38 (d, J=5.5 Hz, 1H), 7.30 (m, 6H), 6.30 (m, 1H), 5.08 (m, 1H), 4.60 (m, 1H), 3.87 (m, 3H), 2.60 (s, 3H), 3–0.5) (complex signal, 9H), 1.40 (s, 9H).

EXAMPLE 6

1-[[1-[3-[N-(4-aminobenzoyl)amino]-3-phenylpropionyl]-4-piperidyl]methyl]-1H-2-methylimidazo[4,5-c]pyridine a) 1-[[1-(3-Amino-3-phenylpropionyl)-4-piperidyl]methyl]-1H-2-methylimidazo[4,5-c]pyridine Following the procedure described in reference example 5, but starting from the compound obtained in example 5, the desired product was obtained as a colourless oil.

$^1$H NMR (80 MHz, CDCl$_3$) δ (TMS): 8.97 (s, 1H), 8.38 (d, J=5 Hz, 1H), 7.31 (m, 6H), 4.70 (m, 1H), 4.51 (t, J=7.3 Hz, 1H), 3.91 (m, 3H), 2.60 (s, 3H), 3.0–0.7 complex signal, 11H).

b) Title Compound

Following the procedure described in example 1, but starting from 4-aminobenzoic acid and the compound obtained in example 6a, the title compound was obtained as a white solid (75%). top: 132°–142° C. (C$_{29}$H$_{32}$N$_6$O$_2$.H$_2$O);

$^1$H NMR (80 MHz, CDCl$_3$) δ (TMS): 8.97 (s, 1H), 8.45 (m, 1H), 8.38 (d, J=5.5 Hz, 1H), 7.72 (d, J=8.3 Hz, 2H), 7.34 (m, 6H), 6.65 (d, J=8.3 Hz, 2H), 5.50 (m, 1H), 3.80 (m, 5H), 2.57 (s, 3H), 3–0.5 (complex signal, 9H).

EXAMPLE 7

1-[[1-[N-(Diphenylmethyl)aminoacetyl]-4-piperidyl]methyl]-1H-2-methylimidazo[4,5-c]pyridine Following the procedure described in example 1, but using [N-(diphenylmethyl)amino]acetic acid instead of 3,3-diphenylpropionic acid, the title compound was obtained as a white solid (65%).

mp: 77°–79° C. (C$_{28}$H$_{31}$N$_5$O.½H$_2$O);

$^1$H NMR (80 MHz, CDCl$_3$) δ (TMS): 8.97 (s, 1H), 8.38 (d, J=5.5 Hz, 1H), 7.29 (m, 11H), 4.84 (s, 1H), 4.65 (m, 1H), 3.94 (d, J=7.2 Hz, 2H), 3.50 (m, 1H), 3.96 (s, 2H), 2.60 (s, 3H), 3.0–1.0 (complex signal, 8H).

EXAMPLE 8

1-[[1-(3,3-Diphenyl-3-hydroxypropionyl)-4-piperidyl]methyl]-1H-2-methylimidazo[4,5-c]pyridine Following the procedure described in example 1, but using 3,3-diphenyl-3-hydroxypropionic acid instead of 3,3-diphenylpropionic acid, the title compound was obtained as a white solid (61%).

mp: 210°–211° C. (C$_{28}$H$_{30}$N$_4$O$_2$.½H$_2$O);

$^1$H NMR (80 MHz, CDCl$_3$) δ (TMS): 9.20 (s, 1H), 8.60 (d, J=5.5 Hz, 1H), 7.56 (m, 10H), 7.38 (d, J=5.5 Hz, 1H), 6.79 (m, 1H), 4.82 (m, 1H), 4.12 (d, J=7.2H), 2H), 4.05 (m, 1H), 3.42 (s, 2H), 2.81 (s, 3H), 3.3–1.0 (complex signal, 7H).

EXAMPLE 9

1-[[1-(2-Amino-2,2-diphenylacetyl)-4-piperidyl]methyl]-1H-2-methylimidazo[4,5-c]pyridine Following the procedure described in example 1, but using 2-amino-2,2-diphenylacetic acid instead of 3,3-diphenylpropionic acid, the title compound was obtained as a white solid (88%).

$^1$H NMR (80 MHz, CDCl$_3$) δ (TMS): 8.93 (s, 1H), 8.36 (d, J=5.5 Hz, 1H), 7.34 (m, 10H), 7.03 (d, J=5.5 Hz, 1H), 4.29 (m, 2H), 3.75 (d, J=7.2H, 2H), 2.49 (s, 3H), 2.8–1.0 (complex signal, 9H).

EXAMPLE 10

1-[[1-[2-(N-acetylamino)-2,2-diphenylacetyl]-4-piperidyl]methyl]-1H-2-methylimidazo[4,5-c]pyridine A solution of the compound obtained in example 9 (0.3 g, 0.68 ml) in pyridine (3 mL) and Ac$_2$O (1 mL) was heated at 65° C. for 18 h. The solvents were removed in vacuo and the residue partitioned between CHCl$_3$ and 0.5N NaOH. The organic phase was dried and concentrated to a residue (0.38 g), which was purified by chromatography on silica gel (CHCl$_3$:MeOH 5%) to afford the title compound (0.3 g, 92%).

mp: 138°–148° C. (C$_{29}$H$_{31}$N$_5$O$_2$);

$^1$H NMR (80 MHz, CDCl$_3$) δ (TMS): 8.93 (s, 1H), 8.35 (d, J=5.5 Hz, 1H), 8.27 (s, 1H), 7.60 (m, 4H), 7.30 (m, 6H), 7.00 (d, J=5.5 Hz, 1H), 4.45 (m, 2H), 3.72 (d, J=7.2 Hz, 2H), 2.48 (s, 3H), 2.7–0.4 (complex signal, 7H), 1.69 (s, 3H).

EXAMPLE 11

1-[[1-[3-Phenyl-3-(phenylamino)propionyl]-4-piperidyl]methyl]-1H-2-methylimidazo[4,5-c]pyridine Following the procedure described in example 1, but using 3-phenyl-3-(phenylamino)propionic acid (obtained in reference example 8) instead of 3,3-diphenylpropionic acid, the title compound was obtained as a white solid (55%).

mp: 82°–91° C. (C$_{28}$H$_{31}$N$_5$O.½H$_2$O);

$^1$H NMR (80 MHz, CDCl$_3$) δ (TMS): 8.95 (s, 1H), 8.35 (d, J=5.5 Hz, 1H), 7.32 (m, 7H), 7.06 (t, J=8.0Hz, 2H), 6.57 (t, J=8.0Hz, 2H), 5.40 (m, 1H), 4.77 (m, 2H) 3.77 (d, J=7.1H, 2H), 3.70 (m, 1H), 2.53 (s, 3H), 3.0–0.3 (complex signal, 9H).

EXAMPLE 12

1-[[1-[3-[(4-Nitrophenyl)amino]-3-phenylpropionyl]-4-piperidyl]methyl]-1H-2-methylimidazo[4,5-c]pyridine Following the procedure described in example 1, but using 3-(4-nitrophenyl)amino-3-phenylpropionic acid (obtained in reference example 9) instead of 3,3-diphenylpropionic acid, the title compound was obtained as a white solid (90%).

mp: 230°–232° C. (C$_{28}$H$_{30}$N$_6$O$_3$.½H$_2$O);

$^1$H NMR (80 MHz, CDCl$_3$) δ (TMS): 8.98 (s, 1H), 8.38 (d, J=5.5 Hz, 1H), 7.97 (d, J=9 Hz, 2H), 7.35 (m, 5H), 7.12 (d, J=5.5 Hz, 1H), 6.95 (m, 1H), 6.42 (d, J=4.76 (m, 2H), 3.75 (m, 3H), 2.58 (s, 3H), 3.0–0.3 (complex signal, 9H).

EXAMPLE 13

1-[[1-[3-[(4-Aminophenyl)amino]-3-phenylpropionyl]-4-piperidyl]methyl]-1H-2-methylimidazo[4,5-c]pyridine To a solution of the product obtained in example 12 (226 mg, 0.4 mmol) in EtOH (5 mL) and H$_2$O (0.6 mL) was added a solution of CaCl$_2$ (33.6 mg) in H$_2$O (0.26 mL) and powdered zinc (0.58 g). The resulting mixture was heated at 50° C. for 45 min, filtered through celite and the flitrate was concentrated. The residue was purified by chromatography on silica gel (CHCl$_3$:MeOH 10%), to afford the title compound as a white solid (0.17 g, 91%).

$^1$H NMR (80 MHz, CDCl$_3$) δ (TMS): 8.93 (s, 1H), 8.34 (d, J=5.5 Hz, 1H), 7.31 (m, 6H), 6.44 (broad s, 4H), 4.62 (m, 2H), 3.80 (d, J=7.0 Hz, 2H), 3.52 (m, 4H) 2.55 (s, 3H), 3.0–0.5 (complex signal, 9H).

A solution of the title compound in CHCl$_3$ was treated with a solution of HCl(g) in Et$_2$O, to afford the hydrochloride of the title compound.

mp: 189°–195° C. (C$_{28}$H$_{32}$N$_6$O.4HCl.2H$_2$O).

EXAMPLE 14

1-[[1-(2,2-Dicyclohexylacetyl)-4-piperidyl]methyl]-1H-2-methylimidazo[4,5-c]pyridine Following the procedure described in example 1, but using 2,2-dicyclohexylacetic acid instead of 3,3-diphenylpropionic acid, the title compound was obtained as a white solid (23%).

mp: 161°–164° C. (C$_{27}$H$_{40}$N$_4$O.¾H$_2$O);

$^1$H NMR (80 MHz, CDCl$_3$) δ (TMS): 8.97 (s, 1H), 8.37 (d, J=5.5 Hz, 1H), 7.19 (d, J=5.5 Hz, 1H), 4.82 (m, 1H), 4.03 (m, 1H), 3.98 (d, J=7.2 Hz, 2H), 2.62 (s, 3H), 3.0–0.5 (complex signal, 30H).

EXAMPLE 15

1-[[1-(3,3-Diphenylpropenoyl)-4-piperidyl]methyl]-1H-2-methylimidazo[4,5-c]pyridine Following the procedure described in example 1, but using 3,3-diphenylpropenoic acid (obtained in reference example 12) instead of 3,3-diphenylpropionic acid, the title compound was obtained as a white solid (85%).

mp: 85°–92° C. ($C_{28}H_{28}N_4O \cdot H_2O$);

$^1$H NMR (80 MHz, CDCl$_3$) δ (TMS): 8.95 (s, 1H), 8.37 (d, J=5.5 Hz, 1H), 7.32 (m, 10H), 7.09 (d, J=5.4 Hz, 1H), 6.27 (s, 1H), 4.65 (m, 1H), 3.82 (m, 1H), 3.77 (dd, J=6.7 Hz, J=2.2 Hz, 2H), 2.54 (s, 3H), 2.8–0.5 (complex signal, 7H).

EXAMPLE 16 cis and trans-1-[[1-[3-(4-Nitrophenyl)-3-phenylpropenoyl]-4-piperidyl]methyl]-1H-2-methylimidazo[4,5-c]pyridine Following the procedure described in example 1, but using a cis/trans mixture of 3-(4-nitrophenyl)-3-phenylpropenoic acid (obtained in reference example 10) instead of 3,3-diphenylpropionic acid, the title compound was obtained as a white solid (85%).

mp: 106°–112° C. ($C_{28}H_{27}N_5O_3 \cdot \frac{1}{2}H_2O$);

$^1$H NMR (80 MHz, CDCl$_3$) δ (TMS): 8.95 (s, 1H), 8.37 (d, J=5.5 Hz, 1H), 8.18 (dd, J=8.6 Hz, J=3.2 Hz, 2H), 7.37 (m, 8H), 6.49 (s, 0.5H), 6.40 (s, 0.5H), 4.66 (m, 1H), 3.84 (m, 3H), 2.57 (s, 3H), 2.8–0.5 (complex signal, 7H).

EXAMPLE 17a and 17b a) cis -1-[[1-[3-(4-Aminophenyl)-3-phenylpropenoyl]-4-piperidyl]methyl]-1H-2-methylimidazo[4,5-c]pyridine b) trans -1-[[1-[3-(4-Aminophenyl)-3-phenylpropenoyl]-4-piperidyl]methyl]-1H-2-methylimidazo[4,5-c]pyridine Following the procedure described in reference example 3, but starting from the compound obtained in example 16, the title compound was obtained as a cis/trans mixture of isomers, which were separated by chromatography on silica gel (CHCl$_3$:MeOH, 10%).

Slower eluting, isomer cis (example 17a)(54%):

mp: 121°–135° C. ($C_{28}H_{29}N_5O \cdot \frac{1}{2}H_2O$);

$^1$H NMR (80 MHz, CDCl$_3$) δ (TMS): 8.95 (s, 1H), 8.36 (d, J=5.5 Hz, 1H), 7.29 (s, 5H), 7.07 (m, 3H), 6.65 (d, J=6.5 Hz, 2H), 6.07 (s, 1H), 4.70 (m, 1H), 3.82 (m, 3H), 2.57 (s, 3H), 2.8–0.5 (complex signal, 9H).

Faster eluting, isomer trans (example 17b) (22%):

mp: 223°–224° C. ($C_{28}H_{29}N_5O \cdot \frac{1}{2}H_2O$);

$^1$H NMR (80 MHz, CDCl$_3$) δ (TMS): 8.96 (s, 1H), 8.38 (d, J=5.5 Hz, 1H), 7.30 (s, 5H), 7.05 (m, 3H), 6.60 (d, J=6.5Hz, 2H), 6.17 (s, 1H), 4.60 (m, 1H), 3.81 (m, 3H), 2.55 (s, 3H), 2.8–0.5 (complex signal, 9H).

Following the same procedure described in example 16 but using pure cis or pure trans-3-(4-nitrophenyl)-3-phenylpropenoic acid (described in reference example 10a and 10b respectively) instead of a cis/trans mixture and then reducing the resulting compounds as described above, the title compound was obtained in pure cis or trans form.

Alternatively, the pure cis isomer was obtained as follows: To a solution of SnCl$_2 \cdot$2H$_2$O (21 g) in HCl (21 mL) was added a solution of cis 1-[[1-[3-(4-nitrophenyl)-3-phenylpropenoyl]-4-piperidyl]methyl]-1H-2-methylimidazo[4,5-c]pyridine (10 g, 20.7 mmol) in AcOH (35 mL). The mixture was stirred at room temperature overnight, and was then made basic with cooled aqueous NaOH and extracted with CHCl$_3$ (3×), whereupon a solid precipitated in the organic phase. This solid was collected and the organic solution was dried and concentrated to give 8 g of the desired product. The first precipitate and the aqueous phase were combined and then treated with more NaOH solution and extracted with CHCl$_3$ (3×). Evaporation of the solvent afforded 1.73 g more of the title product.

EXAMPLE 18

1-[[1-(3,3-Dicyclohexyl-3-hydroxypropionyl)-4-piperidyl]methyl]-1H-2-methylimidazo[4,5-c]pyridine Following the procedure described in example 1, but using 3,3-dicyclohexyl-3-hydroxypropionic acid instead of 3,3-diphenylpropionic acid, the title compound was obtained as a white solid (27%).

mp: 75°–81° C. ($C_{28}H_{42}N_4O_2 \cdot \frac{3}{4}H_2O$);

$^1$H NMR (80 MHz, CDCl$_3$) δ (TMS): 8.95 (s, 1H), 8.37 (d, J=5.5 Hz, 1H), 7.24 (d, J=5.5 Hz, 1H), 6.09 (s, 1H), 4.69 (m, 1H), 4.04 (d, J=7.2 Hz, 2H), 3.96 (m, 1H), 2.64 (s, 3H), 3.0–0.5 (complex signal, 31H).

EXAMPLE 19

1-[[1-[3,3-Diphenyl-3-(ethoxycarbonyl)propionyl]-4-piperidyl]methyl]-1H-2-methylimidazo[4,5-c]pyridine Following the procedure described in example 1, but using 3,3-diphenyl-3-ethoxycarbonylpropionic acid (obtained in reference example 7) instead of 3,3-diphenylpropionic acid, the title compound was obtained as a white solid (60%).

mp: 79°–89° C. ($C_{31}H_{34}N_4O_3 \cdot H_2O$);

$^1$H NMR (80 MHz, CDCl$_3$) δ (TMS): 8.98 (s, 1H), 8.38 (d, J=5.5 Hz, 1H), 7.28 (m, 11H), 4.62 (m, 1H), 4.22 (q, J=7.3 Hz, 2H), 3.85 (d, J=7.2 Hz, 2H), 3.81 (m, 1H), 3.48 (m, 2H), 2.59 (s, 3H), 3–0.5 (complex signal, 7H), 1.17 (t, J=7.2 Hz, 3H).

EXAMPLE 20

(R)-1-[[1-[2-(Methoxycarbonylamino)-2-phenylacetyl]-4-piperidyl]methyl]-1H-2-methylimidazo[4,5-c]pyridine Following the procedure described in example 1, but using (R)-2-(methoxycarbonylamino)-2-phenylacetic acid instead of 3,3-diphenylpropionic acid, the title compound was obtained as a white solid (94%).

mp: 108°–113° C. ($C_{23}H_{27}N_5O_3 \cdot \frac{1}{2}H_2O$);

$^1$H NMR (80 MHz, CDCl$_3$) δ (TMS): 8.95 (s, 1H), 8.35 (d, J=5.5 Hz, 1H), 7.37 (m, 5H), 7.01 (d, J=5.5 Hz, 1H), 6.28 (m, 1H), 5.57 (m, 1H), 4.70 (m, 1H), 3.80 (m, 3H), 3.63 (s, 3H), 3–1 (complex signal, 10H).

EXAMPLE 21

1-[[1-(3-Hydroxy-3-phenylbutanoyl)-4-piperidyl]methyl]-1H-2-methylimidazo[4,5-c]pyridine Following the procedure described in example 1, but using 3-hydroxy-3-phenylbutanoic acid instead of 3,3-diphenylpropionic acid, the title compound was obtained as a white solid (41%).

mp: 199°–200° C. ($C_{23}H_{28}N_4O_2 \cdot \frac{1}{4}H_2O$);

$^1$H NMR (80 MHz, CDCl$_3$) δ (TMS): 8.90 (s, 1H), 8.38 (d, J=5.5 Hz, 1H), 7.22 (m, 6H), 6.0 (m, 1H), 4.60 (m, 1H), 3.91 (m, 3H), 2.57 (s, 3H), 3–0.5 (complex signal), 1.59 (s, 3H).

EXAMPLE 22

1-[[1-[3-(4-Nitrophenyl)butanoyl]-4-piperidyl]methyl]-1H-2-methylimidazo[4,5-c]pyridine Following the procedure described in example 1, but using 3-(4-nitrophenyl)butanoic acid (obtained in reference example 13) instead of 3,3-diphenylpropionic acid, the title compound was obtained as a white solid (53%).

mp: 75°–77° C. ($C_{23}H_{27}N_5O_3.½H_2O$);

$^1$H NMR (80 MHz, CDCl$_3$) δ (TMS): 8.92 (s, 1H), 8.36 (d, J=5.5 Hz, 1H), 8.28 (d, J=9.5 Hz, 2H), 7.42 (d, J=9.5 Hz, 2H), 7.12 (d, J=5.5 Hz, 1H), 4.60 (m, 1H), 3.93 (m, 3H), 3.50 (m, 1H), 2.61 (s, 3H), 3–0.5 (complex signal, 9H), 1.36 (d, J=6.9 Hz, 3H).

EXAMPLE 23

1-[[1-[3-(4-Aminophenyl)butanoyl]-4-piperidyl]methyl]-1H-2-methylimidazo[4,5-c]pyridine Following the procedure described in reference example 3, but starting from the compound obtained in example 22, the title compound was obtained as a white solid (35%).

mp: 116°–117° C. ($C_{23}H_{29}N_5O.½H_2O$);

$^1$H NMR (80 MHz, CDCl$_3$+CD3OD) δ (TMS): 8.88 (s, 1H), 8.33 (d, J=5.5 Hz, 1H), 7.30 (d, J=5.5 Hz, 1H), 7.02 (d, J=9.0 Hz, 2H), 6.67 (d, J=9.0 Hz, 2H), 4.64 (m, 1H), 3.93 (m, 3H), 3.80 (m, 2H), 3.20 (m, 1H), 2.63 (s, 3H), 3–0.5 (complex signal, 1.31 (d, J=6.9 Hz, 3H).

EXAMPLE 24

1-[[1-[2-(4-Nitrophenyl)propionyl]-4-piperidyl]methyl]-1H-2-methylimidazo[4,5-c]pyridine Following the procedure described in example 1, but using 2-(4-nitrophenyl)propionic acid instead of 3,3-diphenylpropionic acid, the title compound was obtained as a white solid (12%).

mp: 82°–87° C. ($C_{22}H_{25}N_5O_3.½H_2O$);

$^1$H NMR (80 MHz, CDCl$_3$) δ (TMS): 8.94 (s, 1H), 8.33 (d, J=5.5 Hz, 1H), 8.16 (d, J=9.5 Hz, 2H), 7.44 (d, J=9.5 Hz, 2H), 7.12 (m, 1H), 4.73 (m, 1H), 4.0 (m, 4H), 2.55 (s, 3H), 3–0.5 (complex signal, 7H), 1.46 (d, J=6.9 Hz, 3H).

EXAMPLE 25

1-[[1-[2-(4-Aminophenyl)propionyl]-4-piperidyl]methyl]-1H-2-methylimidazo[4,5-c]pyridine Following the procedure described in reference example 3, but starting from the compound obtained in example 24, the title compound was obtained as a white solid (34%).

mp: 91°–95° C. ($C_{22}H_{27}N_5O.H_2O$);

$^1$H NMR (80 MHz, CDCl$_3$) δ (TMS): 8.96 (s, 1H), 8.38 (d, J=5.5 Hz, 1H), 7.05 (m, 1H), 6.99 (d, J=9.5 Hz, 2H), 6.61 (d, J=9.5 Hz, 2H), 4.74 (m, 1H), 3.77 (m, 4H), 2.53 (s, 3H), 3–0.5 (complex signal, 9H), 1.37 (d, J=6.9 Hz, 3H).

EXAMPLE 26

1-[[1-[3-Ethoxycarbonyl-3-(4-nitrophenyl)propionyl]-4-piperidyl]methyl]-1H-2-methylimidazo[4,5-c]pyridine Following the procedure described in example 1, but using 3-ethoxycarbonyl-3-(4-nitrophenyl)propionic acid (obtained in reference example instead of 3,3-diphenylpropionic acid, the title compound was obtained as a white solid (18%).

mp: 81°–84° C. ($C_{25}H_{29}N_5O_5.2H_2O$);

$^1$H NMR (80 MHz, CDCl$_3$) δ (TMS): 8.95 (s, 1H), 8.35 (d, J=5.5 Hz, 1H), 8.16 (d, J=9.5 Hz, 2H), 7.48 (d, J=9.5 Hz, 2H), 7.22 (m, 1H), 4.63 (m, 1H), 4.03 (m, 6H), 2.62 (s, 3H), 3.3–1 (complex signal, 9H), 1.19 (t, J=6.5 Hz, 3H).

EXAMPLE 27

1-[[1-[3-(4-Aminophenyl)-3-ethoxycarbonylpropionyl]-4-piperidyl]methyl]-1H-2-methylimidazo[4,5-c]pyridine Following the procedure described in reference example 3, but starting from the compound obtained in example 26, the title compound was obtained as a white solid (90%).

mp: 204°–205° C. ($C_{25}H_{31}N_5O_3.H_2O$);

1H NMR (80 MHz, CDCl$_3$) δ (TMS): 8.98 (s, 1H), 8.41 (d, J=5.5 Hz, 1H), 7.26 (m, 1H), 7.07 (d, J=9.5 Hz, 2H), 6.62 (d, J=9.5 Hz, 2H), 4.65 (m, 1H), 3.98 (m, 6H), 2.62 (s, 3H), 3.3–1 (complex signal, 11H), 1.19 (t, J=6.5 Hz, 3H).

EXAMPLE 28

1-[[1-(3-Ethoxycarbonyl-3-phenylpropionyl)-4-piperidyl]methyl]-1H-2-methylimidazo[4,5-c]pyridine Following the procedure described in example 1, but using 3-ethoxycarbonyl-3-phenylpropionic acid (obtained in reference example 15) instead of 3,3-diphenylpropionic acid, the title compound was obtained as a white solid (38%).

mp: 173°–174° C. ($C_{25}H_{30}N_4O_3.H_2O$);

$^1$H NMR (80 MHz, CDCl$_3$) δ (TMS): 8.99 (s, 1H), 8.38 (d, J=5.5 Hz, 1H), 7.30 (m, 6H), 4.66 (m, 1H), 4.13 (m, 6H), 2.62 (s, 3H), 3.5–1 (complex signal, 9H), 1.19 (t, J=7.12 Hz, 3H).

EXAMPLE 29 cis and trans -1-[[1-[3-(3-Nitrophenyl)-3-phenylpropenoyl]-4-piperidyl]methyl]-1H-2-methylimidazo[4,5-c]pyridine Following the procedure described in example 1, but using cis and trans-3-(3-nitrophenyl)-3-phenylpropenoic acid (obtained in reference example 16) instead of 3,3-diphenylpropionic acid, the title compound was obtained as a white solid (95%).

mp: 99°–103° C. ($C_{28}H_{27}N_5O_3.½H_2O$);

$^1$H NMR (80 MHz, CDCl$_3$) δ (TMS): 8.97 (s, 1H), 8.39 (d, J=5.5 Hz, 1H), 8.27 (m, 2H), 7.30 (m, 8H), 6.54 (s, 0.66H), 6.39 (s, 0.34H), 4.62 (m, 1H), 3.98 (m, 3H), 2.63 (s, 3H), 3.1–0.7 (complex signal, 7H).

EXAMPLE 30 cis and trans -1-[[1-[3-(3-Aminophenyl)-3-phenylpropenoyl]-4-piperidyl]methyl]-1H-2-methylimidazo[4,5-c]pyridine Following the procedure described in reference example 3, but starting from the compound obtained in example 29, the title compound was obtained as a white solid (14%).

mp: 122°–133° C. ($C_{28}H_{29}N_5O.H_2O$);

$^1$H NMR (80 MHz, CDCl$_3$) δ (TMS): 8.94 (s, 1H), 8.33 (d, J=5.5 Hz, 1H), 7.28 (m, 8H), 6.63 (m, 2H), 6.20 (s, 0.4H), 6.16 (s, 0.6H), 4.67 (m, 1H), 3.78 (m, 3H), 2.54 (s, 3H), 2.8–0.1 (complex signal, 9H).

EXAMPLE 31

1-[[1-[3-(4-Aminophenyl)-3-[N-(ethoxycarbonyl)
amino]propionyl]-4-piperidyl]methyl]-1H-2-
methylimidazo[4,5-c]pyridine Following the procedure described in example 1, but using 3-[N-(ethoxycarbonyl)amino]-3-(4-nitrophenyl) propionic acid (obtained in reference example 17), and hydrogenating the compound thus obtained according to the procedure described in reference example 3, the title compound was obtained as a white solid (15%).

mp: 113°–116° C. ($C_{25}H_{32}N_6O_3 \cdot \frac{1}{2}H_2O$);

$^1$H NMR (80 MHz, CDCl$_3$) δ (TMS): 8.94 (s, 1H), 8.35 (d, J=5.5 Hz, 1H), 7.21 (d, J=5.5 Hz, 1H), 7.07 (d, J=9.5 Hz, 2H), 6.63 (m, 3H), 4.95 (m, 1H), 4.60 (q, J=7.2 Hz, 2H), 3.88 (m, 3H), 2.59 (s, 3H), 3.6–0.5 (complex signal, 11H), 1.19 (t, J=7.2 Hz, 3H).

EXAMPLE 32

1-[[1-(3-Phenylhexanoyl)-4-piperidyl]methyl]-1H-2-
methylimidazo[4,5-c]pyridine

Following the procedure described in example 1, but using 3-phenylhexanoic acid instead of 3,3-diphenylpropionic acid, the title compound was obtained as a white solid (51%).

mp: 39°–55° C. ($C_{25}H_{32}N_4O \cdot \frac{1}{2}H_2O$);

$^1$H NMR (80 MHz, CDCl$_3$) δ (TMS): 8.96 (s, 1H), 8.36 (d, J=5.5 Hz, 1H), 7.24 (m, 6H), 4.60 (m, 1H), 3.84 (m, 3H), 3.18 (m, 1H), 2.58 (s, 3H), 2.8–0.5 (complex signal, 13H), 0.97 (t, J=6.9 Hz, 3H).

EXAMPLE 33

1-[[1-[3-Hydroxy-3-(2-methylpropyl)-5-
methylhexanoyl]-4-piperidyl]methyl]-1H-2-
methylimidazo[4,5-c]pyridine Following the procedure described in example 1, but using 3-hydroxy-3-(2-methylpropyl)-5-methylhexanoic acid (obtained in reference example 18) instead of 3,3-diphenylpropionic acid, the title compound was obtained as a white solid (25%).

mp: 38°–51° C. ($C_{24}H_{38}N_4O_2 \cdot \frac{1}{4}H_2O$);

$^1$H NMR (80 MHz, CDCl$_3$) δ (TMS): 8.98 (s, 1H), 8.38 (d, J=5.5 Hz, 1H), 7.21 (d, J=5.5 Hz, 1H), 4.98 (s, 1H), 4.69 (m, 1H), 4.01 (d, J=7.2 Hz, 2H), 3.85 (m, 1H), 2.62 (s, 3H), 3.1–1.1 (complex signal, 15H), 1.00 (broad s, 12H).

EXAMPLE 34

1-[[1-[3-1H-(4-Aminobenzenesulfonyl)amino]-3-
phenylpropionyl]-4-piperidyl]methyl]-1H-2-
methylimidazo[4,5-c]pyridine Following the procedure described in example 1, but using 3-[N-(4-nitrobenzenesulfonyl)amino]propionic acid, and hydrogenating the compound thus obtained according to the procedure described in reference example 3, the title compound was obtained as a white solid (22%).

mp: 126°–134° C. ($C_{28}H_{32}N_6O_3S \cdot H_2O$);

$^1$H NMR (80 MHz, CDCl$_3$+CD3OD) δ(TMS): 8.86 (s, 1H), 8.32 (d, J=5.5 Hz, 1H), 7.53 (d, J=8.3 Hz, 2H), 7.16 (m, 7H), 6.86 (d, J=8.3 Hz, 2H), 4.65 (m, 1H), 4.55 (m, 1H), 4.00 (m, 5H), 2.61 (s, 3H), 3–0.5 (complex signal, 9H).

Alternatively, the compound obtained in example 6a was reacted with 4-nitrobenzenesulfonyl chloride in the presence of triethylamine to give 1-[[1-[3-[N-(4-nitrobenzenesulfonyl)amino]-3-phenylpropionyl]-4-piperidyl]methyl]-1H-2-methylimidazo[4,5-c]pyridine, which was hydrogenated according to the procedure described in reference example 3 to give the title compound.

EXAMPLE 35

1-[[1-[(N-Ethoxycarbonyl-N-phenylamino)acetyl]-4-
piperidyl]methyl]-1H-2-methylimidazo[4,5-c]
pyridine Following the procedure described in example 1, but using N-ethoxycarbonyl-N-phenylglycine (prepared from N-phenylglycine and ethyl chloroformate) instead of 3,3-diphenylpropionic acid, the title compound was obtained as a white solid (41%).

mp: 130°–137° C. ($C_{24}H_{29}N_5O_3 \cdot H_2O$);

$^1$H NMR (80 MHz, CDCl$_3$) δ (TMS): 8.96 (s, 1H), 8.35 (d, J'5.5Hz, 1H), 7.31 (m, 6H), 4.43 (m, 1H), 4.40 (m, 2H), 4.15 (q, J=7.2 Hz, 2H), 3.96 (d, J=6.9 Hz, 2H) 3.90 (m, 1H), 2.61 (s, 3H), 3–1.2 (complex signal, 7H), 1.19 (t, J=7.2 Hz, 3H).

EXAMPLE 36

(S)-1-[[1-[[N-(1-Ethoxycarbonyl-3-methylbutyl)
amino]carbonyl]-4-piperidyl]methyl]-1H-2-
methylimidazo[4,5-c]pyridine A solution of the compound obtained in reference example 5 (0.5 g, 2.1 mmol) and N-phenoxycarbonyl-L-Leucine ethyl ester (0.78 g, 2.7 mmol, prepared from L-Leucine ethyl ester and phenyl chloroformate) in pyridine (15 mL) was refluxed for 18 h. The solvent was removed in vacuo and the residue partitioned between CHCl$_3$ and 0.5N NaOH. The organic phase was dried and concentrated to a residue (1.33 g), which was purified by chromatography on silica gel (CHCl$_3$:MeOH, 5%) to afford the title compound as a white solid (0.22 g, 44%).

mp: 60°–63° C. ($C_{22}H_{33}N_5O_3 \cdot \frac{3}{4}H_2O$);

$^1$H NMR (80 MHz, CDCl$_3$) δ (TMS): 8.96 (s, 1H), 8.36 (m, 1H), 7.26 (d, J=5.5 Hz, 1H), 5.30 (d, J=8.17 Hz, 1H), 4.51 (q, J=8.12 Hz, 1H), 4.18 (q, J=6.5 Hz, 2H), 4.15 (m, 1H), 4.00 (d, J=7.3 Hz, 2H), 2.70 (m, 3H), 2.62 (s, 3H), 2.1–1.4 (complex signal, 8H), 1.27 (t, J=6.5 Hz, 3H), 0.93 (d, J=5.5 Hz, 6H).

EXAMPLE 37

(S)-1-[[1-[[N-[1-Ethoxycarbonyl-2-(4-nitrophenyl)
ethyl]amino]carbonyl]-4-piperidyl]methyl]-1H-2-
methylimidazo[4,5-c]pyridine Following the procedure described in example 36, but using N-phenoxycarbonyl-4-nitro-L-phenylalanine ethyl ester instead of N-phenoxycarbonyl-L-Leucine ethyl ester, the title compound was obtained as a white solid (54%).

mp: 85°–89° C. ($C_{25}H_{30}N_6O_5 \cdot \frac{1}{2}H_2O$);

$^1$H NMR (80 MHz, CDCl$_3$) δ (TMS): 8.94 (s, 1H), 8.35 (d, J=5.5 Hz, 1H), 8.11 (d, J=9.2 Hz, 2H), 7.32 (d, J=9.2Hz, 2H), 7.20 (d, J=5.5Hz, 1H), 5.32 (d, J=8.17 Hz, 1H) 4.81 (q, J=8.12 Hz, 1H), 4.18 (q, J=6.5 Hz, 2H), 4.00 (m, 1H), 3.98 (d, J=3.23 (d, J=5.8 Hz, 2H), 2.70 (m, 3H), 2.63 (s, 3H), 2.1–1.4 (complex signal, 5H), 1.5 (t, J=6.5 Hz, 3H).

EXAMPLE 38

(S)-1-[[1-[[N-[2-(4-Aminophenyl)-1-
ethoxycarbonylethyl]amino]carbonyl]-4-piperidyl]
methyl]-1H-2-methylimidazo[4,5-c]pyridine Following the procedure described in reference example 3, but starting from the compound obtained in example 37, the title compound was obtained as a white solid (94%).

mp: 87°–96° C. ($C_{25}H_{32}N_6O_3.H_2O$);

$^1$H NMR (80 MHz, CDCl$_3$) δ (TMS): 8.96 (s, 1H), 8.36 (d, J=5.5 Hz, 1H), 7.20 (d, J=5.5 Hz, 1H), 6.88 (d, J=9.2 Hz, 2H), 6.57 (d, J=9.2 Hz, 2H), 4.97 (d, J=8.1 Hz, 1H), 4.65 (q, J=8.12 Hz, 1H), 4.18 (q, J=6.5 Hz, 2H), 4.00 (m, 1H, 3.98 (d, J=7.3 Hz, 2H), 2.98 (d, J=5.8 Hz, 2H), 2.80 (m, 5H), 2.61 (s, 3H), 2.1–1.4 (complex signal, 5H), 1.25 (t, J=6.5 Hz, 3H).

EXAMPLE 39

(S)-1-[[1-[[N-(1-Ethoxycarbonyl-1-phenylmethyl) amino]carbonyl]-4-piperidyl]methyl]-1H-2-methylimidazo[4,5-c]pyridine Following the procedure described in example 36, but using N-phenoxycarbonyl-L-phenylglycine ethyl ester (prepared from L-phenylglycine ethyl ester and phenyl chloroformate) instead of N-phenoxycarbonyl-L-Leucine ethyl ester, the title compound was obtained as a white solid (61%).

mp: 153°–154° C. ($C_{24}H_{29}N_5O_3.\frac{1}{2}H_2O$);

$^1$H NMR (80 MHz, CDCl$_3$) δ (TMS): 8.96 (s, 1H), 8.37 (d, J=5.5 Hz, 1H), 7.33 (m, 5H), 7.20 (d, J=5.5 Hz, 1H), 5.51 (m, 2H), 4.18 (q, J=6.5 Hz, 2H), 4.00 (m, 1H) 3.98 (d, J=7.3 Hz, 2H), 2.72 (m, 3H), 2.61 (s, 3H), 2.1–1.4 (complex signal, 5H), 1.20 (t, J=6.5 Hz, 3H).

EXAMPLE 40

1-[[1-(3-Phenylbutanoyl)-4-piperidyl]methyl]-1H-2-methylimidazo[4,5-c]pyridine

Following the procedure described in example 1, but using 3-phenylbutanoic acid instead of 3,3-diphenylpropionic acid, the title compound was obtained as a white solid (38%).

mp: 38°–41° C. ($C_{23}H_{28}N_4O.H_2O$);

$^1$H NMR (80 MHz, CDCl$_3$) δ (TMS): 8.87 (s, 1H), 8.28 (d, J=5.5 Hz, 1H), 7.16 (m, 6H), 4.60 (m, 1H), 3.76 (m, 3H), 3.30 (m, 1H, 2.50 (s, 3H), 3–0.5 (complex signal, 9H), 1.25 (d, J=6.9 Hz, 3H).

EXAMPLE 41

1-[[1-(3-Methyl-3-phenylbutanoyl)-4-piperidyl] methyl]-1H-2-methylimidazo[4,5-c]pyridine Following the procedure described in example 1, but using 3-methyl-3-phenylbutanoic acid (obtained in reference example 19) instead of 3,3-diphenylpropionic acid, the title compound was obtained as a white solid (58%).

mp: 37°–45° C. ($C_{24}H_{30}N_4O.\frac{1}{2}H_2O$);

$^1$H NMR (80 MHz, CDCl$_3$) δ (TMS): 8.95 (s, 1H, 8.38 (d, J=5.5Hz, 1H), 7.26 (m, 6H), 4.65 (m, 1H, 3.86 (d, J=7.1 Hz, 2H), 3.50 (m, 1H), 2.58 (s, 3H), 3–0.5 (complex signal, 9H), 1.25 (s, 6H).

EXAMPLE 42

1-[[1-[(N-methyl-N-phenylamino)acetyl]-4-piperidyl]methyl]-1H-2-methylimidazo[4,5-c]pyridine Following the procedure described in example 1, but using N-methyl-N-phenylaminoacetic acid (obtained in reference example 20) instead of 3,3-diphenylpropionic acid, the title compound was obtained as a white solid (39%).

mp: 74°–78° C. ($C_{22}H_{27}N_5O.H_2O$);

$^1$H NMR (80 MHz, CDCl$_3$) δ (TMS): 8.96 (s, 1H), 8.36 (d, J=5.5 Hz, 1H), 7.21 (m, 3H), 6.71 (m, 3H), 4.60 (m, 1H), 4.05 (s, 2H), 3.92 (d, J=7.1 Hz, 2H), 3.80 (m, 1H), 2.99 (s, 3H), 2.59 (s, 3H), 3–1 (complex signal, 7H).

EXAMPLE 43

1-[[1-[3-Methyl-3-(4-nitrophenyl)butanoyl]-4-piperidyl]methyl]-1H-2-methylimidazo[4,5-c]pyridine Following the procedure described in example 1, but using 3-methyl-3-(4-nitrophenyl)butanoic acid (obtained in reference example 21) instead of 3,3-diphenylpropionic acid, the title compound was obtained as an oil (28%).

$^1$H RMN (80 MHz, CDCl$_3$) δ (TMS): 8.96 (s, 1H), 8.37 (d, J=5.5 Hz, 1H), 8.11 (d, J=8.4 Hz, 2H), 7.51 (d, J=8.4 Hz, 2H), 7.18 (d, J=5.5 Hz, 1H, 4.55 (m, 1H), 3.95 (d, J=7.1 Hz, 2H), 3.83 (m, 1H), 2.59 (s, 3H), 3–0.5 (complex signal, 9H), 1.50 (s, 6H).

EXAMPLE 44

1-[[1-[3-(4-Aminophenyl)-3-methylbutanoyl]-4-piperidyl]methyl]-1H-2-methylimidazo[4,5-c]pyridine Following the procedure described in reference example 3, but starting from the compound obtained in example 43, the title compound was obtained as a white solid (57%).

mp: 172°–173° C. ($C_{24}H_{31}N_5O.\frac{3}{4}H_2O$);

$^1$H NMR (80 MHz, CDCl$_3$) δ (TMS): 8.96 (s, 1H, 8.38 (d, J=5.5Hz, 1H), 7.18 (m, 3H), 6.62 (d, J=5.5 Hz, 2H), 4.65 (m, 1H), 3.86 (d, J=7.1 Hz, 2H), 3.63 (m, 2H), 3.50 (m, 1H), 2.59 (s, 3H), 3–0.5 (complex signal, 9H), 1.25 (s, 6H).

EXAMPLE 45

1-[[1-[[N-(Diphenylmethyl)amino]carbonyl]-4-piperidyl]methyl]-1H-2-methylimidazo[4,5-c]pyridine Following the procedure described in example 36, but using N-phenoxycarbonyl-N-(diphenylmethyl)amine (prepared from aminodiphenylmethane and phenyl chloroformate) instead of N-phenoxycarbonyl-L-Leucine ethyl ester, the title compound was obtained as a white solid (26%).

mp: 212°–218° C. ($C_{27}H_{29}N_5O.H_2O$);

$^1$H NMR (80 MHz, CDCl$_3$) δ (TMS): 8.96 (s, 1H), 8.35 (d, J=5.5 Hz, 1H), 7.27 (m, 11H), 6.14 (d, J=7.0 Hz, 1H), 5.12 (d, J=7.0 Hz, 1H), 4.00 (m, 1H), 3.96 (d, J=7.3 Hz, 2H), 2.70 (m, 2H), 2.61 (s, 3H), 2.1–1.1 (complex signal, 6H).

EXAMPLE 46

1-[[1-[[N-(4-Aminobenzoyl)-N-methylamino]acetyl]-4-piperidyl]methyl]-1H-2-methylimidazo[4,5-c]pyridine a) 1-[[1-[(N-methyl-N-tert-butoxycarbonylamino)acetyl]-4-piperidyl]methyl]-1H-2-methylimidazo[4,5-c]pyridine Following the procedure described in example 1, but using N-(tert-butoxycarbonyl)-N-methylamino]acetic acid instead of 3,3-diphenylpropionic acid, the desired product was obtained (63%).

b) 1-[[1-[N-methylaminoacetyl]-4-piperidyl]methyl]-1H-2-methylimidazo[4,5-c]pyridine Following the procedure described in reference example 5, but starting from the compound obtained in section a), the desired product was prepared (quantitative yield).

c) Title compound

Following the procedure described in example 6b, but using the compound obtained in example 46b instead of the compound obtained in example 6a, the title compound was obtained (32%).

mp: 120°–124° C. ($C_{23}H_{28}N_6O_2.H_2O$);

$^1$H NMR (80 MHz, CDCl$_3$) δ (TMS): 8.97 (s, 1H), 8.38 (d, J=5.5 Hz, 1H), 7.25 (m, 3H), 6.61 (d, J=9.0 Hz, 2H), 4.64 (m, 1H), 4.01 (m, 2H), 3.98 (d, J=7.1 Hz, 2H), 3.10 (s, 3H), 2.62 (s, 3H), 3.3–1 (complex signal, 10H).

EXAMPLE 47

1-[[1-(3-Hydroxy-3-phenyl-3-trifluoromethylpropionyl)-4-piperidyl]methyl]-1H-2-methylimidazo[4,5-c]pyridine Following the procedure described in example 1, but using 3-hydroxy-3-phenyl-3-trifluoromethylpropionic acid (obtained in reference example 11) instead of 3,3-diphenylpropionic acid, the title compound was obtained as a white solid (15%).

mp: 210°–211° C. ($C_{23}H_{25}F_3N_4O_2.\frac{1}{2}H_2O$);

$^1$H NMR (80 MHz, CDCl$_3$) δ (TMS): 8.90 (s, 1H), 8.36 (d, J=5.5 Hz, 1H), 7.35 (m, 6H), 4.68 (m, 1H), 4.60 (m, 1H), 3.94 (m, 3H), 2.60 (s, 3H), 3–0.5 (complex signal, 9H).

EXAMPLE 48 trans-1-[[1-[3-(4-Aminophenyl)-2-butenoyl]-4-piperidyl]methyl]-1H-2-methylimidazo[4,5-c]pyridine Following the procedure described in example 1, but using 3-(4-nitrophenyl)-2-butenoic acid (obtained in reference example 22), and hydrogenating the compound thus obtained according to the procedure described in reference example 3, the title compound was obtained as a white solid (22%).

mp: 106°–110° C. ($C_{23}H_{27}N_5O.\frac{1}{2}H_2O$);

$^1$H NMR (80 MHz, CDCl$_3$) δ (TMS): 8.98 (s, 1H), 8.38 (d, J=5.5 Hz, 1H), 7.27 m, 3H), 6.60 (d, J=8.5 Hz, 2H), 6.17 (s, 1H), 4.67 (m, 1H), 3.90 (d, J=7.2 Hz, 2H), 3.81 (m, 1H), 2.63 (s, 3H), 2.23 (s, 3H), 3.1–0.5 (complex signal, 9H).

EXAMPLE 49

1-[[1-[(Phenylamino)acetyl]-4-piperidyl]methyl]-1H-2-methylimidazo[4,5-c]pyridine Following the procedure described in example 1, but using N-tert-butoxycarbonyl-N-phenylglycine instead of 3,3-diphenylpropionic acid, and then subjecting the resulting compound to the procedure described in reference example 5, the title compound was obtained as a white solid (49%).

mp: 219°–220° C. ($C_{21}H_{25}N_5O.H_2O$);

$^1$H NMR (80 MHz, CDCl$_3$) δ (TMS): 9.00 (s, 1H), 8.40 (d, J=5.5 Hz, 1H), 7.20 (m, 4H), 6.66 (m, 2H), 4.72 (m, 2H), 3.89 (m, 5H), 2.63 (s, 3H), 3.2–1 (m, 7H).

EXAMPLE 50

(R)-1-[[1-[(1-Phenylethylamino)carbonyl]-4-piperidyl]methyl]-1H-2-methylimidazo[4,5-c]pyridine Following the procedure described in example 36, but using (R)-N-phenoxycarbonyl-1-phenylethylamine (prepared from (R)-1-phenylethylamine and phenyl chloroformate) instead of N-phenoxycarbonyl-L-Leucine ethyl ester, the title compound was obtained as a white solid (37%).

mp: 80°–84° C. ($C_{22}H_{27}N_5O.\frac{1}{2}H_2O$);

$^1$H NMR (80 MHz, CDCl$_3$) δ (TMS): 8.97 (s, 1H), 8.38 (d, J=5.5 Hz, 1H), 7.30 (m, 5H), 7.20 (d, J=5.5 Hz, 1H), 5.01 (quint, J=6.8 Hz, 1H), 4.70 (broad d, J=7.1 Hz, 1H), 4.02 (m, 1H), 3.97 (d, J=7.3 Hz, 2H), 2.68 (broad t, J=12.7 Hz, 2H) 2.62 (s, 3H), 1.48 (d, J=6.5 Hz, 3H), 2.1–1.3 (m, 6H).

EXAMPLE 51

(S)-1-[[1-[(1-Phenylethylamino)carbonyl]-4-piperidyl]methyl]-1H-2-methylimidazo[4,5-c]pyridine Following the procedure described in example 36, but using (S)-N-phenoxycarbonyl-1-phenylethylamine (prepared from (S)-1-phenylethylamine and phenyl chloroformate) instead of N-phenoxycarbonyl-L-Leucine ethyl ester, the title compound was obtained as a white solid (41%).

mp: 79°–83° C. ($C_{22}H_{27}N_5O.\frac{1}{2}H_2O$);

$^1$H NMR (80 MHz, CDCl$_3$) δ (TMS): 8.98 (s, 1H), 8.38 (d, J=5.5 Hz, 1H), 7.26 (m, 5H), 7.20 (d, J=5.5 Hz, 1H), 5.01 (quint, J=6.8 Hz, 1H), 4.68 (broad d, J=7.1 Hz, 1H), 4.02 (m, 1H), 3.97 (d, J=7.3 Hz, 2H), 2.68 (broad t, J=12.7 Hz, 2H), 2.62 (s, 3H), 1.48 (d, J=6.5 Hz, 3H), 2.1–1.3 (m, 6H).

EXAMPLE 52

1-[[1-[(N-Benzoyl-N-phenylamino)acetyl]-4-piperidyl]methyl]-1H-2-methylimidazo[4,5-c]pyridine To a cooled (0° C.) solution of the compound obtained in example 49 (0.3 g, 0.824 mmol) and Et$_3$N (0.11 mL) in CH$_2$Cl$_2$ (6 mL), was added dropwise a solution of benzoyl chloride (0.09 mL) in CH$_2$Cl$_2$ (0.2 mL) and the mixture was stirred at room temperature overnight. The resulting solution was treated with 0.5N NaOH and extracted with CH$_2$Cl$_2$ (3×). The organic phase was dried and concentrated to a residue that was purified by chromatography on silica gel (CHCl$_3$—MeOH, 8%) to afford the title compound (70%).

$^1$H NMR (80 MHz, CDCl$_3$) δ (TMS): 8.96 (m, 1H), 8.38 (m, 1H), 7.16 (m, 11H), 4.68 (m, 3H), 3.92 (m, 3H), 2.60 (s, 3H), 3.2–1.2 (m, 7H).

The hydrochloride was prepared following the procedure described in example 13.

mp: 145°–152° C. ($C_{28}H_{29}N_5O_2.3HC.H_2O$).

EXAMPLE 53

1-[[1-[[N-methyl-N-(4-nitrobenzenesulfonyl)amino]acetyl]-4-piperidyl]methyl]-1H-2-methylimidazo[4,5-c]pyridine Following the procedure described in example 52, but starting from the compound obtained in example 46b) and using 4-nitrobenzenesulfonyl chloride instead of benzoyl chloride, the title compound was obtained as a white solid (48%).

mp: 98°–104° C. ($C_{22}H_{26}N_6O_5S.H_2O$);

$^1$H NMR (80 MHz, CDCl$_3$) δ (TMS): 8.99 (s, 1H), 8.39 (d, J=5.5 Hz, 1H), 8.36 (d, J=6.9 Hz, 2H), 7.99 (d, J=6.9 Hz, 2H), 7.22 (d, J=5.5 Hz, 1H), 4.52 (m, 1H), 3.97 (m, 5H), 2.89 (s, 3H), 2.64 (s, 3H), 3.2–1.3 (m, 7H).

EXAMPLE 54

1-[[1-[[N-Ethoxycarbonyl-N-(4-nitrophenyl)amino]acetyl]-4-piperidyl]methyl]-1H-2-methylimidazo[4,5-c]pyridine Following the procedure described in example 1, but using N-ethoxycarbonyl-N-(4-nitrophenyl)aminoacetic acid (obtained in reference example 23) instead of 3,3-diphenylpropionic acid, the title compound was obtained as a white solid (64%).

$^1$H NMR (80 MHz, CDCl$_3$) δ (TMS): 8.96 (s, 1H), 8.37 (d, J=5.5 Hz, 1H), 8.13 (d, J=7.05 Hz, 2H), 7.48 (d, J=7.05 Hz, 2H), 7.21(d, J=5.5 Hz, 1H), 4.65 (m, 1H), 4.51 (d, J=4.3 Hz, 2H), 4.22 (q, J=7.1 Hz, 2H), 4.02 (d, J=7.2 Hz, 2H), 3.80 (m, 1H), 2.63 (s, 3H), 3.1–1.3 (m, 7H), 1.24 (t, J=7.1 Hz, 3H).

EXAMPLE 55

1-[[1-[[N-(4-Aminophenyl)-N-ethoxycarbonylamino]acetyl]-4-piperidyl]methyl]-1H-2-methylimidazo[4,5-c]pyridine Following the procedure described in reference example 3, but starting from the compound obtained in example 54, the title compound was obtained as a white solid (74%).

mp: 137°–138° C. (C$_{24}$H$_{30}$N$_6$O$_3$.H$_2$O);

$^1$H NMR (80 MHz, CDCl$_3$) δ (TMS): 8.98 (s, 1H), 8.40 (d, J=5.5 Hz, 1H), 7.20 (d, J=5.5 Hz, 1H), 7.10 (d, J=7.05 Hz, 2H), 6.60 (d, J=7.05 Hz, 2H), 4.65 (m, 1H), 4.30 (m 2H), 4.10 (m, 4H), 3.80 (m, 3H), 2.62 (s, 3H), 3.1–1.3 (m, 7H), 1.17 (t, J=6.9 Hz, 3H).

EXAMPLE 56 trans -1-[[1-(3-Phenyl-2-pentenoyl)-4-piperidyl]methyl]-1H-2-methylimidazo[4,5-c]pyridine Following the procedure described in example 1, but using trans-3-phenyl-2-pentenoic acid (obtained in reference example 24) instead of 3,3-diphenylpropionic acid, the title compound was obtained as a white solid (74%).

mp: 59°–62° C. (C$_{24}$H$_{28}$N$_4$O.½H$_2$O);

$^1$H NMR (80 MHz, CDCl$_3$) δ (TMS): 8.99 (s, 1H), 8.40 (d, J=5.5 Hz, 1H), 7.36 (m, 5H), 7.20 (d, J=5.5 Hz, 1H), 6.09 (s, 1H), 4.75 (m, 1H), 4.05 (m, 1H), 4.01 (d, J=7.1 Hz, 2H), 2.72 (q, J=7.4 Hz, 2H), 2.64 (s, 3H), 3.1–1.3 (m, 7H), 1.02 (t, J=7.4 Hz, 3H).

EXAMPLE 57

1-[[1-[[N-(2-Methoxybenzyl)amino]carbonyl]-4-piperidyl]methyl]-1H-2-methylimidazo[4,5-c]pyridine Following the procedure described in example 36, but using N-phenoxycarbonyl-N-(2-methoxybenzyl)amine (prepared from 2-methoxybenzylamine and phenyl chloroformate) instead of N-phenoxycarbonyl-L-Leucine ethyl ester, the title compound was obtained as a white solid (17%).

mp: 76°–85° C. (C$_{22}$H$_{27}$N$_5$O$_2$);

$^1$H NMR (80 MHz, CDCl$_3$) δ (TMS): 8.96 (s, 1H), 8.35 (d, J=5.5 Hz, 1H), 7.25 (m, 3H), 7.89 (t, J=7.2 Hz, 2H), 5.14 (t, J=5.3 Hz, 1H), 4.40 (d, J=5.6 Hz, 2H), 3.91 (m, 4H), 3.82 (s, 3H), 2.60 (s, 3H), 2.8–1.3 (m, 7H).

EXAMPLE 58

(R)-1-[[1-[[(1-Ethoxycarbonyl-1-phenyl)methylamino]carbonyl]-4-piperidyl]methyl]-1H-2-methylimidazo[4,5-c]pyridine Following the procedure described in example 36, but using (R)-N-phenoxycarbonyl-2-phenylglycine ethyl ester (prepared from (R)-2-phenylglycine ethyl ester and phenyl chloroformate) instead of N-phenoxycarbonyl-L-Leucine ethyl ester, the title compound was obtained as a white solid (27%).

mp: 78°–80° C. (C$_{24}$H$_{29}$N$_5$O$_3$.½H$_2$O);

$^1$H NMR (80 MHz, CDCl$_3$) δ (TMS): 8.96 (s, 1H), 8.35 (d, J=5.5 Hz, 1H), 7.33 (s, 5H), 7.19 (d, J=5.5 Hz, 1H), 5.52 (m, 2H), 4.13 (m, 6H), 2.71 (m 2H), 2.60 (s, 3H), 2.10 (m, 1H), 1.45 (m, 4H), 1.19 (t, J=7.1 Hz, 3H).

EXAMPLE 59

1-[[1-[(1-Phenyl-1-cyclopropylamino)carbonyl]-4-piperidyl]methyl]-1H-2-methylimidazo[4,5-c]pyridine To a solution of 1-phenyl-1-cyclopropanecarboxylic acid (1.62 g, 0.01 mol) and Et$_3$N (1.14 mL) in benzene (40 mL) was added dropwise diphenylphosphorylazide (2.14 mL). The mixture was heated at 90° C.for 2 h. The compound obtained in reference example 5 (1.6 g, 6.8 mmol) was then added and the mixture was heated at 90° C. overnight. After cooling, 1N NaOH was added and it was extracted with EtOAc (3×). The organic phase was dried and concentrated to a residue which was purified by chromatography on silica gel (CHCl$_3$—MeOH, 10%) to afford the title compound as a white solid (1.24 g, 47%).

mp: 227°–228° C. (C$_{23}$H$_{27}$N$_5$O);

$^1$H NMR (80 MHz, CDCl$_3$) δ (TMS): 8.98 (s, 1H), 8.38 (d, J=5.5 Hz, 1H), 7.23 (s, 6H), 5.44 (s, 1H), 4.02 (m, 2H), 3.97 (d, J=8.0 Hz, 2H), 2.64 (m 2H), 2.62 (s, 3H), 2.10 (m, 1H), 1.55 (m, 4H), 1.22 (s, 4H).

EXAMPLE 60

(S)-1-[[1-[(2-Ethoxy-1-phenylethylamino)carbonyl]-4opiperidyl]methyl]-1H-2-methylimidazo[4,5-c]pyridine Following the procedure described in example 36, but using (S)-N-phenoxycarbonyl-2-phenylglycinol ethyl ether (prepared from 2-phenylglydnol ethyl ether and phenyl chloroformate) instead of N-phenoxycarbonyl-L-Leucine ethyl ester, the title compound was obtained as a white solid (24%).

mp: 68°–70° C. (C$_{24}$H$_{31}$N$_5$O$_2$);

$^1$H NMR (80 MHz, CDCl$_3$) δ (TMS): 8.97 (s, 1H), 8.38 (d, J=5.5 Hz, 1H), 7.29 (s, 5H), 7.21 (d, J=5.5 Hz, 1H), 5.36 (d, J=6.4 Hz, 1H), 5.01 (q, J=5.4 Hz, 1H), 4.05 (m, 2H), 3.96 (d, J=7.1 Hz, 2H), 3.54 (m, 4H), 2.75 (m, 2H), 2.61 (s, 3H), 2.10 (m, 1H), 1.45 (m, 4H), 1.15 (t, J=6.9 Hz, 3H).

EXAMPLE 61

1-[[1-[(2-Methyl-2-phenylpropyl)sulfonyl]-4-piperidyl]methyl]-1H-2-methylimidazo[4,5-c]pyridine To a solution of the compound obtained in reference example 5 (1 g, 4 mmol) and Et$_3$N (0.6 mL) in CHCl$_3$ (20 mL), was added 2-methyl-2-phenylpropylsulfonyl chloride (2.32 g, 10 mmol, obtained in reference example 25) and the mixture was stirred at room temperature overnight. The resulting solution was diluted with $CHCl_3$, washed with 0.5N NaOH, dried and concentrated. The residue was purified by chromatography on silica gel ($CHCl_3$—MeOH, 5%) to afford a solid which was recrystallized from hot EtOAc. The title compound was obtained as a white solid (0.4 g, 25%).

mp: 165°–166° C. ($C_{23}H_{30}N_4O_2S$);

$^1$H NMR (80 MHz, $CDCl_3$) δ (TMS): 8.98 (s, 1H), 8.38 (d, J=5.5 Hz, 1H), 7.32 (m, 5H), 7.17 (d, J=5.5 Hz, 1H), 3.94 (d, J=6.9 Hz, 2H), 3.65 (broad d, J=12.0Hz), 3.16 (s, 2H), 2.60 (s, 3H), 2.18 (broad t, J=12.0 Hz, 2H), 1.58 (s, 6H), 1.48 (m, 5H).

EXAMPLE 62

1-[[1-(3-Phenylpropionyl)-4-piperidyl]methyl]-1H-2-methylimidazo[4,5-c]pyridine

Following the procedure described in example 1, but using 3-phenylpropionic acid instead of 3,3-diphenylpropionic acid, the title compound was obtained as a white solid.

mp: 52°–58° C. ($C_{22}H_{26}N_4O·¾H_2O$);

$^1$H NMR (80 MHz, $CDCl_3$) δ (TMS): 8.96 (s, 1H), 8.38 (d, J=5.5 Hz, 1H), 7.23 (m, 6H), 4.71 (broad d, J=13.6 Hz, 1H), 3.94 (d, J=7.21 Hz, 2H), 3.56 (broad d, J=13.6 Hz, 1H), 2.80 (m, 2H), 2.62 (m, 2H), 2.61 (s, 3H), 2.7–0.8 (m, 7H).

EXAMPLE 63

1-[[1-[[1-(4-Nitrophenyl)ethylamino]carbonyl]-4-piperidyl]methyl]-1H-2-methylimidazo[4,5-c]pyridine Following the procedure described in example 59, but using 2-(4-nitrophenyl)propionic acid instead of 1-phenyl-1-cyclopropanecarboxylic acid, the title compound was obtained as a white solid (57%).

$^1$H NMR (80 MHz, $CDCl_3$) δ (TMS): 8.95 (s, 1H), 8.35 (d, J=5.5 Hz, 1H), 8.22 (d, J=9.1 Hz, 2H), 7.45 (d, J=9.1 Hz, 2H), 7.20 (d, J=5.5 Hz, 1H), 5.03 (m, 2H), 4.05 (m, 2H), 3.96 (d, J=7.1 Hz, 2H), 2.71 (m, 2H), 2.62 (s, 3H), 1.48 (d, J=6.6 Hz, 3H), 2.2–1.0 (m, 5H).

EXAMPLE 64

1-[[1-[[1-(4-Aminophenyl)ethylamino]carbonyl]-4-piperidyl]methyl]-1H-2-methylimidazo[4,5-c]pyridine A solution of the compound obtained in example 63 (0.8 g, 1.89 mmol) and $SnCl_2·2H_2O$ (2.128 g, 9.4 mmol) in EtOH (25 mL) was heated at 60° C. and then a solution of $NaBH_4$ (0.035 g, 0.94 mmol) in EtOH (15 mL) was added dropwise. The reaction mixture was heated at 60° C. for 1 h and was then cooled to 10° C., made basic and extracted with $CHCl_3$, washing with water. The organic phase was dried and concentrated to a residue which was chromatographed on silica gel ($CHCl_3$:MeOH:$NH_3$, 60:20:0.2) to afford the title compound (27 mg, 4%).

mp: 122°–128° C. ($C_{22}H_{28}N_6O·½H_2O$);

$^1$H NMR (80 MHz, $CDCl_3$) δ (TMS): 8.96 (s, 1H), 8.36 (d, J=5.5 Hz, 1H), 7.18 (d, J=5.5 Hz, 1H), 7.11 (d, J=8.3 Hz, 2H), 6.62 (d, J=8.3 Hz, 2H), 4.90 (quint, J=6.7 Hz, 1H), 3.96 (d, J=6.4 Hz, 1H), 3.96 (m, 4H), 2.64 (m, 2H), 2.61 (s, 3H), 2.10 (m, 1H), 1.43 (d, J=6.6 Hz, 3H), 1.26 (m, 6H).

EXAMPLE 65 trans-1-[[1-[3-(4-Aminophenyl)propenoyl]-4-piperidyl]methyl]-1H-2-methylimidazo[4,5-c]pyridine Following the procedure described in example 1, but using trans-4-aminocinnamic acid hydrochloride instead of 3,3-diphenylpropionic acid, the title compound was obtained as a white solid (71%).

mp: 115°–120° C. ($C_{22}H_{25}N_5O·½H_2O$);

$^1$H NMR (80 MHz, $CDCl_3$) δ (TMS): 8.99 (s, 1H), 8.40 (d, J=5.5 Hz, 1H), 7.62 (d, J=15.3 Hz, 1H), 7.32 (d, J=8.4 Hz, 2H), 7.20 (d, J=5.5 Hz, 1H), 6.64 (d, J=15.3 Hz, 1H), 6.63 (d, J=8.3 Hz, 2H), 4.40 (m, 1H), 4.00 (d, J=7.3 Hz, 2H), 3.94 (m, 1H), 2.80 (m, 2H), 2.64 (s, 3H), 2.4–1.2 (m, 7H).

EXAMPLE 66

1-[[1-[[N-(2-Methoxyphenyl)-N-methylamino]acetyl]-4-piperidyl]methyl]-1H-2-methylimidazo[4,5-c]pyridine Following the procedure described in example 1, but using [N-(2-methoxyphenyl)-N-methylamino]acetic acid (obtained in reference example 26) instead of 3,3-diphenylpropionic acid, the title compound was obtained as a white solid (71%).

mp: 59°–64° C. ($C_{23}H_{29}N_5O_2·½H_2O$);

$^1$H NMR (80 MHz, $CDCl_3$) δ (TMS): 8.98 (s, 1H), 8.38 (d, J=5.5 Hz, 1H), 7.20 (d, J=5.5 Hz, 1H), 7.06 (m, 3H), 4.45 (m, 1H), 4.42 (m, 1H), 3.97 (m, 4H), 3.82 (s, 3H), 2.87 (s, 3H), 2.63 (m, 3H), 2.62 (s, 3H), 2.4–1.2 (m, 5H).

EXAMPLE 67

1-[[1-[[4-(tert-Butoxycarbonylamino)phenylmethylamino]carbonyl]-4-piperidyl]methyl]-1H-2-methylimidazo[4,5-c]pyridine Following the procedure described in example 59, but using 4-(N-tert-butoxycarbonylamino)phenylacetic acid instead of 1-phenyl-1-cyclopropanecarboxylic acid, the title compound was obtained as a white solid (94%).

mp: 125°–130° C. ($C_{26}H_{34}N_6O_3·½H_2O$);

$^1$H NMR (80 MHz, $CDCl_3$) δ (TMS): 8.96 (s, 1H), 8.36 (d, J=5.5 Hz, 1H), 7.28 (m, 5H), 6.90 (s, 1H), 5.05 (m, 1H), 4.31 (d, J=5.2 Hz, 2H), 4.03 (m, 2H), 3.96 (d, J=7.1 Hz, 2H), 2.62 (m, 2H), 2.60 (s, 3H), 2.1–1.2 (m, 5H), 1.50 (s, 9H).

EXAMPLE 68

1-[[1-[(4-Aminophenylmethylamino)carbonyl]-4-piperidyl]methyl]-1H-2-methylimidazo[4,5-c]pyridine Following the procedure described in reference example 5, but starting from the compound obtained in example 67, the title compound was obtained as a white solid (70%).

mp: 104°–109° C. ($C_{21}H_{26}N_6O·H_2O$);

$^1$H NMR (80 MHz, $CDCl_3$) δ (TMS): 8.92 (s, 1H), 8.34 (d, J=5.5 Hz, 1H), 7.19 (d, J=5.5 Hz, 1H), 7.05 (d, J=8.2 Hz, 2H), 6.58 (d, J=8.2 Hz, 2H), 5.05 (m, 1H, 4.26 (d, J=5.2 Hz, 2H), 4.08 (m, 2H), 3.96 (d, J=7.1 Hz, 2H), 3.40 (m, 2H), 2.60 (m, 2H), 2.59 (s, 3H), 2.1–1.2 (m, 5H).

EXAMPLE 69

1-[[1-[3-(2-Methoxyphenyl)propionyl]-4-piperidyl]methyl]-1H-2-methylimidazo[4,5-c]pyridine Following the procedure described in example 1, but using 3-(2-methoxyphenyl)propionic acid instead of 3,3- diphenylpropionic acid, the title compound was obtained as a white solid (20%).

mp: 54°–56° C. ($C_{23}H_{28}N_4O_2 \cdot \frac{1}{2}H_2O$);

$^1$H NMR (80 MHz, CDCl$_3$) δ (TMS): 8.97 (s, 1H), 8.37 (d, J=5.5 Hz, 1H), 7.15 (m, 3H), 6.86 (m, 2H), 4.71 (broad d, J=13.6 Hz, 1H), 3.94 (d, J=7.21 Hz, 2H), 3.18 (m, 1H), 3.80 (s, 3H), 2.97 (m, 2H), 2.62 (s, 3H), 2.61 (m, 4H), 2.3–0.8 (m, 5H).

EXAMPLE 70

1-[[1-[[(1-Phenyl-1-cyclopropyl)methoxy]carbonyl]-4-piperidyl]methyl]-1H-2-methylimidazo[4,5-c]pyridine Following the procedure described in example 36, but using phenyl (1-phenyl-1-cyclopropyl)methyl carbonate (prepared from 1-phenyl-1-cyclopropanemethanol and phenyl chloroformate) instead of N-phenoxycarbonyl-L-Leucine ethyl ester, the title compound was obtained as a white solid (23%).

mp: 138°–140° C. ($C_{24}H_{28}N_4O_2 \cdot \frac{1}{2}H_2O$);

$^1$H NMR (80 MHz, CDCl$_3$) δ (TMS): 8.97 (s, 1H), 8.37 (d, J=5.5 Hz, 1H), 7.27 (m, 5H), 7.19 (d, J=5.5 Hz, 1H), 4.16 (s, 2H), 4.15 (broad d, J=13.6 Hz, 2H), 3.94 (d, J=7.21 Hz, 2H), 2.60 (s, 3H), 2.60 (m, 2H), 2.3–0.8 (m, 5H), 0.92 (s, 4H).

EXAMPLE 71 trans-1-[[1-[3-(Methoxymethyl)-3-phenylpropenoyl]-4-piperidyl]methyl]-1H-2-methylimidazo[4,5-c]pyridine Following the procedure described in example 1, but using trans-3-(methoxymethyl)-3-phenylpropenoic acid (obtained in reference example 27) instead of 3,3-diphenylpropionic acid, the title compound was obtained as a white solid.

mp: 63°–67° C. ($C_{24}H_{28}N_4O_2 \cdot H_2O$);

$^1$H NMR (80 MHz, CDCl$_3$) δ (TMS): 8.98 (s, 1H), 8.40 (d, J=5.5 Hz, 1H), 7.27 (m, 5H), 7.18 (d, J=5.5 Hz, 1H), 6.39 (s, 1H), 4.60 (m, 1H), 3.98 (m, 1H), 3.96 (d, J=7.2 Hz, 2H), 3.71 (s, 3H), 3.54 (d, J=7.2 Hz, 2H), 2.60 (s, 3H), 3.1–1.3 (m, 7H).

EXAMPLE 72

1-[[1-[[N-(4-Nitrophenylsulfonyl)-N-phenylamino]acetyl]-4-piperidyl]methyl]-1H-2-methylimidazo[4,5-c]pyridine To a solution of the compound obtained in example 49 (2.5 g, 6.9 mmol) in pyridine was added 4-nitrobenzenesulfonyl chloride (1.54 g) and the resulting mixture was heated at 60° C. for 18 h. The solvent was removed and the residue partitioned between 0.5N NaOH and CHCl$_3$. The organic phase was dried and concentrated to a residue which was chromatographed on silica gel (CHCl$_3$:MeOH, 10%) to afford the title compound as a yellow solid (2.93 g, 78%).

mp: 110°–115° C. ($C_{27}H_{28}N_6O_5S \cdot \frac{1}{2}H_2O$);

$^1$H NMR (80 MHz, CDCl$_3$) δ (TMS): 9.00 (s, 1H), 8.40 (d, J=5.5 Hz, 1H), 8.26 (d, J=8.8 Hz, 2H), 7.84 (d, J=8.8 Hz, 2H), 7.27 (m, 5H), 7.18 (d, J=5.5 Hz, 1H), 4.70 (m, 1H), 4.52 (s, 2H), 4.00 (d, J=7.2 Hz, 2H), 3.80 (m, 1H), 2.64 (s, 3H), 3.1–1.3 (m, 7H).

EXAMPLE 73

1-[[1-[[N-(4-Aminophenylsulfonyl)-N-phenylamino]acetyl]-4-piperidyl]methyl]-1H-2-methylimidazo[4,5-c]pyridine Following the procedure described in reference example 3, but starting from the compound obtained in example 72, the title compound was obtained as a white solid (78%).

mp: 147°–157° C. ($C_{27}H_{30}N_6O_3S \cdot H_2O$);

$^1$H NMR (80 MHz, CDCl$_3$) δ (TMS): 8.79 (s, 1H), 8.38 (d, J=5.5 Hz, 1H), 7.45 (d, J=8.8 Hz, 2H), 7.26 (m, 6H), 6.94 (d, J=8.8 Hz, 2H), 4.36 (m, 1H), 4.35 (s, 2H), 4.00 (d, J=7.2 Hz, 2H), 3.98 (m, 1H), 2.63 (s, 3H), 3.3–1.0 (m, 9H).

EXAMPLE 74

1-[[1-[(2-Methyl-2-phenylpropylamino)carbonyl]-4-piperidyl]methyl]-1H-2-methylimidazo[4,5-c]pyridine Following the procedure described in example 59, but using 3-methyl-3-phenylbutanoic acid (obtained in reference example 19) instead of 1-phenyl-1-cyclopropanecarboxylic acid, the title compound was obtained as a white solid (36%).

mp: 66°–69° C. ($C_{24}H_{31}N_5O \cdot \frac{1}{2}H_2O$);

$^1$H NMR (80 MHz, CDCl$_3$) δ (TMS): 8.98 (s, 1H), 8.39 (d, J=5.5 Hz, 1H), 7.25 (m, 5H), 7.18 (d, J=5.5 Hz, 1H), 4.08 (m, 1H), 3.94 (d, J=7.3 Hz, 2H), 3.78 (broad d, J=6.0 Hz, 2H), 3.43 (d, J=5.7 Hz, 2H), 2.61 (s, 3H), 2.60 (m, 2H), 2.1–0.8 (m, 5H), 1.33 (s, 6H).

EXAMPLE 75

1-[[1-[[N-Isobutyl-N-(4-nitrophenylsulfonyl)amino]acetyl]-4-piperidyl]methyl]-1H-2-methylimidazo[4,5-c]pyridine Following the procedure described in example 1, but using N-isobutyl-N-(4-nitrophenylsulfonyl)aminoacetic acid (obtained in reference example 28) instead of 3,3-diphenylpropionic acid, the title compound was obtained as a white solid (71%).

$^1$H NMR (80 MHz, CDCl$_3$) δ (TMS): 8.98 (s, 1H), 8.40 (d, J=5.5 Hz, 1H), 8.31 (d, J=8.8 Hz, 2H), 8.00 (d, J=8.8 Hz, 2H), 7.21 (d, J=5.5 Hz, 1H), 4.50 (m, 1H), 4.16 (s, 2H), 4.01 (d, J=7.2 Hz, 2H), 3.85 (m, 1H), 3.08 (d, J=7.4 Hz, 2H), 2.63 (s, 3H), 3.1–1.2 (m, 8H), 0.87 (d, J=6.5 Hz, 6H).

EXAMPLE 76

1-[[1-[[N-(4-Aminophenylsulfonyl)-N-isobutylamino]acetyl]-4-piperidyl]methyl]-1H-2-methylimidazo[4,5-c]pyridine Following the procedure described in reference example 3, but starting from the compound obtained in example 75, the title compound was obtained as a white solid (67%).

mp: 112°–116° C. ($C_{25}H_{34}N_6O_3S \cdot \frac{1}{2}H_2O$);

$^1$H NMR (80 MHz, CDCl$_3$) δ (TMS): 8.96 (s, 1H), 8.39 (d, J=5.5 Hz, 1H), 7.51 (d, J=8.8 Hz, 2H), 7.20 (d, J=5.5 Hz, 1H), 6.63 (d, J=8.8 Hz, 2H), 4.50 (m, 3H), 3.89 (m, 5H), 3.00 (m, 2H), 2.62 (s, 3H), 3.1–1.2 (m, 8H), 0.84 (d, J=6.5 Hz, 6H).

We claim:

1. A compound of formula I:

wherein:

m represents 0, 1 or 2;

a, b and c represent CR, wherein each R independently represents hydrogen or $C_{1-4}$ alkyl;

$R^1$ represents $C_{1-4}$ alkyl or $C_{3-7}$ cycloalkyl;

A represents —CO—, —SO$_2$—, —NHCO— or —OCO—;

B represents a group of formula (i), and when A represents —CO— or —SO$_2$—, then B can also represent a group of formula (ii) or (iii)

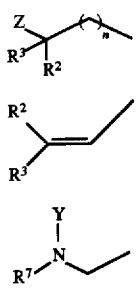

(i)

(ii)

(iii)

n represents 0, 1, 2 or 3;

one of $R^2$ or $R^3$ represents $C_{1-4}$ alkyl, $C_{3-7}$ cycloalkyl or aryl, and the other represents hydrogen, $C_{1-4}$ alkyl, $C_{1-4}$ haloalkyl, $C_{3-7}$ cycloalkyl, $C_{1-4}$ alkoxy-$C_{1-4}$ alkyl, aryl or aryl-$C_{1-4}$ alkyl;

Z represents hydrogen, $C_{1-4}$ alkyl, —CH$_2$—OR$^4$, —COOR$^4$ or —CONR$^4$R$^5$, and when A represents —CO— or —SO$_2$—, then Z can also be hydroxy, —NR$^4$R$^5$, —NR$^6$C(=O)OR$^4$, —NR$^6$C(=O)R$^4$, —NR$^6$C(=O)NR$^4$R$^5$, —N(OH)C(=O)NR$^4$R$^5$ or —NR$^6$SO$_2$R$^4$;

or Z and $R^3$ together form a $C_{2-5}$ polymethylene chain in which case $R^2$ represents $C_{1-4}$ alkyl, $C_{3-7}$ cycloalkyl or aryl;

$R^4$ represents hydrogen, $C_{1-4}$ alkyl, aryl or aryl-$C_{1-4}$ alkyl;

$R^5$ and $R^6$ independently represent hydrogen or $C_{1-4}$ alkyl;

$R^7$ represents $C_{1-4}$ alkyl, $C_{3-7}$ cycloalkyl, aryl, aryl-$C_{1-4}$ alkyl or bisaryl-$C_{1-4}$ alkyl;

Y represents hydrogen, $C_{1-4}$ alkyl, aryl, aryl-$C_{1-4}$ alkyl, —C(=O)OR$^4$, —C(=O)R$^4$, —C(=O)NR$^4$R$^5$, or —SO$_2$R$^4$;

aryl, whenever appearing in the above definitions, represents phenyl or phenyl substituted with 1, 2, 3 or 4 groups independently selected from halogen, $C_{1-4}$ alkyl, $C_{1-4}$ alkoxy, hydroxy, $C_{1-4}$ haloalkyl, $C_{1-4}$ haloalkoxy, cyano, nitro, amino, $C_{1-4}$ alkylamino, $C_{1-4}$ dialkylamino, $C_{1-4}$ alkylcarbonyl, $C_{1-4}$ alkylcarbonyloxy, $C_{1-4}$ alkoxycarbonyl, $C_{1-4}$ alkylsulfonyl, $C_{1-4}$ alkylsulfinyl, $C_{1-4}$ alkylthio, $C_{1-4}$ alkylcarbonylamino or $C_{1-4}$ alkoxycarbonylamino; and the salts and solvates thereof.

2. A compound as claimed in claim 1 wherein m represents 1 or 2.

3. A compound as claimed in claim 1 wherein A represents —CO— or —SO$_2$—.

4. A compound as claimed in claim 1 wherein A represents —NHCO— or —OCO—.

5. A compound as claimed in claim 1 wherein B represents a group of formula (i).

6. A compound as claimed in claim 1 wherein n represents 0, 1 or 2.

7. A compound as claimed in claim 1 wherein B represents a group of formula (ii).

8. A compound as claimed in claim 1 wherein B represents a group of formula (iii).

9. A compound as claimed in claim 1 wherein Z represents hydrogen, $C_{1-4}$ alkyl, —CH$_2$—OR$^4$, —COOR$^4$, or —CONR$^4$R$^5$, and when A represents —CO— or —SO$_2$—, Z can also represent hydroxy, —NR$^6$C(=O)OR$^4$, —NR$^6$C(=O)R$^4$ or —NR$^6$SO$_2$R$^4$; or Z and $R^3$ together form a $C_{2-5}$ polymethylene chain.

10. A compound as claimed in claim 1 wherein $R^7$ represents $C_{1-4}$ alkyl, $C_{3-7}$ cycloalkyl or aryl.

11. A compound as claimed in claim 1 wherein aryl represents phenyl or phenyl substituted with 1, 2, 3 or 4 groups independently selected from halogen, $C_{1-4}$ alkyl, $C_{1-4}$ alkoxy, hydroxy, $C_{1-4}$ haloalkyl, $C_{1-4}$ haloalkoxy or amino.

12. A compound as claimed in claim 1 wherein:

A represents —CO— or —SO$_2$—;

B represents a group of formula (i), (ii) or (iii);

n represents 1 or 2;

one of $R^2$ or $R^3$ represents $C_{1-4}$ alkyl, $C_{3-7}$ cycloalkyl or aryl, and the other represents hydrogen, $C_{1-4}$ alkyl, $C_{1-4}$ haloalkyl, $C_{3-7}$ cycloalkyl, $C_{1-4}$ alkoxy-$C_{1-4}$ alkyl, aryl-$C_{1-4}$ or aryl-$C_{1-4}$-alkyl;

Z represents hydrogen, $C_{1-4}$ alkyl, —CH$_2$—OR$^4$, —COOR$^4$, —CONR$^4$R$^5$, hydroxy, —NR$^6$C(=O)OR$^4$, —NR$^6$C(=O)R$^4$ or —NR$^6$SO$_2$R$^4$;

or Z and $R^3$ together form a $C_{2-5}$ polymethylene chain in which case $R^2$ represents $C_{1-4}$ alkyl, $C_{3-7}$ cycloalkyl or aryl;

$R^7$ represents $C_{1-4}$ alkyl, $C_{3-7}$ cycloalkyl or aryl; and aryl represents phenyl or phenyl substituted with 1, 2, 3 or 4 groups independently selected from halogen, $C_{1-4}$ alkyl, $C_{1-4}$ alkoxy, hydroxy, $C_{1-4}$ haloalkyl, $C_{1-4}$ haloalkoxy or amino.

13. A compound as claimed in claim 1 wherein:

A represents

NHCO— or —OCO—;

B represents a group of formula (i);

n represents 0 or 1; and aryl represents phenyl or phenyl substituted with 1, 2, 3 or 4 groups independently selected from halogen, $C_{1-4}$ alkyl, $C_{1-4}$ alkoxy, hydroxy, $C_{1-4}$ haloalkyl, $C_{1-4}$ haloalkoxy or amino.

14. A compound as claimed in claim 12 wherein:

B represents a group of formula (i) or (iii);

one of $R^2$ or $R^3$ represents $C_{1-4}$ alkyl, $C_{3-7}$ cycloalkyl or aryl, and the other represents hydrogen, $C_{1-4}$ alkyl, $C_{1-4}$ haloalkyl, $C_{3-7}$ cycloalkyl, $C_{1-4}$ alkoxy-$C_{1-4}$ alkyl, aryl or aryl-$C_{1-4}$ alkyl;

Z represents hydrogen, $C_{1-4}$ alkyl, —CH$_2$—OR$^4$, —COOR$^4$ or hydroxy;

or Z and $R^3$ together form a $C_{2-5}$ polymethylene chain in which case $R^2$ represents $C_{1-4}$ alkyl, $C_{3-7}$ cycloalkyl or aryl;

$R^4$ represents hydrogen, $C_{1-4}$ alkyl, aryl or aryl-$C_{1-4}$ alkyl;

$R^7$ represents $C_{1-4}$ alkyl, $C_{3-7}$ cycloalkyl, or aryl; and

Y represents $C_{1-4}$ alkyl, aryl or —SO$_2$R$^4$.

15. A compound as claimed in claim 12 wherein:

B represents a group of formula (ii); and one of $R^2$ or $R^3$ represents $C_{1-4}$ alkyl or aryl, and the other represents hydrogen, $C_{1-4}$ alkyl, $C_{1-4}$ alkoxy-$C_{1-4}$ alkyl, aryl or aryl-$C_{1-4}$ alkyl.

16. A compound according to claim 1 selected from:

1-[[1-(3,3-diphenylpropionyl)-4-piperidyl]methyl]-1H-2-methylimidazo[4,5-c]pyridine;

1-[[1-[3-[N-(4-aminobenzoyl)amino]-3-phenylpropionyl]-4-piperidyl]methyl]-H-2-methylimidazo[4,5-c]pyridine;

cis-1-[[1-[3-(4-aminophenyl)-3-phenylpropenoyl]-4-piperidyl]methyl]-1H-2methylimidazo[4,5-c]pyridine;

trans-1-[[1-[3-(4-aminophenyl)-3-phenylpropenoyl]-4-piperidyl]methyl]-1H-2-methylimidazo[4,5-c]pyridine;

1-[[1-(3-hydroxy-3-phenylbutanoyl)-4-piperidyl]methyl]-1H-2-methylimidazo-[4,5-c]pyridine;

1-[[1-[2-(4-aminophenyl)propionyl]-4-piperidyl]methyl]-1H-2-methylimidazo-[4,5-c]pyridine;

1-[[1-(3-phenylhexanoyl)-4-piperidyl]methyl]-1H-2-methylimidazo[4,5-c]pyridine;

(S)-1-[[1-[[N-(1-ethoxycarbonyl-1-phenylmethyl)amino]carbonyl]-4-piperimethyl]-1H-2-methylimidazo[4,5-c]pyridine;

1-[[1-(3-phenylbutanoyl)-4-piperidyl]methyl]-1H-2-methylimidazo[4,5-c]pyridine;

1-[[1-(3-methyl-3-phenylbutanoyl)-4-piperidyl]methyl]-1H-2-methylimidazo[4,5-c]pyridine;

1-[[1-[3-(4-aminophenyl)-3-methylbutanoyl]-4-piperidyl]methyl]-1H-2-methyl-imidazo[4,5-c]pyridine;

1-[[1-(3-hydroxy-3-phenyl-3-trifluoromethylpropionyl)-4-piperidyl]methyl]-1H-2-methylimidazo[4,5-c]pyridine;

(R)-1-[[1-[(1-phenylethylamino)carbonyl]-4-piperidyl methyl]-1H-2-methylimidazo[4,5-c]pyridine;

1-[[1-[(1-phenyl-1-cyclopropylamino)carbonyl]-4-piperidyl]methyl]-1H-2-methyl-imidazo [4,5-c]pyridine;

(S)-1-[[1-[(2-ethoxy-1-phenylethylamino)carbonyl]-4-piperidyl]methyl]-1H-2-methylimidazo[4,5-c]pyridine;

1-[[1-[[N-(2-methoxyphenyl)-N-methylamino]acetyl]-4-piperidyl]methyl]-1H-2-methylimidazo[4,5-c]pyridine;

1-[[1-[[(1-phenyl-1-cyclopropyl)methoxy]carbonyl]-4-piperidyl]methyl]-1H-2-methylimidazo[4,5-c]pyridine;

1-[[1-[[N-(4-aminophenylsulfonyl)-N-phenylamino]acetyl]-4-piperidyl]methyl]-1H-2-methylimidazo[4,5-c]pyridine;

1-[[1-[[N-(4-aminophenylsulfonyl)-N-isobutylamino]acetyl]-4-piperidyl]methyl]-1H-2-methylimidazo[4,5-c]pyridine; or a salt or solvate thereof.

17. A pharmaceutical composition which comprises an effective amount of a compound of formula I as claimed in claim 1 or a pharmaceutically acceptable salt or solvate thereof and a pharmaceutically acceptable excipient.

18. A process for preparing a compound of formula I as defined in claim 1 which comprises:

(A) reacting a compound of formula II,

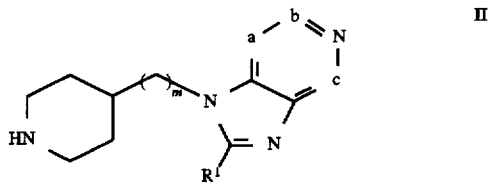

wherein a, b, c, m and $R^1$ are as defined in claim 1, with an acid of formula BCOOH (III) or a suitable derivative thereof such as the acid chloride or the anhydride, a sulfonyl chloride of formula $BSO_2C_1$ (IV), a compound of formula BOC(=O)G (V), a compound of formula BNHC(=O)G (VI) or a compound of formula BN=C=O (VII), wherein B is as defined in claim 1 and G represents a good leaving group such as chloro or —OPh; or (B) converting in one or a plurality of steps a compound of formula I into another compound of formula I; and (C) if desired, after steps A or B, reacting a compound of formula I with an acid to give the corresponding acid addition salt.

19. A compound of formula II

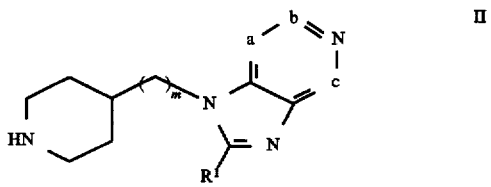

wherein a, b, c, m and $R^1$ are as defined in claim 1.

20. A compound according to claim 19 which is 1-[(4-piperidyl)methyl]-1H-2-methylimidazo[4,5-c]pyridine.

21. A method for the prevention or treatment of diseases mediated by platelet activating factor in a mammal, said method comprising administering an effective amount of the compound according to claim 1 to a mammal in need of such prevention or treatment.

* * * * *